(12) United States Patent
Corey et al.

(10) Patent No.: US 12,129,287 B2
(45) Date of Patent: Oct. 29, 2024

(54) RECOMBINANT ADENO ASSOCIATED VIRUS ENCODING CLARIN-1 AND USES THEREOF

(71) Applicants: President and Fellows of Harvard College, Cambridge, MA (US); The General Hospital Corporation, Boston, MA (US)

(72) Inventors: David P. Corey, Cambridge, MA (US); Casey A. Maguire, Arlington, MA (US); Killian S. Hanlon, Cambridge, MA (US); Maryna V. Ivanchenko, Cambridge, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 17/474,535

(22) Filed: Sep. 14, 2021

(65) Prior Publication Data
US 2022/0119475 A1    Apr. 21, 2022

Related U.S. Application Data

(60) Provisional application No. 63/180,537, filed on Apr. 27, 2021, provisional application No. 63/078,319, filed on Sep. 14, 2020.

(51) Int. Cl.
*C07K 14/705* (2006.01)
*A61K 48/00* (2006.01)
*A61P 27/16* (2006.01)
*C12N 15/86* (2006.01)

(52) U.S. Cl.
CPC ........ *C07K 14/705* (2013.01); *A61K 48/0058* (2013.01); *A61P 27/16* (2018.01); *C12N 15/86* (2013.01); *C12N 2750/14143* (2013.01); *C12N 2750/14171* (2013.01); *C12N 2800/90* (2013.01); *C12N 2840/105* (2013.01)

(58) Field of Classification Search
CPC ... C07K 14/705; A61P 27/16; A61K 48/0058; C12N 15/86; C12N 2750/14143; C12N 2750/14171; C12N 2800/90; C12N 2840/105
See application file for complete search history.

(56) References Cited

U.S. PATENT DOCUMENTS

| | | | |
|---|---|---|---|
| 5,399,363 A | 3/1995 | Liversidge et al. | |
| 5,543,158 A | 8/1996 | Gref et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,641,515 A | 6/1997 | Ramtoola | |
| 5,738,868 A | 4/1998 | Shinkarenko | |
| 5,741,516 A | 4/1998 | Webb et al. | |
| 5,795,587 A | 8/1998 | Gao et al. | |
| 6,001,650 A | 12/1999 | Colosi | |
| 6,156,303 A | 12/2000 | Russell et al. | |
| 7,198,951 B2 | 4/2007 | Gao et al. | |
| 9,102,949 B2 | 8/2015 | Gao et al. | |
| 9,585,971 B2 | 3/2017 | Deverman et al. | |
| 9,920,317 B2 | 3/2018 | Lee et al. | |
| 11,149,256 B2 * | 10/2021 | Gradinaru ............ | C07K 14/005 |
| 2003/0138772 A1 | 7/2003 | Gao et al. | |
| 2003/0194721 A1 | 10/2003 | Mikita et al. | |
| 2004/0214272 A1 | 10/2004 | La Rosa et al. | |
| 2007/0020624 A1 | 1/2007 | Rubenfield et al. | |
| 2008/0311627 A1 | 12/2008 | Tetzner et al. | |
| 2009/0270480 A1 | 10/2009 | Amegadzie et al. | |
| 2012/0164225 A1 | 6/2012 | Baum et al. | |
| 2014/0336245 A1 | 11/2014 | Mingozzi et al. | |
| 2017/0021038 A1 | 1/2017 | Pan et al. | |
| 2017/0166926 A1 | 6/2017 | Deverman et al. | |
| 2017/0183647 A1 | 6/2017 | Chavez et al. | |
| 2017/0240885 A1 | 8/2017 | Deverman et al. | |
| 2018/0187213 A1 | 7/2018 | High et al. | |

(Continued)

FOREIGN PATENT DOCUMENTS

CN    101883859 A    11/2010
CN    109207520 A    1/2019

(Continued)

OTHER PUBLICATIONS

Wang et al. A Rationally Engineered Capsid Variant of AAV9 for Systemic CNS-Directed and Peripheral Tissue-Detargeted Gene Delivery in Neonates. Molecular Therapy: Methods & Clinical Development. 2018; 9: 234-246. (Year: 2018).*
Extended European Search Report for Application No. EP 19785415.1, mailed Dec. 15, 2021.
International Search Report and Written Opinion for Application No. PCT/US2019/026852, mailed Jul. 10, 2019.
International Preliminary Report on Patentability for Application No. PCT/US2019/026852, mailed Oct. 22, 2020.
International Search Report and Written Opinion for Application No. PCT/US2021/050205, mailed Dec. 20, 2021.
Abelson et al., Methods in Enzymology. 2004. Academic Press, Eds.
Ahmad et al., 2001. Mutations of the protocadherin gene PCDH15 cause Usher syndrome type 1F. Am J Hum Genet. Jul. 2001;69(1):25-34. doi: 10.1086/321277. Epub Jun. 7, 2001.

(Continued)

*Primary Examiner* — Arthur S Leonard
*Assistant Examiner* — Jianjian Zhu
(74) *Attorney, Agent, or Firm* — Wolf, Greenfield & Sacks, P.C.

(57) ABSTRACT

Aspects of the disclosure relate to compositions and methods for treating hereditary hearing loss and/or vision loss, for example, due to Usher syndrome, Type 3A. In some embodiments, the disclosure provides a recombinant adeno-associated virus comprising: (i) an AAV-S capsid protein, and (ii) an isolated nucleic acid comprising a transgene (e.g., a transgene for expressing a clarin-1 protein). The present disclosure also provides methods of treating hereditary hearing loss and/or vision loss (e.g., Usher Syndrome, Type 3A) using the same.

17 Claims, 31 Drawing Sheets

Specification includes a Sequence Listing.

(56) References Cited

U.S. PATENT DOCUMENTS

| | | |
|---|---|---|
| 2018/0282382 A1 | 10/2018 | Alagramam |
| 2021/0079406 A1 | 3/2021 | Maguire et al. |
| 2022/0195458 A1 | 6/2022 | Maguire et al. |
| 2023/0340038 A1 | 10/2023 | Corey et al. |

FOREIGN PATENT DOCUMENTS

| | | |
|---|---|---|
| JP | 2008-263851 A | 11/2008 |
| RU | 2611202 C2 | 2/2017 |
| RU | 2018128780 A | 12/2018 |
| WO | WO 1998/00041 A1 | 1/1998 |
| WO | WO 2003/097685 A1 | 11/2003 |
| WO | WO 2006/119432 A2 | 11/2006 |
| WO | WO 2015/013148 A2 | 1/2015 |
| WO | WO 2015/038958 A1 | 3/2015 |
| WO | WO 2015/130840 A2 | 9/2015 |
| WO | WO 2017/100791 A1 | 6/2017 |
| WO | WO 2017/136536 A1 | 8/2017 |
| WO | WO 2018/022608 A2 | 2/2018 |
| WO | WO 2018/189244 A1 | 10/2018 |
| WO | WO 2019/028306 A2 | 2/2019 |
| WO | WO 2019/046069 A1 | 3/2019 |
| WO | WO 2019/200016 A1 | 10/2019 |
| WO | WO 2020/014471 A1 | 1/2020 |
| WO | WO 2020/077295 A1 | 4/2020 |
| WO | WO 2020/097372 A1 | 5/2020 |
| WO | WO 2020/198737 A1 | 10/2020 |
| WO | WO 2021/067448 A1 | 4/2021 |
| WO | WO 2022/232327 A2 | 11/2022 |

OTHER PUBLICATIONS

Ahmad et al., PCDH15 is expressed in the neurosensory epithelium of the eye and ear and mutant alleles are responsible for both USH1F and DFNB23. Hum Mol Genet. Dec. 15, 2003;12(24):3215-23. doi: 10.1093/hmg/ddg358. Epub Oct. 21, 2003.

Ahmad et al., Restoration of connexin26 protein level in the cochlea completely rescues hearing in a mouse model of human connexin30-linked deafness. Proc Natl Acad Sci U S A. Jan. 23, 2007;104(4):1337-41. doi: 10.1073/pnas.0606855104. Epub Jan. 16, 2007.

Akil et al., Restoration of hearing in the VGLUT3 knockout mouse using virally mediated gene therapy. Neuron. Jul. 26, 2012;75(2):283-93. doi: 10.1016/j.neuron.2012.05.019.

Alagramam et al., Mutations in protocadherin 15 and cadherin 23 affect tip links and mechanotransduction in mammalian sensory hair cells. PLoS One. Apr. 21, 2011;6(4):e19183. doi: 10.1371/journal.pone.0019183.

Al-Moyed et al., A dual-AAV approach restores fast exocytosis and partially rescues auditory function in deaf otoferlin knock-out mice. EMBO Mol Med. Jan. 2019;11(1):e9396. doi: 10.15252/emmm.201809396.

Angueyra et al., Leveraging Zebrafish to Study Retinal Degeneration. Front Cell Dev Biol. Sep. 19, 2018;6:110. doi: 10.3389/fcell.2018.00110. eCollection 2018.

Araya-Secchi et al., An elastic element in the protocadherin-15 tip link of the inner ear. Nat Commun. Nov. 18, 2016;7:13458. doi: 10.1038/ncomms13458.

ASGCT abstracts. Molecular Therapy. Apr. 28, 2020; 28(4S1): 2, 76, and 77.

Assad et al., An active motor model for adaptation by vertebrate hair cells. J Neurosci. Sep. 1992;12(9):3291-309. doi: 10.1523/JNEUROSCI.12-09-03291.1992.

Assad et al., Tip-link integrity and mechanical transduction in vertebrate hair cells. Neuron. Dec. 1991;7(6):985-94. doi: 10.1016/0896-6273(91)90343-x.

Azaiez et al., Genomic Landscape and Mutational Signatures of Deafness-Associated Genes. Am J Hum Genet. Oct. 4, 2018;103(4):484-497. doi: 10.1016/j.ajhg.2018.08.006. Epub Sep. 20, 2018.

Azaiez et al., GJB2: the spectrum of deafness-causing allele variants and their phenotype. Hum Mutat. Oct. 2004;24(4):305-11. doi: 10.1002/humu.20084.

Ben-Yosef et al., A mutation of PCDH15 among Ashkenazi Jews with the type 1 Usher syndrome. N Engl J Med. Apr. 24, 2003;348(17):1664-70. doi: 10.1056/NEJMoa021502.

Boulay et al., Hearing is normal without connexin30. J Neurosci. Jan. 9, 2013;33(2):430-4. doi: 10.1523/JNEUROSCI.4240-12.2013.

Brownstein et al., 2004. The R245X mutation of PCDH15 in Ashkenazi Jewish children diagnosed with nonsyndromic hearing loss foreshadows retinitis pigmentosa. Pediatr Res. 2004; 55: 995-1000.

Buenrostro et al., Transposition of native chromatin for fast and sensitive epigenomic profiling of open chromatin, DNA-binding proteins and nucleosome position. Nat Methods. Dec. 2013;10(12):1213-8. doi: 10.1038/nmeth.2688. Epub Oct. 6, 2013.

Chamberlain et al., Progress toward Gene Therapy for Duchenne Muscular Dystrophy. Mol Ther. 2017;25:1125-31.

Chan et al., Engineered AAVs for efficient noninvasive gene delivery to the central and peripheral nervous systems. Nat Neurosci. Aug. 2017; 20(8): 1172-1179. doi:10.1038/nn.4593.

Chang et al., Functional studies reveal new mechanisms for deafness caused by connexin mutations. Otol Neurotol. Feb. 2009;30(2):237-40. doi: 10.1097/MAO.0b013e318194f774.

Chang et al., Gap junction mediated intercellular metabolite transfer in the cochlea is compromised in connexin30 null mice. PloS one. 2008;3(12):e4088. doi: 10.1371/journal.pone.0004088. Epub Dec. 31, 2008.

Chang et al., Timed conditional null of connexin26 in mice reveals temporary requirements of connexin26 in key cochlear developmental events before the onset of hearing. Neurobiol Dis. Jan. 2015;73:418-27. doi: 10.1016/j.nbd.2014.09.005. Epub Sep. 22, 2014.

Chen et al., Characterization of a knock-in mouse model of the homozygous p.V37I variant in Gjb2. Sci Rep. Sep. 13, 2016;6:33279. doi: 10.1038/srep33279.

Chen et al., Developmental abnormalities in supporting cell phalangeal processes and cytoskeleton in the Gjb2 knockdown mouse model. Dis Model Mech. Feb. 26, 2018;11(2):dmm033019. doi: 10.1242/dmm.033019.

Chen et al., Down regulated connexin26 at different postnatal stage displayed different types of cellular degeneration and formation of organ of Corti. Biochem Biophys Res Commun. Feb. 28, 2014;445(1):71-7. doi: 10.1016/j.bbrc.2014.01.154. Epub Jan. 31, 2014.

Cheung et al., Ca2+ changes the force sensitivity of the hair-cell transduction channel. Biophys J. Jan. 1, 2006;90(1):124-39. doi: 10.1529/biophysj.105.061226. Epub Oct. 7, 2005.

Chow et al., Inducible Cre Recombinase Activity in Mouse Cerebellar Granule Cell Precursors and Inner Ear Hair Cells. Dev Dyn. Nov. 2006;235(11):2991-8. doi: 10.1002/dvdy.20948.

Christensen et al., TRP channels in mechanosensation : Direct or indirect activation? Nat Rev Neurosci. Jul. 2007;8(7):510-21. doi: 10.1038/nrn2149.

Cohen-Salmon et al., Targeted ablation of connexin26 in the inner ear epithelial gap junction network causes hearing impairment and cell death. Curr Biol. Jul. 9, 2002;12(13):1106-11. doi: 10.1016/s0960-9822(02)00904-1.

Corey et al., Kinetics of the receptor current in bullfrog saccular hair cells. J Neurosci. May 1983;3(5):962-76. doi: 10.1523/JNEUROSCI.03-05-00962.1983.

Corey et al., TRPA1 is a candidate for the mechanosensitive transduction channel of vertebrate hair cells. Nature. Dec. 9, 2004;432(7018):723-30. doi: 10.1038/nature03066. Epub Oct. 13, 2004.

Creyghton et al., Histone H3K27ac separates active from poised enhancers and predicts developmental state. Proc Natl Acad Sci U S A. Dec. 14, 2010;107(50):21931-6. doi: 10.1073/pnas.1016071107. Epub Nov. 24, 2010.

Crispino et al., BAAV mediated GJB2 gene transfer restores gap junction coupling in cochlear organotypic cultures from deaf Cx26Sox10Cre mice. PloS one. 2011;6(8):e23279. doi: 10.1371/journal.pone.0023279. Epub Aug. 18, 2011.

Crispino et al., In vivo genetic manipulation of inner ear connexin expression by bovine adeno-associated viral vectors. Sci Rep. Aug. 4, 2017;7(1):6567. doi: 10.1038/s41598-017-06759-y.

(56) References Cited

OTHER PUBLICATIONS

Dai et al., Rhesus Cochlear and Vestibular Functions Are Preserved After Inner Ear Injection of Saline Volume Sufficient for Gene Therapy Delivery. J Assoc Res Otolaryngol. Aug. 2017;18(4):601-617. doi: 10.1007/s10162-017-0628-6. Epub Jun. 23, 2017.
Darcy et al., Dual adeno-associated viral Anc80 vector efficiently transduces inner ear cells in non-human primates. ARO Abstract 691. 2020; 43: 447-48.
De Felipe et al., Tricistronic and tetracistronic retroviral vectors for gene transfer. Hum Gene Ther. Sep. 1, 2000;11(13):1921-31. doi: 10.1089/10430340050129530.
De Felipe et al., Use of the 2A sequence from foot-and-mouth disease virus in the generation of retroviral vectors for gene therapy. Gene Ther. Feb. 1999;6(2):198-208. doi: 10.1038/sj.gt.3300811.
Degen et al., Connexin32 can restore hearing in connexin26 deficient mice. Eur J Cell Biol. Oct. 2011;90(10):817-24. doi: 10.1016/j.ejcb.2011.05.001. Epub Aug. 2, 2011.
Del Castillo et al., A novel deletion involving the connexin-30 gene, del(GJB6-d13s1854), found in trans with mutations in the GJB2 gene (connexin-26) in subjects with DFNB1 non-syndromic hearing impairment. J Med Genet. Jul. 2005;42(7):588-94. doi: 10.1136/jmg.2004.028324.
Del Castillo et al., DFNB1 Non-syndromic Hearing Impairment: Diversity of Mutations and Associated Phenotypes. Front Mol Neurosci. Dec. 22, 2017;10:428. doi: 10.3389/fnmol.2017.00428. eCollection 2017.
Delmaghani et al., Inner ear gene therapies take off: current promises and future challenges. J Clin Med. Jul. 21, 2020;9(7):2309. doi: 10.3390/jcm9072309.
Derby et al., Gene transfer into the mammalian inner ear using HSV-1 and vaccinia virus vectors. Hear Res. Aug. 1999;134(1-2):1-8. doi: 10.1016/s0378-5955(99)00045-3.
Deverman et al., Cre-dependent selection yields AAV variants for widespread gene transfer to the adult brain. Nat Biotechnol. Feb. 2016;34(2):204-9.
Dinh et al., Diverse deafness mechanisms of connexin mutations revealed by studies using in vitro approaches and mouse models. Brain Res. Jun. 24, 2009;1277:52-69. doi: 10.1016/j.brainres.2009.02.008. Epub Feb. 20, 2009.
Doane et al., Regulatory elements in molecular networks. Wiley Interdiscip Rev Syst Biol Med. May 2017;9(3):10.1002/wsbm.1374. doi: 10.1002/wsbm.1374. Epub Jan. 17, 2017.
Doucette et al., Profound, prelingual nonsyndromic deafness maps to chromosome 10q21 and is caused by a novel missense mutation in the Usher syndrome type IF gene PCDH15. Eur J Hum Genet. May 2009;17(5):554-64. doi: 10.1038/ejhg.2008.231. Epub Dec. 24, 2008.
Dulon et al., Clarin-1 gene transfer rescues auditory synaptopathy in model of Usher syndrome, J Clin Invest. Aug. 1, 2018;128(8):3382-3401. doi: 10.1172/JCI94351. Epub Jul. 9, 2018.
Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.
Ellis et al., A survey of ex vivo/in vitro transduction efficiency of mammalian primary cells and cell lines with Nine natural adeno-associated virus (AAV1-9) and one engineered adeno-associated virus serotype. Virol J. Mar. 6, 2013;10:74. doi: 10.1186/1743-422X-10-74.
Feigenspan et al., Expression of connexin36 in cone pedicles and OFF-cone bipolar cells of the mouse retina. J Neurosci. Mar. 31, 2004;24(13):3325-34. doi: 10.1523/JNEUROSCI.5598-03.2004.
Fetoni et al., Cx26 partial loss causes accelerated presbycusis by redox imbalance and dysregulation of Nfr2 pathway. Redox Biol. Oct. 2018;19:301-317. doi: 10.1016/j.redox.2018.08.002. Epub Aug. 7, 2018.
Fields et al., Usher syndrome type III: revised genomic structure of the USH3 gene and identification of novel mutations. Am J Hum Genet. Sep. 2002;71(3):607-17. doi: 10.1086/342098. Epub Jul. 16, 2002.

Forge et al., Gap junctions and connexin expression in the inner ear. Novartis Found Symp. 1999;219:134-50; discussion 151-6. doi: 10.1002/9780470515587.ch9.
Forge et al., Gap junctions in the inner ear: comparison of distribution patterns in different vertebrates and assessement of connexin composition in mammals. J Comp Neurol. Dec. 8, 2003;467(2):207-31. doi: 10.1002/cne.10916.
Furler et al., Recombinant AAV vectors containing the foot and mouth disease virus 2A sequence confer efficient bicistronic gene expression in cultured cells and rat substantia nigra neurons. Gene Ther. Jun. 2001;8(11):864-73. doi: 10.1038/sj.gt.3301469.
Garcia et al., Localization of myosin-Iβ near both ends of tip links in frog saccular hair cells. J Neurosci. Nov. 1, 1998;18(21):8637-47. doi: 10.1523/JNEUROSCI.18-21-08637.1998.
Gaudelli et al., Programmable base editing of A*T to G*C in genomic DNA without DNA cleavage. Nature. Nov. 23, 2017;551(7681):464-471. doi: 10.1038/nature24644. Epub Oct. 25, 2017.
Ge et al., Structure of mouse protocadherin 15 of the stereocilia tip link in complex with LHFPL5. Elife. Aug. 2, 2018;7:e38770. doi: 10.7554/eLife.38770.
Genbank Submission. NCBI; Accession No. AAM88774, version AAM88774.1. clarin-1 [Homo sapiens]. Adato et al.; Aug. 5, 2002.
Genbank Submission. NCBI; Accession No. NM_004004, version NM_004004.6. Homo sapiens gap junction protein beta 2 (GJB2), mRNA. Kausar et al.; Dec. 20, 2021.
Genbank Submission. NCBI; Accession No. NP_001182723, version NP_001182723.1. clarin-1 isoform d [Homo sapiens]. Luck et al.; Oct. 11, 2020.
Genbank Submission. NCBI; Accession No. NP_001243748, version NP_001243748.1. clarin-1 isoform e [Homo sapiens]. Luck et al.; Dec. 13, 2020.
Genbank Submission. NCBI; Accession No. NP_443721, version NP_443721.1. clarin-1 isoform c [Homo sapiens]. Luck et al.; Oct. 10, 2020.
Genbank Submission. NCBI; Accession No. NP_700433, version NP_700433.1. clarin-1 isoform 1 [Mus musculus]. Dulon et al.; Dec. 3, 2021.
Genbank Submission. NCBI; Accession No. NP_700434, version NP_700434.1. clarin-1 isoform 2 [Mus musculus]. Dulon et al.; Dec. 2, 2021.
Genbank Submission. NCBI; Accession No. NP_700435, version NP_700435.1. clarin-1 isoform 3 [Mus musculus]. Dulon et al.; Oct. 10, 2020.
Genbank Submission. NCBI; Accession No. NP_777367, version NP_777367.1. clarin-1 isoform a [Homo sapiens]. Luck et al.; Apr. 6, 2021.
Geng et al., Modeling and Preventing Progressive Hearing Loss in Usher Syndrome III. Sci Rep. Oct. 18, 2017;7(1):13480. doi: 10.1038/s41598-017-13620-9.
Gregorevic et al., rAAV6-microdystrophin preserves muscle function and extends lifespan in severely dystrophic mice. Nat Med. Jul. 2006;12(7):787-9. doi: 10.1038/nm1439. Epub Jul. 2, 2006.
Grimm et al., In vitro and in vivo gene therapy vector evolution via multispecies interbreeding and retargeting of adeno-associated viruses. J Virol. Jun. 2008;82(12):5887-911. doi: 10.1128/JVI.00254-08. Epub Apr. 9, 2008.
György et al., Allele-specific gene editing prevents deafness in a model of dominant progressive hearing loss. Nat Med. Jul. 2019;25(7):1123-1130. doi: 10.1038/s41591-019-0500-9. Epub Jul. 3, 2019.
György et al., An AAV9 capsid variant efficiently transduces inner ear hair cells in mice and non-human primates and rescues hearing in a mouse model of human deafness. Mol Ther Methods Clin Dev. Nov. 20, 2018;13:1-13. doi: 10.1016/j.omtm.2018.11.003. eCollection Jun. 14, 2019.
György et al., Rescue of Hearing by Gene Delivery to Inner-Ear Hair Cells Using Exosome-Associated AAV. Mol Ther. Feb. 1, 2017;25(2):379-391.
Halpin et al., Self-processing 2A-polyproteins—a system for co-ordinate expression of multiple proteins in transgenic plants. Plant J. Feb. 1999;17(4):453-9. doi: 10.1046/j.1365-313x.1999.00394.x.

(56) References Cited

OTHER PUBLICATIONS

Hanlon et al., AAV-S: A novel AAV vector selected in brain transduces the inner ear with high efficiency. ASGCT poster. Harvard Medical School. Apr. 28, 2020. 1 page.

Hanlon et al., Selection of an Efficient AAV Vector for Robust CNS Transgene Expression. Mol Ther Methods Clin Dev. Oct. 23, 2019;15:320-332. doi: 10.1016/j.omtm.2019.10.007. eCollection Dec. 13, 2019.

Hasson et al., Unconventional myosins in inner-ear sensory epithelia J Cell Biol. Jun. 16, 1997;137(6):1287-307. doi: 10.1083/jcb.137.6.1287.

Hirsch et al., Delivering Transgenic DNA Exceeding the Carrying Capacity of AAV Vectors. Methods Mol Biol. 2016;1382:21-39. doi: 10.1007/978-1-4939-3271-9_2.

Holt et al., A chemical-genetic strategy demonstrates myosin 1c mediates sensory adaptation in hair cells. Cell. Feb. 8, 2002;108(3):371-81. doi: 10.1016/s0092-8674(02)00629-3.

Holt et al., Functional expression of exogenous proteins in mammalian sensory hair cells infected with adenoviral vectors. J Neurophysiol. Apr. 1999;81(4):1881-8. doi: 10.1152/jn.1999.81.4.1881.

Hordeaux et al., The Neurotropic Properties of AAV-PHP.B Are Limited to C57BL/6J Mice. Mol Ther. Mar. 7, 2018;26(3):664-668. doi: 10.1016/j.ymthe.2018.01.018. Epub Feb. 2, 2018.

Hrvatin et al., Single-cell analysis of experience-dependent transcriptomic states in the mouse visual cortex. Nat Neurosci. Jan. 2018;21(1):120-129. doi: 10.1038/s41593-017-0029-5. Epub Dec. 11, 2017.

Huang et al., Role of the hepatitis B virus posttranscriptional regulatory element in export of intronless transcripts. Mol Cell Biol. 1995;15(7):3864-3869. doi: 10.1128/MCB.15.7.3864.

Iizuka et al., Perinatal Gjb2 gene transfer rescues hearing in a mouse model of hereditary deafness. Hum Mol Genet. Jul. 1, 2015;24(13):3651-61. doi: 10.1093/hmg/ddv109. Epub Mar. 23, 2015.

Indzhykulian et al., Molecular remodeling of tip links underlies mechanosensory regeneration in auditory hair cells. PLoS Biol. 2013;11(6):e1001583. doi: 10.1371/journal.pbio.1001583. Epub Jun. 11, 2013.

Iossa et al., GJB2 Gene Mutations in Syndromic Skin Diseases with Sensorineural Hearing Loss, Curr Genomics. Nov. 2011;12(7):475-785. doi: 10.2174/138920211797904098.

Isgrig et al., AAV2.7m8 is a powerful viral vector for inner ear gene therapy. Nat Commun. Jan. 25, 2019;10(1):427. doi: 10.1038/s41467-018-08243-1.

Ivanchenko et al., AAV-S: A versatile capsid variant for transduction of mouse and primate inner ear. Mol Ther Methods Clin Dev. Mar. 29, 2021;21:382-398. doi: 10.1016/j.omtm.2021.03.019. eCollection Jun. 11, 2021.

Ivanchenko et al., Preclinical testing of AAV9-PHP.B for transgene expression in the non-human primate cochlea. Hear Res. Sep. 1, 2020;394:107930. doi: 10.1016/j.heares.2020.107930. Epub Feb. 26, 2020.

Johnson et al., Connexin-Mediated Signaling in Nonsensory Cells Is Crucial for the Development of Sensory Inner Hair Cells in the Mouse Cochlea. J Neurosci. Jan. 11, 2017;37(2):258-268. doi: 10.1523/JNEUROSCI.2251-16.2016.

Jovičić et al., Comprehensive Expression Analyses of Neural Cell-Type-Specific miRNAs Identify New Determinants of the Specification and Maintenance of Neuronal Phenotypes. J Neurosci. Mar. 20, 2013;33(12):5127-37. doi: 10.1523/JNEUROSCI.0600-12.2013.

Kamiya et al., Assembly of the cochlear gap junction macromolecular complex requires connexin 26. J Clin Invest. Apr. 2014;124(4):1598-607. doi: 10.1172/JCI67621. Epub Mar. 3, 2014.

Kazmierczak et al., Cadherin 23 and protocadherin 15 interact to form tip-link filaments in sensory hair cells. Nature. Sep. 6, 2007;449(7158):87-91. doi: 10.1038/nature06091.

Kelsell et al., Connexin 26 mutations in hereditary non-syndromic sensorineural deafness. Nature. May 1, 1997;387(6628):80-3. doi: 10.1038/387080a0.

Kenna et al., Audiologic phenotype and progression in GJB2 (Connexin 26) hearing loss. Arch Otolaryngol Head Neck Surg. Jan. 2010;136(1):81-7. doi: 10.1001/archoto.2009.202.

Keppeler et al., Ultrafast optogenetic stimulation of the auditory pathway by targeting-optimized Chronos. EMBO J. Dec. 14, 2018;37(24):e99649. doi: 10.15252/embj.201899649. Epub Nov. 5, 2018.

Kiang et al., Upstream genomic sequence of the human connexin26 gene. Gene. Oct. 15, 1997;199(1-2):165-71. doi: 10.1016/s0378-1119(97)00365-x.

Kikuchi et al., Gap junction systems in the mammalian cochlea, Brain Res Brain Res Rev. Apr. 2000;32(1):163-6. doi: 10.1016/s0165-0173(99)00076-4.).

Kikuchi et al., Gap junctions in the rat cochlea: immunohistochemical and ultrastructural analysis. Anat Embryol (Berl). Feb. 1995;191(2):101-18. doi: 10.1007/BF00186783.

Klump et al., Retroviral vector-mediated expression of HoxB4 in hematopoietic cells using a novel coexpression strategy. Gene Ther. May 2001;8(10):811-7. doi: 10.1038/sj.gt.3301447.

Kodippili et al., Dual AAV Gene Therapy for Duchenne Muscular Dystrophy with a 7-kb Mini-Dystrophin Gene in the Canine Model. Hum Gene Ther. Mar. 2018;29(3):299-311. doi: 10.1089/hum.2017.095. Epub Aug. 4, 2017.

Koehler et al., Generation of inner ear organoids containing functional hair cells from human pluripotent stem cells. Nat Biotechnol. Jun. 2017;35(6):583-589. doi: 10.1038/nbt.3840. Epub May 1, 2017.

Kohrman et al., Gene therapy for deafness. Gene Ther. Dec. 2013;20(12):1119-23. doi: 10.1038/gt.2013.39. Epub Jul. 18, 2013.

Kwan et al., TRPA1 contributes to cold, mechanical, and chemical nociception but is not essential for hair-cell transduction. Neuron. Apr. 20, 2006;50(2):277-89. doi: 10.1016/j.neuron.2006.03.042.

Landegger et al., A synthetic AAV vector enables safe and efficient gene transfer to the mammalian inner ear. Nat Biotechnol. Mar. 2017;35(3):280-284.

Lang et al., Effects of chronic furosemide treatment and age on cell division in the adult gerbil inner ear. J Assoc Res Otolaryngol. Jun. 2003;4(2):164-75. doi: 10.1007/s10162-002-2056-4.

Lee et al., Efficient viral transduction in mouse inner ear hair cells with utricle injection and AAV9-PHP.B. Hear Res. Sep. 1, 2020;394:107882. doi: 10.1016/j.heares.2020.107882. Epub Jan. 13, 2020.

Lee et al., Mice with conditional deletion of Cx26 exhibit no vestibular phenotype despite secondary loss of Cx30 in the vestibular end organs. Hearing Res. Oct. 2015;328:102-12. doi: 10.1016/j.heares.2015.07.018. Epub Jul. 29, 2015.

Levy et al., Cytosine and adenine base editing of the brain, liver, retina, heart and skeletal muscle of mice via adeno-associated viruses. Nat Biomed Eng. Jan. 2020;4(1):97-110. doi: 10.1038/s41551-019-0501-5. Epub Jan. 14, 2020.

Li et al., Characterization of slow-cycling cells in the mouse cochlear lateral wall. PloS one. Jun. 20, 2017;12(6):e0179293. doi: 10.1371/journal.pone.0179293. eCollection 2017.

Li et al., MicroRNAs in hair cell development and deafness. Curr Opin Otolaryngol Head Neck Surg. Oct. 2010;18(5):459-65. doi: 10.1097/MOO.0b013e32833e0601.

Li et al., Notch inhibition induces mitotically generated hair cells in mammalian cochleae via activating the Wnt pathway. Proc Natl Acad Sci U S A. Jan. 6, 2015;112(1):166-71. doi: 10.1073/pnas.1415901112. Epub Dec. 22, 2014.

Lin et al., Hearing loss and incident dementia. Arch Neurol. Feb. 2011;68(2):214-20. doi: 10.1001/archneurol.2010.362.

Lin et al., Hearing loss prevalence in the United States. Arch Intern Med. Nov. 14, 2011;171(20):1851-2. doi: 10.1001/archinternmed.2011.506.

Lukashkina et al., Amplification mode differs along the length of the mouse cochlea as revealed by connexin 26 deletion from specific gap junctions. Sci Rep. Jul. 12, 2017;7(1):5185. doi: 10.1038/s41598-017-04279-3.

Lustig et al.,, Cochlear Gene Therapy. Cold Spring Harb Perspect Med. Sep. 3, 2019;9(9):a033191. doi: 10.1101/cshperspect.a033191.

(56) References Cited

OTHER PUBLICATIONS

Ma et al., Connexin 26 in mature ears influences survival of hair cells and neurons. ARO Abstract 404. 2020; 43:258-9.
Maguire et al., Efficacy, Safety, and Durability of Voretigene Neparvovec-rzyl in RPE65 Mutation-Associated Inherited Retinal Dystrophy: Results of Phase 1 and 3 Trials. Ophthalmology. Sep. 2019;126(9):1273-1285. doi: 10.1016/j.ophtha.2019.06.017. Epub Jun. 22, 2019.
Mahendrasingam et al., Subcellular distribution and relative expression of fibrocyte markers in the CD/1 mouse cochlea assessed by semiquantitative immunogold electron microscopy. J Histochem Cytochem. Nov. 2011;59(11):984-1000. doi: 10.1369/0022155411421801.
Mammano, Inner Ear Connexin Channels: Roles in Development and Maintenance of Cochlear Function. Cold Spring Harb Perspect Med. Jul. 1, 2019;9(7):a033233. doi: 10.1101/cshperspect.a033233.
Mason et al., Universal infant hearing screening by automated auditory brainstem response measurement. Pediatrics. Feb. 1998;101(2):221-8. doi: 10.1542/peds.101.2.221.
Matsuzaki et al., Intravenous administration of the adeno-associated virus-PHP.B capsid fails to upregulate transduction efficiency in the marmoset brain. Neurosci Lett. Feb. 5, 2018;665:182-188. doi: 10.1016/j.neulet.2017.11.049. Epub Nov. 24, 2017.
Mattion et al., Foot-and-mouth disease virus 2A protease mediates cleavage in attenuated Sabin 3 poliovirus vectors engineered for delivery of foreign antigens. J Virol. Nov. 1996;70(11):8124-7. doi: 10.1128/JVI.70.11.8124-8127.1996.
McCarthy, Self-complementary AAV vectors; advances and applications. Mol Ther. Oct. 2008;16(10):1648-56. doi: 10.1038/mt.2008.171. Epub Aug. 5, 2008.
Mclean et al., GREAT improves functional interpretation of cis-regulatory regions. Nat Biotechnol. May 2010;28(5):495-501. doi: 10.1038/nbt.1630. Epub May 2, 2010.
Mei et al., A deafness mechanism of digenic Cx26 (GJB2) and Cx30 (GJB6) mutations: Reduction of endocochlear potential by impairment of heterogeneous gap junctional function in the cochlear lateral wall. Neurobiol Dis. Dec. 2017;108:195-203. doi: 10.1016/j.nbd.2017.08.002. Epub Aug. 17, 2017.
Mutai et al., Mitotic activity and specification of fibrocyte subtypes in the developing rat cochlear lateral wall. Neuroscience. Nov. 10, 2009;163(4):1255-63. doi: 10.1016/j.neuroscience.2009.07.059. Epub Aug. 4, 2009.
Narui et al., Tuning Inner-Ear Tip-Link Affinity Through Alternatively Spliced Variants of Protocadherin-15. Biochemistry. Mar. 20, 2018;57(11):1702-1710. doi: 10.1021/acs.biochem.7b01075. Epub Mar. 6, 2018.
Nickel et al., Gap junctions and connexins in the inner ear: their roles in homeostasis and deafness. Curr Opin Otolaryngol Head Neck Surg. Oct. 2008;16(5):452-7. doi: 10.1097/MOO.0b013e32830e20b0.
Niwa et al., In vitro polyadenylation is stimulated by the presence of an upstream intron. Genes Dev. Sep. 1990;4(9):1552-9. doi: 10.1101/gad.4.9.1552.
No et al., Ecdysone-inducible gene expression in mammalian cells and transgenic mice. Proc Natl Acad Sci U S A. Apr. 16, 1996;93(8):3346-3351.
Olson et al., Post-translational tools expand the scope of synthetic biology. Curr Opin Chem Biol. Aug. 2012;16(3-4):300-6. doi: 10.1016/j.cbpa.2012.06.003. Epub Jul. 4, 2012.
Pan et al., Gene therapy restores auditory and vestibular function in a mouse model of Usher syndrome type 1c. Nat Biotechnol. Mar. 2017;35(3):264-272. doi: 10.1038/nbt.3801. Epub Feb. 6, 2017.
Pepermans et al., The CD2 isoform of protocadherin-15 is an essential component of the tip-link complex in mature auditory hair cells. EMBO Mol Med. Jul. 2014;6(7):984-92. doi: 10.15252/emmm.201403976.
Powers et al., A Partial Calcium-Free Linker Confers Flexibility to Inner-Ear Protocadherin-15. Structure. Mar. 7, 2017;25(3):482-495. doi: 10.1016/j.str.2017.01.014. Epub Feb. 23, 2017.
Rada-Iglesias et al., A unique chromatin signature uncovers early developmental enhancers in humans. Nature. Feb. 10, 2011;470(7333):279-83. doi: 10.1038/nature09692. Epub Dec. 15, 2010.
Rees et al., Base editing: precision chemistry on the genome and transcriptome of living cells. Nat Rev Genet. Dec. 2018;19(12):770-788. doi: 10.1038/s41576-018-0059-1.
Rodriguez-Paris et al., Comparative functional characterization of novel non-syndromic GJB2 gene variant p.Gly45Arg and lethal syndromic variant p.Gly45Glu. PeerJ. Oct. 11, 2016;4:e2494. doi: 10.7717/peerj.2494. eCollection 2016.
Ross, Comments on the article "Persistent confusion of total entropy and chemical system entropy in chemical thermodynamics" [(1996) Proc. Natl. Acad. Sci. USA 93, 7452-7453]. Proc Natl Acad Sci USA. Dec. 10, 1996;93(25):14314; discussion 14315. doi: 10.1073/pnas.93.25.14314.
Ross, Comments on the article "Persistent confusion of total entropy and chemical system entropy in chemical thermodynamics" [(1996) Proc. Natl. Acad. Sci. USA 93, 7452-7453]. Proc Natl Acad Sci U S A. Dec. 10, 1996;93(25):14314; discussion 14315.
Ryan et al., Foot-and-mouth disease virus 2A oligopeptide mediated cleavage of an artificial polyprotein. EMBO J. Feb. 15, 1994;13(4):928-33.
Sacheli et al., Gene transfer in inner ear cells: a challenging race. Gene Ther. Mar. 2013;20(3):237-47. doi: 10.1038/gt.2012.51. Epub Jun. 28, 2012.
Scheffer et al., Gene expression profiling identifies Hes6 as a transcriptional target of ATOH1 in cochlear hair cells. FEBS Lett. Oct. 2, 2007;581(24):4651-6. doi: 10.1016/j.febslet.2007.08.059. Epub Sep. 4, 2007.
Scheffer et al., The alpha1 subunit of nicotinic acetylcholine receptors in the inner ear: transcriptional regulation by ATOH1 and co-expression with the gamma subunit in hair cells. J Neurochem. Dec. 2007;103(6):2651-64. doi: 10.1111/j.1471-4159.2007.04980.x.
Scheffer et al., XIRP2, an actin-binding protein essential for inner ear hair-cell stereocilia. Cell Rep. Mar. 24, 2015;10(11):1811-8. doi: 10.1016/j.celrep.2015.02.042. Epub Mar. 12, 2015.
Senis et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014.
Shepherd et al., The extent of adaptation in bullfrog saccular hair cells. J Neurosci. Oct. 1994;14(10):6217-29. doi: 10.1523/JNEUROSCI.14-10-06217.1994.
Shu et al., Identification of Adeno-Associated Viral Vectors That Target Neonatal and Adult Mammalian Inner Ear Cell Subtypes. Hum Gene Ther. Sep. 2016;27(9):687-99. doi: 10.1089/hum.2016.053. Epub Jun. 24, 2016.
Solc et al., Molecular cloning of myosins from the bullfrog saccular macula: A candidate for the adaptation motor. Auditory Neurosci. 1994; 1:63-75.
Sotomayor et al., In search of the hair-cell gating spring: Elastic properties of ankyrin and cadherin repeats. Structure. Apr. 2005;13(4):669-82. doi: 10.1016/j.str.2005.03.001.
Sotomayor et al., Structural determinants of cadherin-23 function in hearing and deafness. Neuron. Apr. 15, 2010;66(1):85-100. doi: 10.1016/j.neuron.2010.03.028.
Sotomayor et al., Structure of a force-conveying cadherin bond essential for inner-ear mechanotransduction. Nature. Dec. 6;492(7427):128-32. doi: 10.1038/nature11590. Epub Nov. 7, 2012.
Srinivas et al., Human diseases associated with connexin mutations. Biochim Biophys Acta Biomembr. Jan. 2018;1860(1):192-201. doi: 10.1016/j.bbamem.2017.04.024. Epub Apr. 27, 2017.
Sun et al., Connexin30 null and conditional connexin26 null mice display distinct pattern and time course of cellular degeneration in the cochlea. J Comp Neurol. Oct. 20, 2009;516(6):569-79. doi: 10.1002/cne.22117.
Suzuki et al., Cochlear gene therapy with ancestral AAV in adult mice: complete transduction of inner hair cells without cochlear dysfunction. Sci Rep. Apr. 3, 2017;7:45524. doi: 10.1038/srep45524.

(56) References Cited

OTHER PUBLICATIONS

Takada et al., Connexin 26 null mice exhibit spiral ganglion degeneration that can be blocked by BDNF gene therapy. Hearing Res. Mar. 2014;309:124-35. doi: 10.1016/j.heares.2013.11.009. Epub Dec. 12, 2013.
Tao et al., Delivery of adeno-associated virus vectors in adult mammalian inner-ear cell subtypes without auditory dysfunction. Hum Gene Ther. Apr. 2018;29(4):492-506. doi: 10.1089/hum.2017.120. Epub Jan. 22, 2018.
Trapani et al., Effective delivery of large genes to the retina by dual AAV vectors. EMBO Mol Med. Feb. 2014;6(2):194-211. doi: 10.1002/emmm.201302948. Epub Dec. 15, 2013.
Trapani et al., Seeing the Light after 25 Years of Retinal Gene Therapy. Trends Mol Med. Aug. 2018;24(8):669-681. doi: 10.1016/j.molmed.2018.06.006. Epub Jul. 5, 2018.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tu et al., Mapping and characterization of the basal promoter of the human connexin26 gene. Biochim Biophys Acta. Nov. 26, 1998;1443(1-2):169-81. doi: 10.1016/s0167-4781(98)00212-7.
Västinsalo et al., Alternative splice variants of the USH3A gene Clarin 1 (CLRN1). Eur J Hum Genet. Jan. 2011;19(1):30-5. doi: 10.1038/ejhg.2010.140. Epub Aug. 18, 2010.
Vogl et al., Tryptophan-rich basic protein (WRB) mediates insertion of the tail-anchored protein otoferlin and is required for hair cell exocytosis and hearing. EMBO J. Dec. 1, 2016;35(23):2536-2552. doi: 10.15252/embj.201593565. Epub Jul. 25, 2016.
Wan et al., Inner ear supporting cells: Rethinking the silent majority. Semin Cell Dev Biol. May 2013;24(5):448-59. doi: 10.1016/j.semcdb.2013.03.009. Epub Mar. 29, 2013.
Wang et al., Targeted connexin26 ablation arrests postnatal development of the organ of Corti. Biochem Biophys Res Commun. Jul. 17, 2009;385(1):33-7. doi: 10.1016/j.bbrc.2009.05.023. Epub May 9, 2009.
Wassmer et al., Exosome-associated AAV2 vector mediates robust gene delivery into the murine retina upon intravitreal injection. Sci Rep. Mar. 31, 2017;7:45329. doi: 10.1038/srep45329.
Watanabe et al., Expression of the Sox10 gene during mouse inner ear development. Brain Res Mol Brain Res. Dec. 8, 2000;84(1-2):141-5. doi: 10.1016/s0169-328x(00)00236-9.
Wilch et al., A novel DFNB1 deletion allele supports the existence of a distant cis-regulatory region that controls GJB2 and GJB6 expression. Clin Genet. Sep. 2010;78(3):267-74. doi: 10.1111/j.1399-0004.2010.01387.x. Epub Mar. 1, 2010.
Wingard et al., Cellular and Deafness Mechanisms Underlying Connexin Mutation-Induced Hearing Loss—A Common Hereditary Deafness. Front Cell Neurosci. May 29, 2015;9:202. doi: 10.3389/fncel.2015.00202. eCollection 2015.
Wise et al., The effect of deafness duration on neurotrophin gene therapy for spiral ganglion neuron protection. Hearing Res. Aug. 2011;278(1-2):69-76. doi: 10.1016/j.heares.2011.04.010. Epub May 1, 2011.
Wu et al., Hair-cell mechanotransduction persists in TRP channel knockout mice. PloS One. May 19, 2016;11(5):e0155577. doi: 10.1371/journal.pone.0155577. eCollection 2016.
Xia et al., Expression of connexin 26 and Na,K-ATPase in the developing mouse cochlear lateral wall: functional implications. Brain Res. Oct. 30, 1999;846(1):106-11. doi: 10.1016/s0006-8993(99)01996-4.
Yang et al., Gfi1-Cre knock-in mouse line: A tool for inner ear hair cell-specific gene deletion. Genesis. Jun. 2010;48(6):400-6. doi: 10.1002/dvg.20632.
Yeh et al., 2020. In vivo base editing rescues hearing in a mouse model of recessive deafness. ARO Abstract 172. 2020;43:96-7.
Yeh et al., In vivo base editing of post-mitotic sensory cells. Nature Commun. Jun. 5, 2018;9(1):2184. doi: 10.1038/s41467-018-04580-3.
Yu et al., Supplementary Figure 2 to: Virally expressed connexin26 restores gap junction function in the cochlea of conditional Gjb2 knockout mice. Gene Ther. Nov. 2013. 1 page.
Yu et al., Virally expressed connexin26 restores gap junction function in the cochlea of conditional Gjb2 knockout mice. Gene Ther. Jan. 2014;21(1):71-80. doi: 10.1038/gt.2013.59. Epub Nov. 14, 2013.
Zallocchi et al., Localization and expression of clarin-1, the Clrn1 gene product, in auditory hair cells and photoreceptors. Hear Res. Sep. 2009;255(1-2):109-20. doi: 10.1016/j.heares.2009.06.006. Epub Jun. 16, 2009.
Zelante et al., Connexin26 mutations associated with the most common form of non-syndromic neurosensory autosomal recessive deafness (DFNB1) in Mediterraneans. Hum Mol Genet. Sep. 1997;6(9):1605-9. doi: 10.1093/hmg/6.9.1605.
Zhang et al., Cochlear Gene Therapy for Sensorineural Hearing Loss: Current Status and Major Remaining Hurdles for Translational Success. Front Mol Neurosci. Jun. 26, 2018;11:221. doi: 10.3389/fnmol.2018.00221. eCollection 2018.
Zhu et al., Active cochlear amplification is dependent on supporting cell gap junctions. Nature Commun. 2013;4:1786. doi: 10.1038/ncomms2806.
International Preliminary Report on Patentability for Application No. PCT/US2021/050205, mailed Mar. 23, 2023.
Chen et al., Engineered AAVs for efficient noninvasive gene delivery to the central and peripheral nervous systems. Nat Neurosci. Author manuscript; available in PMC Dec. 26, 2017. Published in final edited form as: Nat Neurosci. Aug. 2017; 20(8): 1172-1179. Published online Jun. 26, 2017. doi: 10.1038/nn.4593.
Trapani, Dual AAV Vectors for Stargardt Disease. Methods Mol Biol. 2018;1715:153-175. doi: 10.1007/978-1-4939-7522-8_11.
Partial European Search Report for Application No. 20779113.8, mailed Nov. 23, 2022.
Extended European Search Report for Application No. 20779113.8, mailed Apr. 18, 2023.
Invitation to Pay Additional Fees for Application No. PCT/US2022/026608, mailed Aug. 15, 2022.
International Search Report and Written Opinion for Application No. PCT/US2022/026608, mailed Oct. 12, 2022.
International Search Report and Written Opinion for Application No. PCT/US2020/025720, mailed Jul. 27, 2020.
International Preliminary Report on Patentability for Application No. PCT/US2020/025720, mailed Oct. 7, 2021.
Chinese Office Action for Application No. 202080038934.8, mailed Aug. 26, 2023.
Russian Office Action for Application No. 2021131423, mailed Aug. 8, 2023.
Singapore Office Action for Application No. 11202110165X, mailed Aug. 16, 2023.
No Author Listed, GenBank Accession No. KAA0147029.1. hypothetical protein FNF29 07656 [Cafeteria roenbergensis]. Sep. 9, 2019. 2 pages.
Akil et al., Dual AAV-mediated gene therapy restores hearing in a DFNB9 mouse model. Proc Natl Acad Sci U S A. Mar. 5, 2019;116(10):4496-4501. doi: 10.1073/pnas.1817537116. Epub Feb. 19, 2019.
Al-Zaidy et al., AVXS-101 (Onasemnogene Abeparvovec) for SMA1: Comparative Study with a Prospective Natural History Cohort. J Neuromuscul Dis. 2019;6(3):307-317. doi: 10.3233/JND-190403.
Aurnhammer et al., Universal real-time PCR for the detection and quantification of adeno-associated virus serotype 2-derived inverted terminal repeat sequences. Hum Gene Ther Methods. Feb. 2012;23(1):18-28. doi: 10.1089/hgtb.2011.034.
Berry et al., Cellular transduction mechanisms of adeno-associated viral vectors. Curr Opin Virol. Curr Opin Virol. Dec. 2016;21:54-60. doi: 10.1016/j.coviro.2016.08.001. Epub Aug. 18, 2016.
Caron et al., Potent and sustained huntingtin lowering via AAV5 encoding miRNA preserves striatal volume and cognitive function in a humanized mouse model of Huntington disease. Nucleic Acids Res. Jan. 10, 2020;48(1):36-54. doi: 10.1093/nar/gkz976.
Cehajic-Kapetanovic et al., Initial results from a first-in-human gene therapy trial on X-linked retinitis pigmentosa caused by mutations

(56) References Cited

OTHER PUBLICATIONS in RPGR. Nat Med. Mar. 2020;26(3):354-359. doi: 10.1038/s41591-020-0763-1. Epub Feb. 24, 2020.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Christine et al., Magnetic resonance imaging-guided phase 1 trial of putaminal AADC gene therapy for Parkinson's disease. Ann Neurol. May 2019;85(5):704-714. doi: 10.1002/ana.25450. Epub Mar. 26, 2019.
Dashkoff et al., Tailored transgene expression to specific cell types in the central nervous system after peripheral injection with AAV9. Mol Ther Methods Clin Dev. Dec. 7, 2016;3:16081. doi: 10.1038/mtm.2016.81. eCollection 2016.
D'Costa et al., Practical utilization of recombinant AAV vector reference standards: focus on vector genomes titration by free ITR qPCR. Mol Ther Methods Clin Dev. Mar. 30, 2016;5:16019. doi: 10.1038/mtm.2016.19. eCollection 2016.
Dinculescu et al., AAV-Mediated Clarin-1 Expression in the Mouse Retina: Implications for USH3A Gene Therapy. PLoS One. Feb. 16, 2016;11(2):e0148874. doi: 10.1371/journal.pone.0148874. eCollection 2016.
Duan, Systemic AAV Micro-dystrophin Gene Therapy for Duchenne Muscular Dystrophy. Mol Ther. Oct. 3, 2018;26(10):2337-2356. doi: 10.1016/j.ymthe.2018.07.011. Epub Jul. 17, 2018.
Eichler et al., Hematopoietic Stem-Cell Gene Therapy for Cerebral Adrenoleukodystrophy. N Engl J Med. Oct. 26, 2017;377(17):1630-1638. doi: 10.1056/NEJMoa1700554. Epub Oct. 4, 2017.
Gong et al., Adenoassociated virus serotype 9-mediated gene therapy for X-linked adrenoleukodystrophy. Mol Ther. May 2015;23(5):824-834. doi: 10.1038/mt.2015.6. Epub Jan. 16, 2015.
Gray et al., Directed evolution of a novel adeno-associated virus (AAV) vector that crosses the seizure-compromised blood-brain barrier (BBB). Mol Ther. Mar. 2010;18(3):570-8. doi: 10.1038/mt.2009.292. Epub Dec. 29, 2009.
Gray et al., Vector design and considerations for CNS applications. Gene Vector Design and Application to Treat Nervous System Disorders. Gene Therapy Center at the University of North Carolina at Chapel Hill. 2011. pp. 9-15.
Griciuc et al., Alzheimer's disease risk gene CD33 inhibits microglial uptake of amyloid beta. Neuron. May 22, 2013;78(4):631-43. doi: 10.1016/j.neuron.2013.04.014. Epub Apr. 25, 2013.
Gyorgy et al., Gene Transfer with AAV9-PHP.B Rescues Hearing in a Mouse Model of Usher Syndrome 3A and Transduces Hair Cells in a Non-human Primate. Mol Ther Methods Clin Dev. Nov. 20, 2018;13:1-13. doi: 10.1016/j.omtm.2018.11.003. eCollection Jun. 14, 2019.
Hinderer et al., Severe Toxicity in Nonhuman Primates and Piglets Following High-Dose Intravenous Administration of an Adeno-Associated Virus Vector Expressing Human SMN. Hum Gene Ther. Mar. 2018;29(3):285-298. doi: 10.1089/hum.2018.015. Epub Feb. 12, 2018.
Hordeaux et al., The GPI-Linked Protein LY6A Drives AAV-PHP.B Transport across the Blood-Brain Barrier. Mol Ther. May 8, 2019;27(5):912-921. doi: 10.1016/j.ymthe.2019.02.013. Epub Feb. 20, 2019.
Hudry et al., Exosome-associated AAV vector as a robust and convenient neuroscience tool. Gene Ther. Apr. 2016;23(4):380-92. doi: 10.1038/gt.2016.11. Epub Feb. 2, 2016.
Hughes et al., AAV9 intracerebroventricular gene therapy improves lifespan, locomotor function and pathology in a mouse model of Niemann-Pick type C1 disease. Hum Mol Genet. Sep. 1, 2018;27(17):3079-3098. doi: 10.1093/hmg/ddy212.
Isgrig et al., Gene Therapy Restores Balance and Auditory Functions in a Mouse Model of Usher Syndrome. Mol Ther. Mar. 1, 2017;25(3):780-791. doi: 10.1016/j.ymthe.2017.01.007. Epub Feb. 21, 2017.
Keskin et al., AAV5-miHTT Lowers Huntingtin mRNA and Protein without Off-Target Effects in Patient-Derived Neuronal Cultures and Astrocytes. Mol Ther Methods Clin Dev. Oct. 4, 2019;15:275-284. doi: 10.1016/j.omtm.2019.09.010. eCollection Dec. 13, 2019.
Koerber et al., Construction of diverse adeno-associated viral libraries for directed evolution of enhanced gene delivery vehicles. Nat Protoc. 2006;1(2):701-6. doi: 10.1038/nprot.2006.93.
Korbelin et al., Pulmonary Targeting of Adeno-associated Viral Vectors by Next-generation Sequencing-guided Screening of Random Capsid Displayed Peptide Libraries. Mol Ther. Jun. 2016;24(6):1050-1061. doi: 10.1038/mt.2016.62. Epub Mar. 28, 2016.
Leone et al., Long-term follow-up after gene therapy for canavan disease. Sci Transl Med. Dec. 19, 2012;4(165):165ra163. doi: 10.1126/scitranslmed.3003454.
Li et al., Engineering adeno-associated virus vectors for gene therapy. Nat Rev Genet. Apr. 2020;21(4):255-272. doi: 10.1038/s41576-019-0205-4. Epub Feb. 10, 2020.
Lopes et al., Gene Therapy for the Retinal Degeneration of Usher Syndrome Caused by Mutations in MYO7A. Cold Spring Harb Perspect Med. Jan. 20, 2015;5(6):a017319. doi: 10.1101/cshperspect.a017319.
Maguire et al., Microvesicle-associated AAV vector as a novel gene delivery system. Mol Ther. May 2012;20(5):960-71. doi: 10.1038/mt.2011.303. Epub Feb. 7, 2012.
Manno et al., Successful transduction of liver in hemophilia by AAV-Factor IX and limitations imposed by the host immune response. Nat Med. Mar. 2006;12(3):342-7. doi: 10.1038/nm1358. Epub Feb. 12, 2006.
Matsuzaki et al., Neurotropic Properties of AAV-PHP.B Are Shared among Diverse Inbred Strains of Mice. Mol Ther. Apr. 10, 2019;27(4):700-704. doi: 10.1016/j.ymthe.2019.02.016. Epub Feb. 28, 2019.
Mendell et al., Single-Dose Gene-Replacement Therapy for Spinal Muscular Atrophy. N Engl J Med. Nov. 2, 2017;377(18):1713-1722. doi: 10.1056/NEJMoa1706198.
Millington-Ward et al., Suppression and replacement gene therapy for autosomal dominant disease in a murine model of dominant retinitis pigmentosa. Mol Ther. Apr. 2011;19(4):642-9. doi: 10.1038/mt.2010.293. Epub Jan. 11, 2011.
Mookherjee et al., Long-term rescue of cone photoreceptor degeneration in retinitis pigmentosa 2 (RP2)-knockout mice by gene replacement therapy. Hum Mol Genet. Nov. 15, 2015;24(22):6446-58. doi: 10.1093/hmg/ddv354. Epub Sep. 10, 2015.
Nathwani, Gene therapy for hemophilia. Hematology Am Soc Hematol Educ Program. Dec. 6, 2019;2019(1):1-8. doi: 10.1182/hematology.2019000007.
Nist-Lund et al., Improved TMC1 gene therapy restores hearing and balance in mice with genetic inner ear disorders. Nat Commun. Jan. 22, 2019;10(1):236. doi: 10.1038/s41467-018-08264-w.
Nonnenmacher et al., High capsid-genome correlation facilitates creation of AAV libraries for directed evolution. Mol Ther. Apr. 2015;23(4):675-82. doi: 10.1038/mt.2015.3. Epub Jan. 14, 2015.
Park et al., Generation of transgenic marmosets expressing genetically encoded calcium indicators. Sci Rep. Oct. 11, 2016;6:34931. doi: 10.1038/srep34931.
Paulk et al., Bioengineered AAV Capsids with Combined High Human Liver Transduction In Vivo and Unique Humoral Seroreactivity. Mol Ther. Jan. 3, 2018;26(1):289-303. doi: 10.1016/j.ymthe.2017.09.021. Epub Sep. 25, 2017.
Paulk et al., Bioengineered Viral Platform for Intramuscular Passive Vaccine Delivery to Human Skeletal Muscle. Mol Ther Methods Clin Dev. Jul. 24, 2018;10:144-155. doi: 10.1016/j.omtm.2018.06.001. eCollection Sep. 21, 2018.
Pulicherla et al., Engineering liver-detargeted AAV9 vectors for cardiac and musculoskeletal gene transfer. Mol Ther. Jun. 2011;19(6):1070-8. doi: 10.1038/mt.2011.22. Epub Mar. 1, 2011.
Remes et al., AAV-mediated TIMP-1 overexpression in aortic tissue reduces the severity of allograft vasculopathy in mice. J Heart Lung Transplant. Apr. 2020;39(4):389-398. doi: 10.1016/j.healun.2020.01.1338. Epub Jan. 30, 2020.
Sallach et al., Tropism-modified AAV vectors overcome barriers to successful cutaneous therapy. Mol Ther. May 2014;22(5):929-39. doi: 10.1038/mt.2014.14. Epub Jan. 28, 2014.

(56) References Cited

OTHER PUBLICATIONS

Sasaki et al., Generation of transgenic non-human primates with germline transmission. Nature. May 28, 2009;459(7246):523-7. doi: 10.1038/nature08090.
Tan et al., AAV-ie enables safe and efficient gene transfer to inner ear cells. Nat Commun. Aug. 19, 2019;10(1):3733. doi: 10.1038/s41467-019-11687-8.
Tse et al., Structure-guided evolution of antigenically distinct adeno-associated virus variants for immune evasion. Proc Natl Acad Sci U S A. Jun. 13, 2017;114(24):E4812-E4821. doi: 10.1073/pnas.1704766114. Epub May 30, 2017.
Wan et al., Efficacy and Safety of rAAV2-ND4 Treatment for Leber's Hereditary Optic Neuropathy. Sci Rep. Feb. 19, 2016;6:21587. doi: 10.1038/srep21587.
Watters et al., Identification and dynamic regulation of tight junction protein expression in human neural stem cells. Stem Cells Dev. Jun. 15, 2015;24(12):1377-89. doi: 10.1089/scd.2014.0497.
Xu et al., A combination of mutations enhances the neurotropism of AAV-2. Virology. Oct. 25, 2005;341(2):203-14. doi: 10.1016/j.virol.2005.06.051. Epub Aug. 15, 2005.
Yang et al., Long-term outcomes of gene therapy for the treatment of Leber's hereditary optic neuropathy. EBioMedicine. Aug. 2016;10:258-68. doi: 10.1016/j.ebiom.2016.07.002. Epub Jul. 6, 2016.
Yu et al., Nrl knockdown by AAV-delivered CRISPR/Cas9 prevents retinal degeneration in mice. Nat Commun. Mar. 14, 2017;8:14716. doi: 10.1038/ncomms14716.
U.S. Appl. No. 17/046,487, filed Oct. 9, 2020, Maguire et al.
EP 19785415.1, Dec. 15, 2021, Extended European Search Report.
PCT/US2019/026852, Jul. 10, 2019, International Search Report and Written Opinion.
PCT/US2019/026852, Oct. 22, 2020, International Preliminary Report on Patentability.
PCT/US2021/050205, Dec. 20, 2021, International Search Report and Written Opinion.
U.S. Appl. No. 18/025,749, filed Mar. 10, 2023, Corey et al.
PCT/US2021/050205, Mar. 23, 2023, International Preliminary Report on Patentability.
PCT/US2022/026608, Nov. 9, 2023, International Preliminary Report on Patentability.
RU 2021131423, Dec. 21, 2023, Office Action.
JP 2021-557657, Mar. 5, 2024, Office Action.
U.S. Appl. No. 17/442,894, filed Sep. 24, 2021, Maguire et al.
EP 20779113.8, Nov. 23, 2022, Partial European Search Report.
EP 20779113.8, Apr. 18, 2023, Extended European Search Report.
PCT/US2022/026608, Aug. 15, 2022, Invitation to Pay Additional Fees.
PCT/US2022/026608, Oct. 12, 2022, International Search Report and Written Opinion.
PCT/US2020/025720, Jul. 27, 2020, International Search Report and Written Opinion.
PCT/US2020/025720, Oct. 7, 2021, International Preliminary Report on Patentability.
International Preliminary Report on Patentability for Application No. PCT/US2022/026608, mailed Nov. 9, 2023.
Japanese Office Action for Application No. 2021-557657, mailed Mar. 5, 2024.
Russian Office Action for Application No. 2021131423, mailed Dec. 21, 2023.
GenBank Submission; NCBI, Accession No. KU056473.1; Synthetic construct isolate PHP.B VP1 gene, partial cds. Deverman et al.; Jan. 4, 2016.
Körbelin et al., A brain microvasculature endothelial cell-specific viral vector with the potential to treat neurovascular and neurological diseases. EMBO Mol Med. Jun. 1, 2016;8(6):609-25. doi: 10.15252/emmm.201506078. Print Jun. 2016.
Kumar et al., Multiplexed Cre-dependent selection yields systemic AAVs for targeting distinct brain cell types. Nat Methods. May 2020;17(5):541-550. doi: 10.1038/s41592-020-0799-7. Epub Apr. 20, 2020.
Lang et al., Standard screening methods underreport AAV-mediated transduction and gene editing. Nat Commun. Jul. 30, 2019;10(1):3415. doi: 10.1038/s41467-019-11321-7.
Prabhakar et al., AAV9 transduction mediated by systemic delivery of vector via retro-orbital injection in newborn, neonatal and juvenile mice. Exp Anim. Nov. 10, 2021;70(4):450-458. doi: 10.1538/expanim.20-0186. Epub May 25, 2021.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

* cited by examiner

```
AAV9   QVATNHQSAQ-------AQAQTGWVQNQGI
AAV-S  QVATNHQSAQSTTLYSPAQAQTGWVQNQGI
PHP.B  QVATNHQSAQTLAVPFKAQAQTGWVQNQGI
```
(SEQ ID NOs: 20-22 from top to bottom)
FIG. 6A
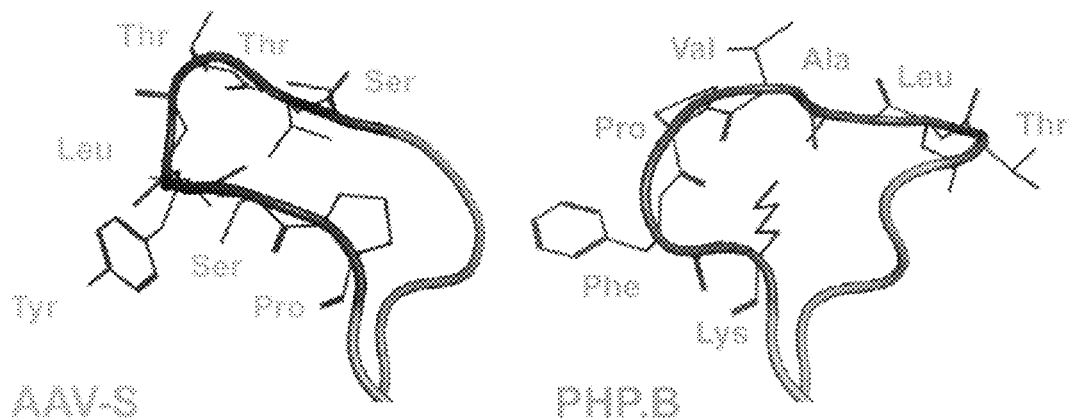
FIG. 6B
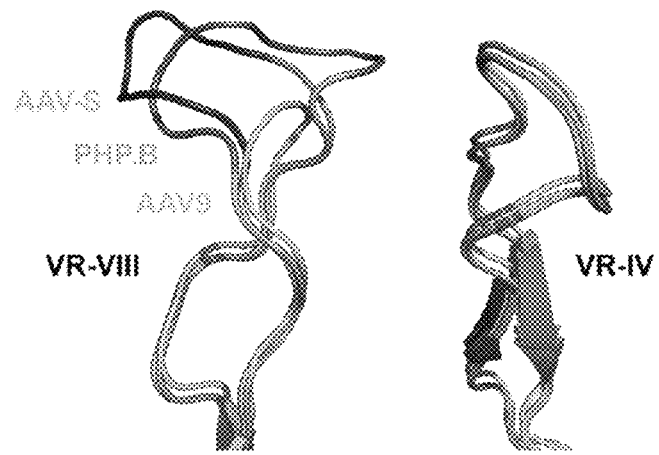
FIG. 6C

SEQUENCE LISTING

```
<160> NUMBER OF SEQ ID NOS: 24

<210> SEQ ID NO 1
<211> LENGTH: 736
<212> TYPE: PRT
<213> ORGANISM: Artificial Sequence
<220> FEATURE:
<223> OTHER INFORMATION: Synthetic

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
```

-continued

```
            225                 230                 235                 240
Thr Thr Ser Thr Arg Thr Trp Ala Leu Pro Thr Tyr Asn Asn His Leu
            245                 250                 255
Tyr Lys Gln Ile Ser Asn Ser Thr Ser Gly Ser Ser Asn Asp Asn
            260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                    325                 330                 335
Asn Leu Thr Ser Thr Val Gln Val Phe Thr Asp Ser Tyr Gln Leu
            340                 345                 350
Pro Tyr Val Leu Gly Ser Ala His Glu Gly Cys Leu Pro Phe Pro
            355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                    405                 410                 415
Phe Glu Asn Val Pro Phe His Ser Ser Tyr Ala His Ser Gln Ser Leu
                    420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                    485                 490                 495
Asn Asn Ser Glu Phe Ala Trp Pro Gly Ala Ser Ser Trp Ala Leu Asn
                    500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                    565                 570                 575
Tyr Gly Gln Val Ala Thr Asn His Gln Ser Ala Gln Ala Gln Ala Gln
                    580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
            610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                    645                 650                 655
```

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Ser Thr Thr Leu Tyr Ser Pro
1               5

<210> SEQ ID NO 3
<211> LENGTH: 743
<212> TYPE: PRT
<213> ORGANISM: Artificial Sequence
<220> FEATURE:
<223> OTHER INFORMATION: Synthetic

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser

-continued

```
            210                 215                 220
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                    260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                    325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ser Thr Thr Leu
                580                 585                 590

Tyr Ser Pro Ala Gln Ala Gln Thr Gly Trp Val Gln Asn Gln Gly Ile
                595                 600                 605

Leu Pro Gly Met Val Trp Gln Asp Arg Asp Val Tyr Leu Gln Gly Pro
610                 615                 620

Ile Trp Ala Lys Ile Pro His Thr Asp Gly Asn Phe His Pro Ser Pro
625                 630                 635                 640
```

```
Leu Met Gly Gly Phe Gly Met Lys His Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
                740

<210> SEQ ID NO 4
<211> LENGTH: 2229
<212> TYPE: DNA
<213> ORGANISM: Artificial Sequence
<220> FEATURE:
<223> OTHER INFORMATION: Synthetic

<400> SEQUENCE: 4
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaataccttg acccggcaa cggactcgac      180 aaggggagc cggtcaacgc agcagacgcg gcggccctcg agcacgacaa ggcctacgac      240
cagcagctca aggccggaga caacccgtac ctcaagtaca ccacgccga cgccgagttc      300 caggagcggc tcaaagaaga tacgtctttt gggggcaacc tcgggcgagc agtcttccag     360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
tcagtcccag accctcaacc aatcggagaa cctcccgcag cccctcagg tgtgggatct      600 cttacaatgg cttcaggtgg tggcgcacca gtggcagaca taacgaagg tgccgatgga     660 gtgggtagtt cctcgggaaa ttggcattgc gattcccaat ggctggggga cagagtcatc     720
accaccagca cccgaacctg ggccctgccc acctacaaca tcacctcta caagcaaatc     780 tccaacagca catctggagg atcttcaaat gacaacgcct acttcggcta cagcaccccc     840
tgggggtatt ttgacttcaa cagattccac tgccacttct caccacgtga ctggcagcga     900
ctcatcaaca caactgggg attccggcct aagcgactca acttcaagct cttcaacatt     960
caggtcaaag aggttacgga caacaatgga gtcaagacca cgccaataa ccttaccagc    1020 acggtccagg tcttcacgga ctcagactat cagctcccgt acgtgctcgg tcggctcac    1080 gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacataccct   1440
```

-continued

```
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct    1620 ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaatctact acgctttata gtcctgcaca ggcgcagacc    1800
ggctgggttc aaaaccaagg aatacttccg ggtatggttt ggcaggacag agatgtgtac    1860
ctgcaaggac ccatttgggc caaaattcct cacacgacg gcaactttca cccttctccg    1920
ctgatgggag ggtttggaat gaagcacccg cctcctcaga tcctcatcaa aaacacacct    1980
gtacctgcgg atcctccaac ggccttcaac aaggacaagc tgaactcttt catcacccag    2040
tattctactg gccaagtcag cgtggagatc gagtgggagc tgcagaagga aaacagcaag    2100
cgctggaacc cggagatcca gtacacttcc aactattaca agtctaataa tgttgaattt    2160
gctgttaata ctgaaggtgt atatagtgaa ccccgcccca ttggcaccag atacctgact    2220
cgtaatctg                                                            2229
```

<210> SEQ ID NO 5
<211> LENGTH: 232
<212> TYPE: PRT
<213> ORGANISM: Homo sapiens

<400> SEQUENCE: 5

```
Met Pro Ser Gln Gln Lys Lys Ile Ile Phe Cys Met Ala Gly Val Phe
1               5                   10                  15

Ser Phe Ala Cys Ala Leu Gly Val Val Thr Ala Leu Gly Thr Pro Leu
            20                  25                  30

Trp Ile Lys Ala Thr Val Leu Cys Lys Thr Gly Ala Leu Leu Val Asn
        35                  40                  45

Ala Ser Gly Gln Glu Leu Asp Lys Phe Met Gly Met Gln Tyr Gly
    50                  55                  60

Leu Phe His Gly Glu Gly Val Arg Gln Cys Gly Leu Gly Ala Arg Pro
65                  70                  75                  80

Phe Arg Phe Ser Phe Phe Pro Asp Leu Leu Lys Ala Ile Pro Val Ser
                85                  90                  95

Ile His Val Asn Val Ile Leu Phe Ser Ala Ile Leu Ile Val Leu Thr
            100                 105                 110

Met Val Gly Thr Ala Phe Phe Met Tyr Asn Ala Phe Gly Lys Pro Phe
        115                 120                 125

Glu Thr Leu His Gly Pro Leu Gly Leu Tyr Leu Leu Ser Phe Ile Ser
    130                 135                 140

Gly Ser Cys Gly Cys Leu Val Met Ile Leu Phe Ala Ser Glu Val Lys
145                 150                 155                 160

Ile His His Leu Ser Glu Lys Ile Ala Asn Tyr Lys Glu Gly Thr Tyr
                165                 170                 175

Val Tyr Lys Thr Gln Ser Glu Lys Tyr Thr Thr Ser Phe Trp Val Ile
            180                 185                 190

Phe Phe Cys Phe Phe Val His Phe Leu Asn Gly Leu Leu Ile Arg Leu
        195                 200                 205

Ala Gly Phe Gln Phe Pro Phe Ala Lys Ser Lys Asp Ala Glu Thr Thr
    210                 215                 220
```

Asn Val Ala Ala Asp Leu Met Tyr
225                 230

<210> SEQ ID NO 6
<211> LENGTH: 232
<212> TYPE: PRT
<213> ORGANISM: Homo sapiens

<400> SEQUENCE: 6

Met Pro Ser Gln Gln Lys Lys Ile Ile Phe Cys Met Ala Gly Val Phe
1               5                   10                  15

Ser Phe Ala Cys Ala Leu Gly Val Val Thr Ala Leu Gly Thr Pro Leu
            20                  25                  30

Trp Ile Lys Ala Thr Val Leu Cys Lys Thr Gly Ala Leu Leu Val Asn
        35                  40                  45

Ala Ser Gly Gln Glu Leu Asp Lys Phe Met Gly Glu Met Gln Tyr Gly
    50                  55                  60

Leu Phe His Gly Glu Gly Val Arg Gln Cys Gly Leu Gly Ala Arg Pro
65                  70                  75                  80

Phe Arg Phe Ser Phe Phe Pro Asp Leu Leu Lys Ala Ile Pro Val Ser
                85                  90                  95

Ile His Val Asn Val Ile Leu Phe Ser Ala Ile Leu Ile Val Leu Thr
            100                 105                 110

Met Val Gly Thr Ala Phe Phe Met Tyr Asn Ala Phe Gly Lys Pro Phe
        115                 120                 125

Glu Thr Leu His Gly Pro Leu Gly Leu Tyr Leu Leu Ser Phe Ile Ser
    130                 135                 140

Gly Ser Cys Gly Cys Leu Val Met Ile Leu Phe Ala Ser Glu Val Lys
145                 150                 155                 160

Ile His His Leu Ser Glu Lys Ile Ala Asn Tyr Lys Glu Gly Thr Tyr
                165                 170                 175

Val Tyr Lys Thr Gln Ser Glu Leu Tyr Thr Thr Ser Phe Trp Val Ile
            180                 185                 190

Phe Phe Cys Phe Phe Val His Phe Leu Asn Gly Leu Leu Ile Arg Leu
        195                 200                 205

Ala Gly Phe Gln Phe Pro Phe Ala Lys Ser Lys Asp Ala Glu Thr Thr
    210                 215                 220

Asn Val Ala Ala Asp Leu Met Tyr
225                 230

<210> SEQ ID NO 7
<211> LENGTH: 120
<212> TYPE: PRT
<213> ORGANISM: Homo sapiens

<400> SEQUENCE: 7

Met Gln Ala Leu Gln Gln Gln Pro Val Phe Pro Asp Leu Leu Lys Ala
1               5                   10                  15

Ile Pro Val Ser Ile His Val Asn Val Ile Leu Phe Ser Ala Ile Leu
            20                  25                  30

Ile Val Leu Thr Met Val Gly Thr Ala Phe Phe Met Tyr Asn Ala Phe
        35                  40                  45

Gly Lys Pro Phe Glu Thr Leu His Gly Pro Leu Gly Leu Tyr Leu Leu
    50                  55                  60

Ser Phe Ile Ser Gly Ser Cys Gly Cys Leu Val Met Ile Leu Phe Ala
65                  70                  75                  80

```
Ser Glu Val Lys Ile His His Leu Ser Glu Lys Ile Ala Asn Tyr Lys
                85                  90                  95

Glu Gly Thr Tyr Val Tyr Lys Thr Gln Ser Glu Lys Tyr Thr Thr Ser
            100                 105                 110

Phe Trp Leu Thr Lys Gly His Ser
            115                 120

<210> SEQ ID NO 8
<211> LENGTH: 245
<212> TYPE: PRT
<213> ORGANISM: Homo sapiens

<400> SEQUENCE: 8

Met Pro Ser Gln Gln Lys Lys Ile Ile Phe Cys Met Ala Gly Val Phe
1               5                   10                  15

Ser Phe Ala Cys Ala Leu Gly Val Val Thr Ala Leu Gly Thr Pro Leu
            20                  25                  30

Trp Ile Lys Ala Thr Val Leu Cys Lys Thr Gly Ala Leu Leu Val Asn
        35                  40                  45

Ala Ser Gly Gln Glu Leu Asp Lys Phe Met Gly Glu Met Gln Tyr Gly
    50                  55                  60

Leu Phe His Gly Glu Gly Val Arg Gln Cys Gly Leu Gly Ala Arg Pro
65                  70                  75                  80

Phe Arg Phe Ser Phe Phe Pro Asp Leu Leu Lys Ala Ile Pro Val Ser
                85                  90                  95

Ile His Val Asn Val Ile Leu Phe Ser Ala Ile Leu Ile Val Leu Thr
            100                 105                 110

Met Val Gly Thr Ala Phe Phe Met Tyr Asn Ala Phe Gly Lys Pro Phe
            115                 120                 125

Glu Thr Leu His Gly Pro Leu Gly Leu Tyr Leu Leu Ser Phe Ile Ser
            130                 135                 140

Val Ala Leu Trp Leu Pro Ala Thr Arg His Gln Ala Gln Gly Ser Cys
145                 150                 155                 160

Gly Cys Leu Val Met Ile Leu Phe Ala Ser Glu Val Lys Ile His His
                165                 170                 175

Leu Ser Glu Lys Ile Ala Asn Tyr Lys Glu Gly Thr Tyr Val Tyr Lys
            180                 185                 190

Thr Gln Ser Glu Lys Tyr Thr Thr Ser Phe Trp Val Ile Phe Cys
            195                 200                 205

Phe Phe Val His Phe Leu Asn Gly Leu Leu Ile Arg Leu Ala Gly Phe
            210                 215                 220

Gln Phe Pro Phe Ala Lys Ser Lys Asp Ala Glu Thr Thr Asn Val Ala
225                 230                 235                 240

Ala Asp Leu Met Tyr
            245

<210> SEQ ID NO 9
<211> LENGTH: 185
<212> TYPE: PRT
<213> ORGANISM: Artificial Sequence
<220> FEATURE:
<223> OTHER INFORMATION: Synthetic

<400> SEQUENCE: 9

Met Pro Ser Gln Gln Lys Lys Ile Ile Phe Cys Met Ala Gly Val Phe
1               5                   10                  15

Ser Phe Ala Cys Ala Leu Gly Val Val Thr Ala Leu Gly Thr Pro Leu
```

```
                    20                  25                  30
Trp Ile Lys Ala Thr Val Leu Cys Lys Thr Gly Ala Leu Leu Val Asn
            35                  40                  45

Ala Ser Gly Gln Glu Leu Asp Lys Phe Met Gly Glu Met Gln Tyr Gly
        50                  55                  60

Leu Phe His Gly Glu Gly Val Arg Gln Cys Gly Leu Gly Ala Arg Pro
65                  70                  75                  80

Phe Arg Phe Ser Cys Tyr Phe Leu Asp Pro Phe Met Gly Leu Pro Thr
                85                  90                  95

Gly Val Pro His Leu Leu Ser Leu Pro Cys Ser Thr Ser Cys Arg Arg
            100                 105                 110

Glu His Thr Ser Glu Arg Val Gln Glu Pro Ala Gly Cys Phe Ser Ala
        115                 120                 125

Val Arg Ser Lys Leu His Ala Gly Pro Ala Ala Thr Ser Phe Ser
    130                 135                 140

Arg Phe Ala Gln Ser Asn Pro Ser Glu His Pro Arg Gln Cys His Ser
145                 150                 155                 160

Leu Leu Cys His Pro Tyr Cys Val Asn His Gly Gly Asp Ser Leu Leu
                165                 170                 175

His Val Gln Cys Phe Trp Lys Thr Phe
            180                 185

<210> SEQ ID NO 10
<211> LENGTH: 699
<212> TYPE: DNA
<213> ORGANISM: Artificial Sequence
<220> FEATURE:
<223> OTHER INFORMATION: Synthetic

<400> SEQUENCE: 10
atgccaagcc aacagaagaa aatcattttt tgcatggccg gagtgttcag ttttgcatgt      60
gccctcggag ttgtgacagc cttggggaca ccgttgtgga tcaaagccac tgtcctctgc     120
aaaacgggag ctctgctcgt caatgcctca gggcaggagc tggacaagtt tatgggtgaa     180
atgcagtacg gcttttcca cggagagggt gtgaggcagt gtgggttggg agcaaggccc      240
tttcggttct catttttttcc agatttgctc aaagcaatcc cagtgagcat ccacgtcaat     300
gtcattctct ctctgccat ccttattgtg ttaaccatgg tggggacagc cttcttcatg       360
tacaatgctt ttggaaaacc ttttgaaact ctgcatggtc ccctagggct gtaccttttg     420
agcttcattt caggctcctg tggctgtctt gtcatgatat tgtttgcctc tgaagtgaaa     480
atccatcacc tctcagaaaa aattgcaaat tataaagaag ggactatgt ctacaaaacg       540 caaagtgaaa atataccac tcattctgg tcattttct tttgcttttt tgttcatttt         600
ctgaatgggc tcctaatacg acttgctgga tttcagttcc cttttgcaaa atctaaagac     660
gcagaaacaa ctaatgtagc tgcagatcta atgtactga                             699

<210> SEQ ID NO 11
<211> LENGTH: 250
<212> TYPE: PRT
<213> ORGANISM: Mus musculus

<400> SEQUENCE: 11

Met Pro Ser Gln Gln Lys Lys Ile Ile Phe Cys Met Ala Gly Val Leu
1               5                   10                  15

Ser Phe Leu Cys Ala Leu Gly Val Val Thr Ala Val Gly Thr Pro Leu
            20                  25                  30
```

```
Trp Val Lys Ala Thr Ile Leu Cys Lys Thr Gly Ala Leu Leu Val Asn
    35                  40                  45

Ala Ser Gly Lys Glu Leu Asp Lys Phe Met Gly Glu Met Gln Tyr Gly
    50                  55                  60

Leu Phe His Gly Glu Gly Val Arg Gln Cys Gly Leu Gly Ala Arg Pro
65                  70                  75                  80

Phe Arg Phe Ser Ser Arg Ser Met Lys Glu Arg Tyr Ser Leu Tyr Glu
                85                  90                  95

Asp Lys Gly Glu Thr Ala Val Phe Pro Asp Leu Val Gln Ala Ile Pro
                100                 105                 110

Val Ser Ile His Ile Asn Ile Ile Leu Phe Ser Met Ile Leu Val Val
                115                 120                 125

Leu Thr Met Val Gly Thr Ala Phe Phe Met Tyr Asn Ala Phe Gly Lys
    130                 135                 140

Pro Phe Glu Thr Leu His Gly Pro Leu Gly Leu Tyr Leu Val Ser Phe
145                 150                 155                 160

Ile Ser Gly Ser Cys Gly Cys Leu Val Met Ile Leu Phe Ala Ser Glu
                165                 170                 175

Val Lys Val His Arg Leu Ser Glu Lys Ile Ala Asn Phe Lys Glu Gly
                180                 185                 190

Thr Tyr Ala Tyr Arg Thr Gln Asn Glu Asn Tyr Thr Thr Ser Phe Trp
    195                 200                 205

Val Val Phe Ile Cys Phe Phe Val His Phe Leu Asn Gly Leu Leu Ile
    210                 215                 220

Arg Leu Ala Gly Phe Gln Phe Pro Phe Thr Lys Ser Lys Glu Thr Glu
225                 230                 235                 240

Thr Thr Asn Val Ala Ser Asp Leu Met Tyr
                245                 250

<210> SEQ ID NO 12
<211> LENGTH: 232
<212> TYPE: PRT
<213> ORGANISM: Mus musculus

<400> SEQUENCE: 12

Met Pro Ser Gln Gln Lys Lys Ile Ile Phe Cys Met Ala Gly Val Leu
1               5                   10                  15

Ser Phe Leu Cys Ala Leu Gly Val Val Thr Ala Val Gly Thr Pro Leu
                20                  25                  30

Trp Val Lys Ala Thr Ile Leu Cys Lys Thr Gly Ala Leu Leu Val Asn
    35                  40                  45

Ala Ser Gly Lys Glu Leu Asp Lys Phe Met Gly Glu Met Gln Tyr Gly
    50                  55                  60

Leu Phe His Gly Glu Gly Val Arg Gln Cys Gly Leu Gly Ala Arg Pro
65                  70                  75                  80

Phe Arg Phe Ser Phe Pro Asp Leu Val Gln Ala Ile Pro Val Ser
                85                  90                  95

Ile His Ile Asn Ile Ile Leu Phe Ser Met Ile Leu Val Val Leu Thr
                100                 105                 110

Met Val Gly Thr Ala Phe Phe Met Tyr Asn Ala Phe Gly Lys Pro Phe
            115                 120                 125

Glu Thr Leu His Gly Pro Leu Gly Leu Tyr Leu Val Ser Phe Ile Ser
    130                 135                 140

Gly Ser Cys Gly Cys Leu Val Met Ile Leu Phe Ala Ser Glu Val Lys
```

```
                    145                 150                 155                 160
Val His Arg Leu Ser Glu Lys Ile Ala Asn Phe Lys Glu Gly Thr Tyr
                165                 170                 175

Ala Tyr Arg Thr Gln Asn Glu Asn Tyr Thr Thr Ser Phe Trp Val Val
                180                 185                 190

Phe Ile Cys Phe Phe Val His Phe Leu Asn Gly Leu Leu Ile Arg Leu
                195                 200                 205

Ala Gly Phe Gln Phe Pro Phe Thr Lys Ser Lys Glu Thr Glu Thr Thr
    210                 215                 220

Asn Val Ala Ser Asp Leu Met Tyr
225                 230

<210> SEQ ID NO 13
<211> LENGTH: 172
<212> TYPE: PRT
<213> ORGANISM: Mus musculus

<400> SEQUENCE: 13

Met Pro Ser Gln Gln Lys Lys Ile Ile Phe Cys Met Ala Gly Val Leu
1               5                   10                  15

Ser Phe Leu Cys Ala Leu Gly Val Val Thr Ala Val Gly Thr Pro Leu
                20                  25                  30

Trp Val Lys Ala Thr Ile Leu Cys Lys Thr Gly Ala Leu Leu Val Asn
            35                  40                  45

Ala Ser Gly Lys Glu Leu Asp Lys Phe Met Gly Glu Met Gln Tyr Gly
        50                  55                  60

Leu Phe His Gly Glu Gly Val Arg Gln Cys Gly Leu Gly Ala Arg Pro
65                  70                  75                  80

Phe Arg Phe Ser Cys Ser Cys Gly Cys Leu Val Met Ile Leu Phe Ala
                85                  90                  95

Ser Glu Val Lys Val His Arg Leu Ser Glu Lys Ile Ala Asn Phe Lys
                100                 105                 110

Glu Gly Thr Tyr Ala Tyr Arg Thr Gln Asn Glu Asn Tyr Thr Thr Ser
            115                 120                 125

Phe Trp Val Val Phe Ile Cys Phe Phe Val His Phe Leu Asn Gly Leu
        130                 135                 140

Leu Ile Arg Leu Ala Gly Phe Gln Phe Pro Phe Thr Lys Ser Lys Glu
145                 150                 155                 160

Thr Glu Thr Thr Asn Val Ala Ser Asp Leu Met Tyr
                165                 170

<210> SEQ ID NO 14
<211> LENGTH: 699
<212> TYPE: DNA
<213> ORGANISM: Artificial Sequence
<220> FEATURE:
<223> OTHER INFORMATION: Synthetic

<400> SEQUENCE: 14
atgccatctc aacaaaaaaa aataattttt tgcatggcag gggttctgtc ttttttgtgt      60
gcccttggag tcgtgactgc agttgggacc cccctgtggg tgaaagctac cattctctgc     120
aagacaggtg cttttgttgg taatgcctct ggtaaagaat tggacaagtt catgggtgaa     180
atgcaatacg gactcttcca tggggaaggc gtgagacagt gcggtttggg cgcacgcccc     240
ttccgattta gcttcttccc cgacctggtc caagccattc ccgtaagcat ccacataaac     300
ataatacttt tttctatgat tctcgttgtc ctgacaatgg tcggtacagc tttccttcatg    360
```

```
tataatgctt ttggcaaacc ctttgagaca ctccatggtc ccttgggcct gtatttggtt    420
tcattcatca gtggctcttg tggatgtttg gtaatgattc tgtttgcctc cgaggttaaa    480
gtccatcgac tgtcagaaaa aatagctaat ttcaaagaag gaacctatgc ctatcggact    540
cagaacgaaa attatacaac ctcattttgg gtagtattca tctgcttttt cgtgcatttt    600
cttaacggtc tgctcatcag acttgcaggt ttccagtttc catttacaaa aagcaaggag    660
accgaaacca ccaatgtggc tagtgacctc atgtactag                           699
```

<210> SEQ ID NO 15
<211> LENGTH: 232
<212> TYPE: PRT
<213> ORGANISM: Macaca fascicularis

<400> SEQUENCE: 15

```
Met Pro Ser Gln Gln Lys Lys Ile Ile Phe Cys Met Ala Gly Val Leu
1               5                   10                  15

Ser Phe Ala Cys Ala Leu Gly Val Val Thr Ala Leu Gly Thr Pro Leu
            20                  25                  30

Trp Ile Lys Ala Thr Ile Leu Cys Lys Thr Gly Ala Leu Leu Val Asn
        35                  40                  45

Ala Ser Gly Gln Glu Leu Asp Lys Phe Met Gly Met Gln Tyr Gly
    50                  55                  60

Leu Phe His Gly Glu Gly Val Arg Gln Cys Gly Leu Gly Ala Arg Pro
65                  70                  75                  80

Phe Arg Phe Ser Phe Phe Pro Asp Leu Leu Lys Ala Ile Pro Val Ser
                85                  90                  95

Ile His Val Asn Val Ile Leu Phe Ser Ala Ile Leu Ile Val Leu Thr
            100                 105                 110

Met Val Gly Thr Ala Phe Phe Met Tyr Asn Ala Phe Gly Lys Pro Phe
        115                 120                 125

Glu Thr Leu His Gly Pro Leu Gly Leu Tyr Leu Leu Ser Phe Ile Ser
    130                 135                 140

Gly Ser Cys Gly Cys Leu Val Met Ile Leu Phe Ala Ser Glu Val Lys
145                 150                 155                 160

Ile His His Leu Ser Glu Lys Ile Ala Asn Tyr Lys Glu Ala Thr Tyr
                165                 170                 175

Val Tyr Lys Thr Gln Ser Glu Lys Tyr Thr Thr Ser Phe Trp Val Val
            180                 185                 190

Phe Ile Cys Phe Phe Val His Phe Leu Asn Gly Leu Leu Ile Arg Leu
        195                 200                 205

Ala Gly Phe Gln Phe Pro Phe Ala Lys Ser Lys Asp Thr Glu Thr Thr
    210                 215                 220

Asn Val Ala Ala Asp Leu Met Tyr
225                 230
```

<210> SEQ ID NO 16
<211> LENGTH: 172
<212> TYPE: DNA
<213> ORGANISM: Mus musculus

<400> SEQUENCE: 16

```
agtgggtgag gaaggatgct tcacggactg gcgttctgcc tggtggaacc actgtaagga    60
agggcagtgt ttttcagctg ctgtgataaa tgcagccgac ggggcagtcg ctacttgatg   120
ctcacaaagg tctttgtttt caagtttgtc tttaccgaag ccttttctcg tc           172
```

<210> SEQ ID NO 17
<211> LENGTH: 2106
<212> TYPE: DNA
<213> ORGANISM: Mus musculus

<400> SEQUENCE: 17

| | | | | | |
|---|---|---|---|---|---|
| aaagcaaata | tcttcataat | ttctcaataa | ggatatggct | tcctttggcc | acttttaata | 60 |
| tgggtgattt | catctgtgca | tttagacttc | ttaagtacca | agccctcctt | atgttatgtt | 120 |
| tacagagcat | gtagtaagga | ttcaggctgg | aaaataacag | aagcaggagg | atggtttcac | 180 |
| tgggaagacg | ttcttcctga | tgggtaatgg | cctgcatagt | tagtccaaag | cagttggcta | 240 |
| gatggacgga | tggttactcc | atgtccttac | tgaccgataa | gatgcacgtt | ctcccaagca | 300 |
| gaactcaaca | ggcacatgac | atacagtttt | gtaagactcc | agggagcctt | aacttaccag | 360 |
| ggacccctg | agtggaccac | gtggagctgg | gatcaatgca | aaaagcaaga | ggaatttatt | 420 |
| gttccagtgc | actggggttg | tcccagatca | acagtgctgg | cagcgacccc | cagcaccttt | 480 |
| tcagtgagtt | tttatacggt | ttctaggggc | agaatagagc | atcagcaact | aggcacaata | 540 |
| tgattgatgg | aacagtgcac | cctttaaact | gattggtctt | taaggaatga | ggtgacaagg | 600 |
| acttccgttg | tctgatggtg | gaggtcctgt | ggagtgtgtc | cccacacaca | ggtcagttcc | 660 |
| tgtcctttag | tctgagaaat | gttaattagc | ctctcccttc | cagaggggga | cgtattccat | 720 |
| gaccttccca | aagttcttga | gctgacctat | tcagttaaat | aaaacagacg | ttatttctaa | 780 |
| ttgtccacat | agtcacagat | cccagaaaac | agaggtgaaa | ttggtgtctt | aaactgacag | 840 |
| tgcaccgaat | cattgcaaac | cttcaagttc | tttgtaagtt | tgcttagagc | atgatgtcat | 900 |
| tatgtctggt | ggtcaaaacc | agaaaagttt | ataagcaaac | aagcaagcta | gcaagaaagg | 960 |
| aagaaaaagg | aaaggaagaa | aggaagaaag | gaagaaagga | agaaaggaag | gaaggaagga | 1020 |
| aggaaggaag | gaaggaagga | aggaagacgg | aaagaagcag | atcaatggtt | tctttccta | 1080 |
| tgcatctgag | ttcataacaa | tggtacttac | agtggacaga | atccctacta | gacaagttgg | 1140 |
| tgagagaaac | ccactgggaa | ctgtttccag | cttggtgtct | ttggcactaa | tgagctccaa | 1200 |
| atcatgaaaa | ttcagaattg | aggtgggatt | gcagtgtgtc | atgggagaca | tgaagcatgg | 1260 |
| cccaagtcaa | atctttctcc | ttgaattatt | caccaaatga | atctgctgga | gaccagaggc | 1320 |
| cacaagtgag | cctgaaactg | acactcctta | actctcaatg | tgttaccctc | aggaaagaac | 1380 |
| aaaggacaaa | gacattatgg | tgccctggcc | acaaacacca | gagatcatag | agtttggaaa | 1440 |
| tgctccagaa | aaccaatctg | gaactaggaa | gatggctcag | ttgataaagg | gctgcctcaa | 1500 |
| aagcttgaga | gcctgagttc | agattcccca | gcacccatga | gaaacgcatg | ggtttcatac | 1560 |
| atgtctgtga | tccagcact | gggaaggcag | agctaggcaa | gtcttaaagc | tcaccagcaa | 1620 |
| gccaagtcaa | acctaatcag | tgcactccaa | ggtcagtgag | agaccctgac | tcaaaacaaa | 1680 |
| aaaacggagg | tgatggagaa | aggcaccatc | agcctccatg | aaccccctca | tgagcacaca | 1740 |
| cattttcatt | tgggaacaat | ttacatacaa | ggaaggagag | actgcacacc | tgaaatataa | 1800 |
| ccagctctgg | tgatggcctg | ctggttactc | tcagacatca | gaacatactt | gcttttctca | 1860 |
| ggatggagtc | ctttcacctt | aattcaggac | actggaagtt | tctagaagcc | caccagctag | 1920 |
| tctgtccagg | agctggtgca | tgctttggtg | atgggctagt | agtgccctga | cctggaggtc | 1980 |
| agaccctgaa | attctcaagc | acaaaaggct | gtgttaggag | ggaaagggag | ggagttgaag | 2040 |
| gctggaggat | gaatccccct | cctctggcct | ccatctacct | ctttcctctc | tgctcagagg | 2100 |

```
                                              tctgaa                                                        2106

<210> SEQ ID NO 18
<211> LENGTH: 7423
<212> TYPE: DNA
<213> ORGANISM: Artificial Sequence
<220> FEATURE:
<223> OTHER INFORMATION: Synthetic

<400> SEQUENCE: 18
gggggggggg ggggggggtt ggccactccc tctctgcgcg ctcgctcgct cactgaggcc        60
gggcgaccaa aggtcgcccg acgcccgggc tttgcccggg cggcctcagt gagcgagcga       120
gcgcgcagag agggagtggc caactccatc actaggggtt cctagatctg aattcggtac       180
cctagttatt aatagtaatc aattacgggg tcattagttc atagcccata tatggagttc       240
cgcgttacat aacttacggt aaatggcccg cctggctgac cgcccaacga ccccgccca       300
ttgacgtcaa taatgacgta tgttcccata gtaacgccaa tagggacttt ccattgacgt       360
caatgggtgg actatttacg gtaaactgcc cacttggcag tacatcaagt gtatcatatg       420
ccaagtacgc ccctattga cgtcaatgac ggtaaatggc ccgcctggca ttatgcccag       480
tacatgacct tatgggactt tcctacttgg cagtacatct acgtattagt catcgctatt       540
accatggtcg aggtgagccc cacgttctgc ttcactctcc ccatctcccc ccctcccca       600
ccccaattt tgtatttatt tattttttaa ttattttgtg cagcgatggg ggcggggggg       660
gggggggggc gcgcgccagg cggggcgggg cggggcgagg ggcggggcgg ggcgaggcgg       720
agaggtgcgg cggcagccaa tcagagcggc gcgctccgaa agtttccttt tatggcgagg       780
cggcggcggc ggcggcccta taaaaagcga agcgcgcggc gggcgggagt cgctgcgacg       840
ctgccttcgc cccgtgcccc gctccgccgc cgcctcgcgc cgcccgcccc ggctctgact       900
gaccgcgtta ctcccacagg tgagcgggcg gacggcccct tctcctccgg gctgtaatta       960
gcgcttggtt taatgacggc ttgtttcttt tctgtggctg cgtgaaagcc ttgagggggct      1020
ccgggagcta gagcctctgc taaccatgtt catgccttct tctttttcct acagctcctg      1080
ggcaacgtgc tggttattgt gctgtctcat cattttggca agaattcct cgaagatccg       1140
aaggggttca agcttaaaaa ctagtccgcg gaattctcga gctagcggcc gcagtgggtg      1200
aggaaggatg cttcacggac tggcgttctg cctggtggaa ccactgtaag gaagggcagt      1260
gtttttcagc tgctgtgata aatgcagccg acggggcagt cgctacttga tgctcacaaa      1320
ggtctttgtt ttcaagtttg tctttaccga agccttttct cgtcgccacc atgccatctc      1380
aacaaaaaaa aataattttt tgcatggcag gggttctgtc tttttttgtgt gcccttggag      1440
tcgtgactgc agttgggacc cccctgtggg tgaaagctac cattctctgc aagacaggtg      1500
ctttgttggt taatgcctct ggtaaagaat tggacaagtt catgggtgaa atgcaatacg      1560
gactcttcca tggggaaggc gtgagacagt gcgtttggg cgcacgcccc ttccgattta      1620
gcttcttccc cgacctggtc caagccattc ccgtaagcat ccacataaac ataatacttt      1680
tttctatgat tctcgttgtc ctgacaatgg tcggtacagc tttcttcatg tataatgctt      1740
ttggcaaacc ctttgagaca ctccatggtc ccttgggcct gtatttggtt tcattcatca      1800
gtggctcttg tggatgtttg gtaatgattc tgtttgcctc cgaggttaaa gtccatcgac      1860
tgtcagaaaa aatagctaat ttcaaagaag gaacctatgc ctatcggact cagaacgaaa      1920
attatacaac ctcatttttgg gtagtattca tctgcttttt cgtgcatttt cttaacggtc      1980
tgctcatcag acttgcaggt ttccagtttc catttacaaa aagcaaggag accgaaacca      2040
```

```
ccaatgtggc tagtgacctc atgtactaga aagcaaatat cttcataatt tctcaataag    2100
gatatggctt cctttggcca cttttaatat gggtgatttc atctgtgcat ttagacttct    2160
taagtaccaa gccctcctta tgttatgttt acagagcatg tagtaaggat tcaggctgga    2220
aaataacaga agcaggagga tggtttcact gggaagacgt tcttcctgat gggtaatggc    2280
ctgcatagtt agtccaaagc agttggctag atggacggat ggttactcca tgtccttact    2340
gaccgataag atgcacgttc tcccaagcag aactcaacag gcacatgaca tacagttttg    2400
taagactcca gggagcctta acttaccagg accccctga gtggaccacg tggagctggg    2460
atcaatgcaa aaagcaagag gaatttattg ttccagtgca ctggggttgt cccagatcaa    2520
cagtgctggc agcgaccccc agcacctttt cagtgagttt ttatacggtt tctaggggca    2580
gaatagagca tcagcaacta ggcacaatat gattgatgga acagtgcacc ctttaaactg    2640
attggtcttt aaggaatgag gtgacaagga cttccgttgt ctgatggtgg aggtcctgtg    2700
gagtgtgtcc ccacacacag gtcagttcct gtcctttagt ctgagaaatg ttaattagcc    2760
tctcccttcc agaggggac gtattccatg accttcccaa agttcttgag ctgacctatt     2820
cagttaaata aaacagacgt tatttctaat tgtccacata gtcacagatc ccagaaaaca    2880
gaggtgaaat tggtgtctta aactgacagt gcaccgaatc attgcaaacc ttcaagttct    2940
ttgtaagttt gcttagagca tgatgtcatt atgtctggtg gtcaaaacca gaaaagttta    3000
taagcaaaca agcaagctag caagaaagga agaaaaagga aaggaagaaa ggaagaaagg    3060
aagaaaggaa gaaaggaagg aaggaaggaa ggaaggaagg aaggaaggaa ggaagacgga    3120
aagaagcaga tcaatggttt cttttcctta tgcatctgagt tcataacaat ggtacttaca    3180
gtggacagaa tccctactag acaagttggt gagagaaacc cactgggaac tgtttccagc    3240
ttggtgtctt tggcactaat gagctccaaa tcatgaaaat tcagaattga ggtgggattg    3300
cagtgtgtca tgggagacat gaagcatggc ccaagtcaaa tctttctcct tgaattattc    3360
accaaatgaa tctgctggag accagaggcc acaagtgagc ctgaaactga cactccttaa    3420
ctctcaatgt gttaccctca ggaaagaaca aaggacaaag acattatggt gccctggcca    3480
caaacaccag agatcataga gtttggaaat gctccagaaa accaatctgg aactaggaag    3540
atggctcagt tgataaaggg ctgcctcaaa agcttgagag cctgagttca gattccccag    3600
cacccatgag aaacgcatgg gtttcataca tgtctgtgat cccagcactg ggaaggcaga    3660
gctaggcaag tcttaaagct caccagcaag ccaagtcaaa cctaatcagt gcactccaag    3720
gtcagtgaga gaccctgact caaaacaaaa aaacggaggt gatggagaaa ggcaccatca    3780
gcctccatga acccctcat gagcacacac attttcattt gggaacaatt tacatacaag     3840
gaaggagaga ctgcacacct gaaatataac cagctctggt gatggcctgc tggttactct    3900
cagacatcag aacatacttg cttttctcag gatggagtcc tttcacctta attcaggaca    3960
ctggaagttt ctagaagccc accagctagt ctgtccagga gctggtgcat gctttggtga    4020
tgggctagta gtgccctgac ctggaggtca gaccctgaaa ttctcaagca caaaggctg     4080 tgttaggagg gaaagggagg gagttgaagg ctggaggatg aatcccccctc ctctggcctc   4140 catctacctc tttcctctct gctcagaggt ctgaagtcga ctagagctcg ctgatcagcc    4200
tcgactgtgc cttctagttg ccagccatct gttgtttgcc cctcccccgt gccttccttg    4260
accctggaag gtgccactcc cactgtcctt tcctaataaa atgaggaaat tgcatcgcat    4320
tgtctgagta ggtgtcattc tattctgggg ggtggggtgg ggcaggacag caaggggag    4380
```

```
gattgggaag acaatagcag gcatgctggg gagagatcta ggaaccccta gtgatggagt    4440
tggccactcc ctctctgcgc gctcgctcgc tcactgaggc cgcccgggca aagcccgggc    4500
gtcgggcgac cttttggtcgc ccggcctcag tgagcgagcg agcgcgcaga gagggagtgg   4560
ccatgcagcc agctggcgta atagcgaaga ggcccgcacc gatcgccctt cccaacagtt    4620
gcgtagcctg aatggcgaat ggcgcgacgc gccctgtagc ggcgcattaa gcgcggcggg    4680
tgtggtggtt acgcgcagcg tgaccgctac acttgccagc gccctagcgc ccgctccttt    4740
cgctttcttc ccttcctttc tcgccacgtt cgccggcttt ccccgtcaag ctctaaatcg    4800
ggggctccct ttagggttcc gatttagtgc tttacggcac ctcgacccca aaaaacttga    4860
ttagggtgat ggttcacgta gtgggccatc gccctgatag acggtttttc gccctttgac    4920
gttggagtcc acgttcttta atagtggact cttgttccaa actggaacaa cactcaaccc    4980
tatctcggtc tattcttttg atttataagg gattttgccg atttcggcct attggttaaa    5040
aaatgagctg atttaacaaa aatttaacgc gaattttaac aaaatattaa cgtttacaat    5100
ttcctgatgc ggtattttct ccttacgcat ctgtgcggta tttcacaccg catatggtgc    5160
actctcagta caatctgctc tgatgccgca tagttaagcc agccccgaca cccgccaaca    5220
cccgctgacg cgccctgacg ggcttgtctg ctcccggcat ccgcttacag acaagctgtg    5280
accgtctccg ggagctgcat gtgtcagagg ttttcaccgt catcaccgaa acgcgcgaga    5340
cgaaagggcc tcgtgatacg cctattttta taggttaatg tcatgataat aatggtttct    5400
tagacgtcag gtggcacttt tcggggaaat gtgcgcggaa cccctatttg tttattttc    5460
taaatacatt caaatatgta tccgctcatg agacaataac cctgataaat gcttcaataa    5520
tattgaaaaa ggaagagtat gagtattcaa catttccgtg tcgcccttat cccttttttt    5580
gcggcatttt gccttcctgt ttttgctcac ccagaaacgc tggtgaaagt aaaagatgct    5640
gaagatcagt tgggtgcacg agtgggttac atcgaactgg atctcaacag cggtaagatc    5700
cttgagagtt ttcgccccga agaacgtttt ccaatgatga gcacttttaa agttctgcta    5760
tgtggcgcgg tattatcccg tattgacgcc gggcaagagc aactcggtcg ccgcatacac    5820
tattctcaga atgacttggt tgagtactca ccagtcacag aaaagcatct tacgatggc    5880
atgacagtaa gagaattatg cagtgctgcc ataaccatga gtgataacac tgcggccaac    5940
ttacttctga caacgatcgg aggaccgaag gagctaaccg cttttttgca acatggggg    6000
gatcatgtaa ctcgccttga tcgttgggaa ccggagctga atgaagccat accaaacgac    6060
gagcgtgaca ccacgatgcc tgtagcaatg gcaacaacgt tgcgcaaact attaactggc    6120
gaactactta ctctagcttc ccggcaacaa ttaatagact ggatggaggc ggataaagtt    6180
gcaggaccac ttctgcgctc ggcccttccg gctggctggt ttattgctga taaatctgga    6240
gccggtgagc gtgggtctcg cggtatcatt gcagcactgg ggccagatgg taagccctcc    6300
cgtatcgtag ttatctacac gacggggagt caggcaacta tggatgaacg aaatagacag    6360
atcgctgaga taggtgcctc actgattaag cattggtaac tgtcagacca agtttactca    6420
tatatacttt agattgattt aaaacttcat ttttaattta aaaggatcta ggtgaagatc    6480
ctttttgata atctcatgac caaaatccct taacgtgagt tttcgttcca ctgagcgtca    6540
gaccccgtag aaaagatcaa aggatcttct tgagatcctt ttttttctgcg cgtaatctgc    6600
tgcttgcaaa caaaaaaacc accgctacca gcggtggttt gtttgccgga tcaagagcta    6660
ccaactcttt ttccgaaggt aactggcttc agcagagcgc agataccaaa tactgtcctt    6720
ctagtgtagc cgtagttagg ccaccacttc aagaactctg tagcaccgcc tacatacctc    6780
```

```
gctctgctaa tcctgttacc agtggctgct gccagtggcg ataagtcgtg tcttaccggg      6840
ttggactcaa gacgatagtt accggataag gcgcagcggt cgggctgaac ggggggttcg      6900
tgcacacagc ccagcttgga gcgaacgacc tacaccgaac tgagatacct acagcgtgag      6960
cattgagaaa gcgccacgct tcccgaaggg agaaaggcgg acaggtatcc ggtaagcggc      7020
agggtcggaa caggagagcg cacgagggag cttccagggg gaaacgcctg gtatctttat      7080
agtcctgtcg ggtttcgcca cctctgactt gagcgtcgat ttttgtgatg ctcgtcaggg      7140
gggcggagcc tatggaaaaa cgccagcaac gcggcctttt tacggttcct ggccttttgc      7200
tggccttttg ctcacatgtt ctttcctgcg ttatcccctg attctgtgga taaccgtatt      7260
accgcctttg agtgagctga taccgctcgc cgcagccgaa cgaccgagcg cagcgagtca      7320
gtgagcgagg aagcggaaga gcgcccaata cgcaaaccgc ctctccccgc gcgttggccg      7380
attcattaat gcagctgggc tgcagggggg ggggggggg ggt                        7423

<210> SEQ ID NO 19
<211> LENGTH: 699
<212> TYPE: DNA
<213> ORGANISM: Homo sapiens

<400> SEQUENCE: 19
atgccaagcc aacagaagaa aatcattttt tgcatggccg gagtgttcag ttttgcatgt       60
gccctcggag ttgtgacagc cttggggaca ccgttgtgga tcaaagccac tgtcctctgc      120
aaaacgggag ctctgctcgt caatgcctca gggcaggagc tggacaagtt tatgggtgaa      180
atgcagtacg ggcttttcca cggagagggt gtgaggcagt gtgggttggg agcaaggccc      240
tttcggttct cattttttcc agatttgctc aaagcaatcc cagtgagcat ccacgtcaat      300
gtcattctct tctctgccat ccttattgtg ttaaccatgg tggggacagc cttcttcatg      360
tacaatgctt ttggaaaacc ttttgaaact ctgcatggtc ccctagggct gtaccttttg      420
agcttcattt caggctcctg tggctgtctt gtcatgatat tgtttgcctc tgaagtgaaa      480
atccatcacc tctcagaaaa aattgcaaat tataaagaag ggactatgt ctacaaaacg      540 caaagtgaaa aatataccac ctcattctgg gtcattttct tttgcttttt tgttcatttt      600
ctgaatgggc tcctaatacg acttgctgga tttcagttcc cttttgcaaa atctaaagac      660
gcagaaacaa ctaatgtagc tgcagatcta atgtactga                             699

<210> SEQ ID NO 20
<211> LENGTH: 23
<212> TYPE: PRT
<213> ORGANISM: Artificial Sequence
<220> FEATURE:
<223> OTHER INFORMATION: Synthetic

<400> SEQUENCE: 20

Gln Val Ala Thr Asn His Gln Ser Ala Gln Ala Gln Ala Gln Thr Gly
1               5                   10                  15

Trp Val Gln Asn Gln Gly Ile
            20

<210> SEQ ID NO 21
<211> LENGTH: 30
<212> TYPE: PRT
<213> ORGANISM: Artificial Sequence
<220> FEATURE:
<223> OTHER INFORMATION: Synthetic
```

```
<400> SEQUENCE: 21

Gln Val Ala Thr Asn His Gln Ser Ala Gln Ser Thr Thr Leu Tyr Ser
1               5                   10                  15

Pro Ala Gln Ala Gln Thr Gly Trp Val Gln Asn Gln Gly Ile
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic

<400> SEQUENCE: 22

Gln Val Ala Thr Asn His Gln Ser Ala Gln Thr Leu Ala Val Pro Phe
1               5                   10                  15

Lys Ala Gln Ala Gln Thr Gly Trp Val Gln Asn Gln Gly Ile
            20                  25                  30

<210> SEQ ID NO 23
<211> LENGTH: 7
<212> TYPE: PRT
<213> ORGANISM: Artificial sequence
<220> FEATURE:
<223> OTHER INFORMATION: Synthetic

<400> SEQUENCE: 23

Thr Leu Ala Val Pro Phe Lys
1               5

<210> SEQ ID NO 24
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: NON_CONS
<222> LOCATION: (3)..(4)

<400> SEQUENCE: 24

Ser Thr Thr Ser
1
```

RECOMBINANT ADENO ASSOCIATED VIRUS ENCODING CLARIN-1 AND USES THEREOF

RELATED APPLICATIONS

This application claims priority under 35 U.S.C. § 119(e) to U.S. Provisional Application Ser. No. 63/180,537, filed Apr. 27, 2021, and to U.S. Provisional Application Ser. No. 63/078,319, filed Sep. 14, 2020, which claims priority under 35 U.S.C. § 119(a) to Canadian Patent Application No. 3,116,391, filed Apr. 27, 2021, each of which is incorporated herein by reference.

FEDERALLY SPONSORED RESEARCH

This invention was made with Government support under DC016932 awarded by the National Institutes of Health and DC017117 awarded by the National Institutes of Health. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 13, 2021, is named H082470374US02-SEQ-CHB and is 50,744 bytes in size.

BACKGROUND

Hearing loss, congenital or acquired, affects approximately 30 million people in the United States alone. Congenital hearing loss (e.g., Usher syndrome or nonsyndromic hearing loss and deafness) has an incidence of about 1:1,000 births, in which half or more have a defined genetic cause.

Because the cochlea and the retina are surgically accessible and are relatively immune-privileged environment, gene therapy using viral vectors is an attractive approach. At present, however, good AAV serotype that transduce all cochlear cells still remain to be identified. Significant challenges remain for clinical translation of AAV-based gene therapy for treating deafness.

SUMMARY

The present disclosure, at least in part, relates to compositions and methods useful for treating certain genetic diseases, for example, autosomal recessive disorder, etc. Autosomal recessive disorders (e.g., Usher Syndrome, type 3A) are disorders caused by abnormal expression or function of both alleles of a gene (e.g., CLRN1 gene). Adeno-associated virus (AAV) mediated gene therapy is one approach for the treatment of genetic diseases. Recombinant AAV (rAAV) has been developed to treat various genetic disorders, such as genetic hearing loss and/or vision loss (e.g., Usher Syndrome, type 3A).

In some aspects, the present disclosure provides a recombinant adeno-associated virus (rAAV), wherein the rAAV comprises: (i) an AAV-S capsid protein; and (ii) an isolated nucleic acid comprising two adeno-associated virus inverted terminal repeats (ITRs) flanking a transgene, wherein the transgene comprises a promoter operably linked to a nucleotide sequence encoding a clarin-1 protein. In some embodiments, the AAV-S capsid protein comprises an amino acid sequence at least 80% identical to SEQ ID NO: 3.

In some embodiments the clarin-1 protein is a human clarin-1 protein, a mouse clarin-1 protein, or a non-human primate clarin-1 protein. In some embodiments, the clarin-1 protein is a human clarin-1 protein. In some embodiments, the human clarin-1 protein comprises an amino acid sequence at least 80% identical to amino acid sequence of SEQ ID NO: 5-9. In some embodiments, the nucleic acid sequence encoding the human clarin-1 is at least 80% identical to a nucleotide sequence of SEQ ID NO: 10. In some embodiments, the clarin-1 protein is a mouse clarin-1 protein. In some embodiments, the mouse clarin-1 protein comprises an amino acid sequence at least 90% identical to amino acid sequence of SEQ ID NO: 11-13. In some embodiments, the nucleotide sequence encoding the mouse clarin-1 is codon optimized for expression in mouse. In some embodiments, the nucleotide sequence encoding the mouse clarin-1 comprises a nucleotide sequence at least 80% identical to SEQ ID NO: 14.

In some embodiments, the transgene further comprises a 5' untranslated region (5' UTR) and/or a 3' untranslated region (3' UTR) flanking the nucleotide sequence encoding the clarin-1 protein. In some embodiments, the 5' UTR and/or the 3'UTR are 5' UTR and/or 3' UTR of the CLRN gene. In some embodiments, the 5' UTR comprises a nucleotide sequence at least 80% identical to the nucleotide sequence of SEQ ID NO: 16. In some embodiments, the 3' UTR comprises a nucleotide sequence at least 80% identical to the nucleotide sequence of SEQ ID NO: 17.

In some embodiments, the promoter operably linked to the transgene is a constitutive promoter, an inducible promoter, or a tissue specific promoter. In some embodiments, the promoter is a chicken beta action (CBA) promoter, a CAG promoter, or a minimal promoter. In some embodiments, the minimal promoter is a minimal CMV promoter, a human EF1-α promoter, or a ProA6 promoter.

In some embodiments, the transgene further comprises an enhancer, an intron, and/or a Woodchuck Hepatitis Virus (WHP) Posttranscriptional Regulatory Element (WPRE).

In some embodiments, the AAV ITRs are ITRs of one or more serotypes selected from: AAV2, AAV3, AAV4, AAV5, and AAV6. In some embodiments, the AAV ITRs are AAV2 ITRs.

In some aspects, the present disclosure provides a recombinant adeno-associated virus comprising: (i) an AAV-S capsid protein; and (ii) an isolated nucleic acid comprising, from 5' to 3', (a) a 5' ITR; (b) a Human Cytomegalovirus Major Immediate-Early Enhancer (CMV IE enhancer); (c) a Chicken beta-actin (CBA) promoter; (d) a beta-actin exon; (e) a chimeric intron; (f) a 5' UTR; (g) a Kozak sequence; (h) a nucleotide sequence encoding a clarin-1 protein; (i) a 3' UTR; (j) a bovine growth hormone poly A signal; and (k) a 3' ITR.

In some embodiments, the AAV-S capsid protein has tropism for inner ear cells and/or cells of the eye. In some embodiments, the inner ear cell that can be transduced by AAV-S include outer hair cell (OHCs), inner hair cell (IHCs), supporting cell, spiral ganglion neuron, cells in piral limbus, inner and outer sulcus cells, cells in lateral wall, cells in stria vascularis, cells in inner sulcus, cells in spiral ligament, Claudius cells, cells in the Reissner's membrane, basilar membrane fibrocytes, fibrocytes in spiral ligament of the lateral wall, satellite glial cells, Schwann cells, or cells of the vestibular system. In some embodiments, the supporting cells are border cells, inner phalangeal cells, inner pillar cells, outer pillar cells, Deiters' cells, Hensen's cells, or Claudius cells. In some embodiments, the spiral limbus comprises glial cells or interdental cells. In some embodiments, the stria vascularis comprises basal cells and intermediate cells. In some embodiments, the spiral ligament comprises fibrocytes. In some embodiments, the eye cell comprises photoreceptor cells (PRs), cells of the outer plexiform layer (OPL), cells of the inner nuclear layer (INL), cells of the ganglion cell layer (GCL), cells of the inner plexiform layer (IPL), or retinal pigment epithelium (RPE) cells.

In some aspects, the present disclosure provides a host cell comprising the rAAV as described herein.

In some aspects, the present disclosure provides a pharmaceutical composition comprising the rAAV or the host as described herein. In some embodiments, the pharmaceutical composition further comprises a pharmaceutically acceptable carrier.

In some aspects, the present disclosure provides a method for treating hereditary hearing loss and/or vision loss (e.g., Usher syndrome, type 3A) in a subject in need thereof, the method comprising administering to the subject an effective amount of the rAAV, the host cell, or the pharmaceutical composition as described herein.

In some aspects, the present disclosure provides a method for treating a CLRN-associated disease in a subject in need thereof, the method comprising administering to the subject an effective amount of the rAAV, the host cell, or the pharmaceutical composition as described herein In some embodiments, the subject is a mammal. In some embodiments, the subject is human. In some embodiments, the subject is a non-human mammal. In some embodiments, the non-human mammal is a mouse. In some embodiments, the non-human mammal is a non-human primate. In some embodiments, the subject has a mutation in CLRN gene. In some embodiments, the subject is diagnosed with Usher syndrome, type 3A.

In some embodiments, the administration occurs by injection. In some embodiments, the injection is through the round window membrane of the inner ear, into a semicircular canal of the inner ear, or into the saccule or the utricle of the inner ear. In some embodiments, the administration results in delivery of the transgene (e.g., CLRN gene) to cells of the inner ear. In some embodiments, the administration results in delivery of the transgene to the cells in the eye.

In some aspects, the present disclosure also provides a kit comprising the rAAV or the pharmaceutical composition described herein.

The details of one or more embodiments of the invention are set forth in the description below. Other features or advantages of the present invention will be apparent from the following drawing and detailed description of certain embodiments, and also from the appended claims.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIGS. 1A-1B show representative images of cochlear sensory epithelium transduced with AAV-S (60× magnification). FIG. 1C shows transduction in the spiral limbus. FIG. 1D shows transduction in the lateral wall. Z and arrow indicate different layers of Z-stack. OHC: outer hair cells. IHC: inner hair cells. n=2 mice.

FIG. 2A show confocal images of the middle turn of non-human primates (NHP) cochlea, showing a lack of fluorescence in the uninjected ear. Hair cells were counterstained using a Myo7a antibody (1:200). FIG. 2B shows confocal images of the middle turn of NHP cochlea, showing robust fluorescence in many cell types in the injected ear. FIG. 2C shows images depicting the lateral wall, spiral limbus, and spiral ganglion region of the same transduced cochlea. IHCs, inner hair cells; OHCs, outer hair cells; PCs, pillar cells; SGN, spiral ganglion neurons. n=1 cochlea.

FIG. 3A shows results of auditory brainstem response (ABR) hearing tests; the click response is also displayed. FIG. 3B shows results of distortion product otoacoustic emission (DPOAE) tests performed on the same animals.

FIGS. 6A-6C show the AAV-S peptide is unlikely to distort capsid protein structure. FIG. 6A shows insertion point of AAV-S peptide in variable region VIII (VR-VIII) of the AAV9 capsid protein, with PHP.B insertion shown for comparison. FIG. 6B shows peptide loop of AAV-S and PHP.B inserts. The structure of AAV9 VP3 (PDB: 3UX1) was modified with AAV-S or PHP.B residues and modeled using SWISS-MODEL to assess likely conformations of variants. FIG. 6C shows AAV-S and PHP.B loops in the context of VR-VIII, with AAV9 inset, modeled by SWISS-MODEL. Insertion is not predicted to affect capsid protein structure outside of VR-VIII, including the nearby VR-IV.

FIG. 7A shows AAV eGFP vector. FIG. 7B shows AAV optimized CBA Clrn-1 vector (opti-Clrn1).

FIG. 8A shows schematic of the cochlea, with described regions numbered (see Table 1). Solid bars indicate the location of optical sections in the panels below. (FIGS. 8B, 8H, and 8J). Representative confocal images of whole-mount cochleas. C57BL/6J mice were injected via the round window membrane with AAV-S-CBA-EGFP at P1 with $3 \times 10^{10}$ VG, and the cochleas were dissected and mounted at P6 (n=8). FIG. 8B shows confocal images of the apical, middle, and basal regions of the organ of Corti. The upper panel shows EGFP expression; the middle panel shows anti-MYO7A labeling for inner and outer hair cells, and the lower panel is a merged image. FIGS. 8C-8D show cochlea immunostained with anti-NF-H. Nerve fibers of the apical, middle, and basal regions (FIG. 8C) and cell bodies of spiral ganglion neurons (FIG. 8D) were transduced with AAV-SCBA-EGFP (labeled with white asterisks). FIG. 8E shows transduced interdental cells and fibrocytes of the spiral limbus. FIG. 8F shows lateral wall, including EGFP-positive fibrocytes of the spiral ligament. FIG. 8G shows outer sulcus cells and Claudius cells. Phalloidin labels filamentous actin. FIG. 8H shows inner sulcus cells. FIG. 8I shows transduction efficiency in IHCs (left panel) and OHCs (right panel) in C57BL/6J mice injected AAV-S-CBA-EGFP at P1 with $3\times10^{10}$ VG. Bars indicate mean±SEM (n=8). FIG. 8J shows transduction by AAV-S-CBA-EGFP of hair cells and supporting cells in the macula of saccule; middle panels show anti-MYO7A labeling of hair cells. FIG. 8K shows auditory brainstem response (ABR) and distortion product otoacoustic emission (DPOAE) in wild-type C57BL/6J mice injected with $3\times10^{10}$ VG of AAV-S-CBA-EGFP at P1. ABR and a DPOAE tests were performed at P25 for vector-injected (n=3) and non-injected (dashed; n=3) animals. Bars indicate mean±SEM. Scale bars, FIG. 8B-8H 20 µm; FIG. 8J 40 µm.

FIG. 9A shows confocal images of the organ of Corti of the middle region of cochlea. The left panel shows eGFP expression, the middle panel shows an anti-MYO7A labeling and the right panel is merged. Inner hair cells were brightly labeled, while outer hair cells were faintly labeled. FIGS. 9B-9C show cochlea (middle region) immunostained with anti-NF-H to show SGN fibers. In adult mouse, nerve fibers show no transduction. FIG. 9C shows SGN cell bodies also show no transduction, but satellite glial cells and fibrocytes are transduced. FIG. 9D shows saccular macula, side view (left), Saccular macula, top view (right). FIG. 9E shows utriclar macula, side view (left), Utriclar macula, top view (right). The right-hand panels show a superposition of eGFP and MYO7A labels, along with phalloidin to mark actin of the hair bundles. The white arrow points to a transduced hair cell, and the white arrowhead points to an untransduced hair cell. Scale bars: 20 µm.

FIGS. 10A-10B show ABR and DPOAE thresholds at P35, P60, P90, P120, P150 of wild-type C57BL/6J mice (dashed; n=3-9) and TgAC1$^+$/ClrnKO mice, either untreated (n=3-6) or treated at P1 with AAV-S-optiClrn1 ($1.9\times10^{10}$ VG) (n=3-12). Untreated TgAC1$^+$/ClrnKO mice showed some residual auditory sensitivity at P35 that is largely absent by P60. Treated mice retain near-wild-type sensitivity at low and middle frequencies to at least P150. Error bars indicate mean±SEM. FIGS. 10C-10D shows representative scanning electron micrographs of hair bundles of the cochlea. All images were collected from the mid-cochlear region at P60 or P150. Wild-type C57BL/6J mice (n=3-4). Untreated TgAC1$^+$/ClrnKO mice (n=3-5). Mice treated at P1 with AAV-S-optiClrn1 ($1.9\times10^{10}$ VG) (n=3-4). Missing hair bundles were labeled with white asterisks; surviving but severely disorganized hair bundles are labeled with black asterisks; black arrow points to a loss of short-row stereocilia; white arrow points to a loss of middle-row and short-row stereocilia. Scale bars, upper panels 5 µm; middle and lower panel, 1 µm. FIG. 10E shows confocal images of OHC bundles at P90 labeled with phalloidin (light gray). Wild-type C57BL/6J mice (left panel, n=3). Untreated TgAC1$^+$/ClrnKO mice (middle panel, n=4). TgAC1$^+$/ClrnKO mice treated at P1 with AAV-S-optiClrn1 (right panel, n=3). Scale bar, 5 µm. Bundles are disorganized in untreated mutant animals and largely normal with treatment. FIG. 10F shows confocal images of the apical, middle, and basal regions of whole-mount cochleas at P90 immunostained with anti-MYO7A to label hair cells and anti-NF-H to label cochlear nerve fibers. Cochlear innervation is markedly reduced in untreated mutant animals (middle panel, n=4) and retained with treatment (right panel, n=3). Scale bar, 20 µm. FIG. 10G shows AAV-S-optiClrn1 delivery robustly and durably rescued hearing in the TgAC1$^+$/ClrnKO mouse model of Usher 3A. DPOAE amplitudes at frequency $2f_1-f_2$ ($f_1/f_2=1.20$) for $f_2=11.3$ kHz, of wild-type C57BL/6J mice (black dashed; n=3-9) and TgAC1$^+$/ClrnKO mice, untreated (n=3-6) or treated at P1 with AAV-S-optiClrn1n=3-12) at P35, P60, P90, P120, P150. Treated mice retain wild-type sensitivity at 11.3 kHz to at least P150. Bars indicate mean±S.E.M. FIG. 10H shows ABR and DPOAE testing of hearing in wild-type C57BL/6J mice injected with AAV-S expressing Clrn1 and controls. ABR and DPOAE in wild-type C57BL/6J mice injected at P1 with AAV-S-optiClrn1 ($3\times10^{10}$ VG). ABR and DPOAE assays were performed at P25 for both vector-injected (n=6) and non-injected (dashed; n=3) animals. Error bars indicate mean±S.E.M.

FIGS. 11A-11D show representative low-magnification images of frozen sections (18 µm thick) of the apical, middle, and basal regions of the cochlea. FIGS. 11A-11B show cochleas injected with $4.7\times10^{11}$ VG (n=2 ears). FIG. 11C shows cochlea injected with $8\times10^{10}$ VG (n=1 ear). FIG. 11D shows control ear injected with PBS (n=1 ear). In each, the right panel shows anti-EGFP labeling; the left panel also shows anti-MYO7A labeling and DAPI labeling superimposed to visualize hair cells and nuclei. FIG. 11E shows whole-mount images of the apical, middle, and basal regions of cochlea injected with $5.8\times10^{11}$ VG (n=1 ear). FIG. 11F shows summary schematic of AAV-S transduction in the cochlea. Specific regions are numbered (see Table 1). FIG. 11G shows transduction efficiency in IHCs and OHCs from apex to base in an NHP cochlea injected with $5.8\times10^{11}$ VG (n=1 ear) and $4.7\times10^{11}$ VG (n=2 ears) of AAV-S-CBA-EGFP. Error bars indicate mean±SEM. FIG. 11H shows frozen sections (18 µm thick) of the utricular macula and saccular macula in an inner ear injected through the RWM with $4.7\times10^{11}$ VG (n=2 ears). The upper panels show a superposition of EGFP and MYO7A labels, along with phalloidin to mark actin of the hair bundles. Scale bars, FIGS. 11A-11D 200 µm; FIG. 11E 30 µm; FIG. 11H 50 µm. FIG. 11I shows NHP organ of Corti injected with PBS control. High magnification images of frozen sections (18 µm thick) of apical, middle and basal regions of the organ of Corti in a cochlea injected with PBS. DAPI labels all nuclei, anti-MYO7A labels hair cells. Non-specific green fluorescence is negligible. Scale bar: 200 µm.

FIG. 12A show high-magnification images of frozen sections (18 µm thick) of the apical, middle, and basal regions of the organ of Corti in a cochlea injected with $4.7\times10^{11}$ VG (n=2 ears). The left panel shows AAV-S-transduced cells, labeled with an antibody to GFP; the middle panel shows hair cells labeled with an anti-MYO7A antibody, and the right panel shows both, along with DAPI labeling of nuclei. FIG. 12B shows schematic of the organ of Corti. Specific regions are numbered (see Table 1). FIG. 12C shows high-magnification images of a whole mount of a cochlea injected with $5.8\times10^{11}$ VG (n=1 ear). Top panel: AAV-S-CBA-EGFP transduces Hensen's and Claudius cells. Middle panel: AAV-S-CBA-EGFP transduces IHCs, OHCs, Deiters', and pillar cells. Bottom panel: AAV-S-CBA-EGFP transduces inner sulcus epithelial cells. FIG. 12D shows the lateral wall of a cochlea injected with a high dose of AAV-S-CBA-EGFP in an 18 µm frozen section. FIG. 12E shows the top view and side view of the spiral ligament, showing labeled fibrocytes. FIG. 12F shows high-magnification images of a frozen section of the utricular macula and saccular macula in an inner ear injected with $4.7 \times 10^{11}$ VG. EGFP colocalizes with anti-MYO7A labeling of hair cells, indicating that most hair cells were transduced (white). Scale bars, FIGS. 12A, 12D and 12E 200 µm; FIGS. 12C and 12F 30 µm.

FIG. 13A show spiral ganglion neurons (SGNs) innervating cochlear hair cells. FIG. 13B shows scarpa's ganglion neurons innervating vestibular hair cells. In NHPs, satellite glial cells and Schwann cells are transduced but apparently not neurons. Scale bar: 30 µm.

FIG. 14A shows Hematoxylin and eosin-stained sections of a NHP cochlea injected with $4.7 \times 10^{11}$ VG of AAV-S-CBA-GFP. Minimal focal perivascular mononuclear cell infiltration was observed (black arrows). FIG. 14B shows Hematoxylin and eosin stained sections of a NHP cochlea injected with PBS. Scale bars, 50 µm.

FIG. 15A shows saline injection control (n=1 ear). FIG. 15B shows low-dose AAV-S (n=1 ear). FIGS. 15C-15D show high-dose AAV-S (n=2 ears). Click ABR raw traces before and after injection. ABR thresholds in response to pure tones of 500, 1,000, 2,000, and 4,000 Hz and to clicks, before (solid) and after (dashed) injection. ABRs are plotted on an inverted scale as for human audiology, so hearing loss (higher threshold) is shown as down.

Figure 1A:
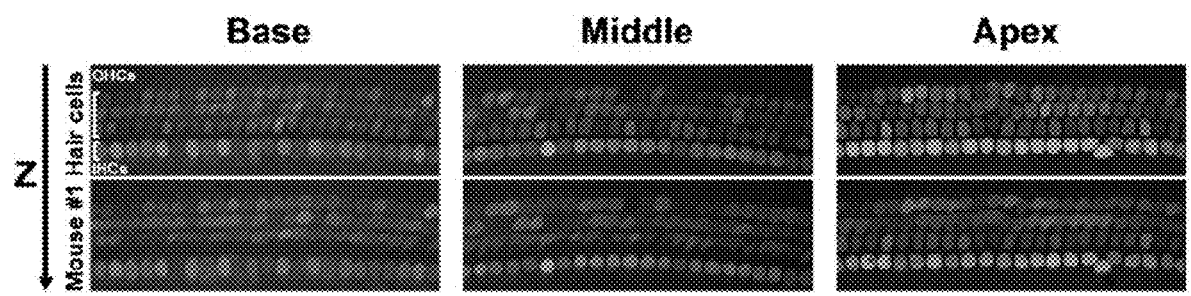
FIGS. 1A-1D show AAV-S GFP expression in neonatal mouse cochlea.

The accompanying drawings, which are incorporated in and constitute a part of this specification, illustrate certain embodiments, and together with the written description, serve to provide non-limiting examples of certain aspects of the compositions and methods disclosed herein.

DETAILED DESCRIPTION

The present disclosure, at least in part, relates to compositions and methods useful for treating certain genetic diseases, for example, autosomal recessive disorder associated with the CLRN gene (e.g., Usher Syndrome, Type 3A, etc.). Usher Syndrome, type 3A is caused by abnormal expression or loss of function of both alleles of CLRN1 gene. Adeno-associated virus (AAV) mediated gene therapy is one approach for the treatment of genetic diseases. Recombinant AAV (rAAV) has been developed to treat various genetic disorders, such as genetic hearing loss and/or vision loss (e.g., Usher Syndrome, type 3A). Because the cochlea and the retina are surgically accessible and maintain a relatively immune-privileged environment, gene therapy using viral vectors is an attractive approach. At present, however, there are no known AAV serotypes that transduce all cochlear and/or retina cells. Significant challenges remain for clinical translation of AAV-based gene therapy for hereditary hearing loss and/or vision loss (e.g., Usher syndrome, Type 3A).

The present disclosure, at least in part, relates to the unexpected finding of a capsid protein (e.g., AAV-S) that is capable of delivering a transgene to most cochlear cells (e.g., inner hair cells, outer hair cells, and fibrocytes) and cells in the eye (e.g., photoreceptors) across multiple species (e.g., mouse, rat, non-human primates, and human) and compositions thereof in the treatment of hereditary hearing loss and/or vision loss, for example, Usher syndrome type 3A. In some aspects, the present disclosure provides a recombinant adeno-associated virus (rAAV), wherein the rAAV comprises: (i) an AAV-S capsid protein; and (ii) an isolated nucleic acid comprising two adeno-associated virus inverted terminal repeats (ITRs) flanking a transgene, wherein the transgene comprises a promoter operably linked to a nucleotide sequence encoding a clarin-1 protein.

I. Recombinant Adeno-Associated Virus (rAAV)

In some aspects, the disclosure provides isolated and/or engineered AAVs. In some aspects, the present disclosure provides a recombinant adeno-associated virus (rAAV), wherein the rAAV comprises: (i) an AAV-S capsid protein; and (ii) an isolated nucleic acid comprising two adeno-associated virus inverted terminal repeats (ITRs) flanking a transgene, wherein the transgene comprises a promoter operably linked to a nucleotide sequence encoding a clarin-1 protein.

As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene (e.g., a transgene encoding a clarin-1 protein) of the rAAV will be delivered specifically to one or more predetermined tissue(s) or cell(s) (e.g., cochlear cells such as inner hair cells, outer hair cells, and fibrocytes, and/or cells in the eye such as photoreceptors).

The term "transgene," as used herein, refers to a gene that has been transferred by any of the known suitable genetic engineering techniques from one organism to another. The introduction of a transgene has the potential to change the phenotype of an organism. Transgene describes a segment of DNA containing a gene sequence that has been isolated from a first organism and is introduced into a second organism. This non-native segment of DNA may either retain the ability to produce RNA or protein in the transgenic organism or alter the normal function of the transgenic organism's genetic code.

(i) Capsid Protein

The AAV capsid is an important element in determining tissue-specific targeting capabilities of the virus. Thus, a rAAV having a capsid appropriate for the tissue being targeted can be selected. In some embodiments, the target tissue/cells of the present disclosure are cells of the ear. In some embodiments, the target tissue/cells of the present disclosure are cells of the eye.

Methods for obtaining recombinant AAVs having a desired capsid protein are well known in the art. (See, for example, US 2003-0138772, the contents of which are incorporated herein by reference). Typically the methods involve culturing a host cell which contains a nucleic acid sequence encoding an AAV capsid protein; a functional rep gene; a recombinant AAV vector comprising AAV inverted terminal repeats (ITRs) and an isolated nucleic acid comprising a transgene (e.g., a transgene for expressing a clarin-1 protein); and sufficient helper functions to permit packaging of the recombinant AAV vector into the AAV capsid.

In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are about 87 kDa, about 72 kDa, and about 62 kDa, respectively. In some embodiments, upon translation, capsid proteins form a spherical 60-mer protein shell around the viral genome. In some embodiments, the functions of the capsid proteins are to protect the viral genome, deliver the genome, and interact with the host. In some aspects, capsid proteins deliver the viral genome to a host in a tissue-specific or cell-specific manner (e.g., to cells in the ear and/or the eye).

The present disclosure is based on the finding that an exemplary AAV serotype capsid is capable of delivering a transgene (e.g., a transgene encoding the clarin-1 protein) to the ear (e.g., cochlear cells such as inner hair cells, outer hair cells, and fibrocytes) or the eye (e.g., retina cells such as photoreceptors). In some embodiments, an AAV capsid protein is of an AAV serotype selected from the group consisting of AAV9.PHP.B, AAV9.PHP.eB, exoAAV, Anc80, AAV1, AAV2, AAV2.7m8, AAV3, AAV4, AAV5, AAV6, AAV7, AAV8, AAVrh8, AAV9, AAV10, AAVrh10, and AAV-S. AAV2.7m8 is capable of delivering a transgene targeting cochlear hair cells and supporting cells of the cochlea, and the retina.

In some embodiments, the capsid protein is of AAV serotype 9 (AAV9). In some embodiments, an AAV capsid protein is of a serotype derived from AAV9 (e.g., an AAV9 capsid variant), for example, AAV9.PHP.B. In some embodiments, the AAV9 capsid variant is AAV9.PHP.B. In some embodiments, the AAV9 capsid variant comprises at least 4, e.g., 5, 6, or 7 contiguous amino acids inserted into the AAV9 capsid protein. In some embodiments, the AAV9 capsid variant comprises at least 4, e.g., 5, 6, or 7 contiguous amino acids inserted between amino acid 588 and 589 of any one of the AAV9 capsid protein. In some embodiments, the AAV9 capsid variant comprises 7 contiguous amino acids inserted between amino acid 588 and 589 of any one of the AAV9 capsid protein. In some embodiments, the AAV9 capsid variant comprises 7 contiguous amino acids inserted between amino acid 588 and 589 of any one of the AAV9 VP1 capsid protein. An exemplary amino acid sequence of AAV9 VP1 capsid protein is set forth in SEQ ID NO: 1:

MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVITTSTR

TWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLID

QYLYYLSKTINGSGQNQQTLKFSVAGPSNMAVQGRNYIPGPSYRQQRVS

TTVTQNNNSEFAWPGASSWALNGRNSLMNPGPAMASHKEGEDRFFPLSG

SLIFGKQGTGRDNVDADKVMITNEEEIKTTNPVATESYGQVATNHQSAQ

AQAQTGWVQNQGILPGMVWQDRDVYLQGPIWAKIPHTDGNFHPSPLMGG

FGMKHPPPQILIKNTPVPADPPTAFNKDKLNSFITQYSTGQVSVEIEWE

LQKENSKRWNPEIQYTSNYYKSNNVEFAVNTEGVYSEPRPIGTRYLTRN

L

In some embodiments, the seven (7) contiguous amino acids comprise the amino acid sequence: STTLYSP (SEQ ID NO: 2). In some embodiments, the AAV9 capsid variant is AAV-S. In some embodiments, the AAV9 capsid variant (e.g., AAV-S) comprises 7 contiguous amino acids (e.g., STTLYSP (SEQ ID NO: 2)) inserted between amino acid 588 and 589 of the AAV9 VP1 capsid protein. In some embodiments, the AAV9 capsid variant is AAV-S. In some embodiments, the capsid protein of the present disclosure comprises an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of AAV-S capsid protein as set forth in SEQ ID NO: 3. An exemplary amino acid sequence for AAV-S is set forth in SEQ ID NO: 3 (7 amino acid insertion underlined):

MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVITTSTR

TWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLID

QYLYYLSKTINGSGQNQQTLKFSVAGPSNMAVQGRNYIPGPSYRQQRVS

TTVTQNNNSEFAWPGASSWALNGRNSLMNPGPAMASHKEGEDRFFPLSG

SLIFGKQGTGRDNVDADKVMITNEEEIKTTNPVATESYGQVATNHQSAQ

<u>STTLYSP</u>AQAQTGWVQNQGILPGMVWQDRDVYLQGPIWAKIPHTDGNFH

PSPLMGGFGMKHPPPQILIKNTPVPADPPTAFNKDKLNSFITQYSTGQV

SVEIEWELQKENSKRWNPEIQYTSNYYKSNNVEFAVNTEGVYSEPRPIG

TRYLTRNL

In some embodiments, the present disclosure also uses a nucleotide sequence encoding the AAV-S capsid protein. In some embodiments, the nucleotide sequence encoding the AAV-S capsid protein comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to the nucleotide sequence of SEQ ID NO: 4. An exemplary nucleotide sequence encoding AAV-S capsid protein is set forth in SEQ ID NO: 4 (coding sequence for the 7 amino acid insertion underlined):

```
ATGGCTGCCGATGGTTATCTTCCAGATTGGCTCGAGGACAACCTTAGTG
AAGGAATTCGCGAGTGGTGGGCTTTGAAACCTGGAGCCCCTCAACCCAA
GGCAAATCAACAACATCAAGACAACGCTCGAGGTCTTGTGCTTCCGGGT
TACAAATACCTTGGACCCGGCAACGGACTCGACAAGGGGGAGCCGGTCA
ACGCAGCAGACGCGGCGGCCCTCGAGCACGACAAGGCCTACGACCAGCA
GCTCAAGGCCGGAGACAACCCGTACCTCAAGTACAACCACGCCGACGCC
GAGTTCCAGGAGCGGCTCAAAGAAGATACGTCTTTTGGGGGCAACCTCG
GGCGAGCAGTCTTCCAGGCCAAAAAGAGGCTTCTTGAACCTCTTGGTCT
GGTTGAGGAAGCGGCTAAGACGGCTCCTGGAAAGAAGAGGCCTGTAGAG
CAGTCTCCTCAGGAACCGGACTCCTCCGCGGGTATTGGCAAATCGGGTG
CACAGCCCGCTAAAAAGAGACTCAATTTCGGTCAGACTGGCGACACAGA
GTCAGTCCCAGACCCTCAACCAATCGGAGAACCTCCCGCAGCCCCCTCA
GGTGTGGGATCTCTTACAATGGCTTCAGGTGGTGGCGCACCAGTGGCAG
ACAATAACGAAGGTGCCGATGGAGTGGGTAGTTCCTCGGGAAATTGGCA
TTGCGATTCCCAATGGCTGGGGACAGAGTCATCACCACCAGCACCCGA
ACCTGGGCCCTGCCCACCTACAACAATCACCTCTACAAGCAAATCTCCA
ACAGCACATCTGGAGGATCTTCAAATGACAACGCCTACTTCGGCTACAG
CACCCCCTGGGGTATTTTGACTTCAACAGATTCCACTGCCACTTCTCA
CCACGTGACTGGCAGCGACTCATCAACAACAACTGGGGATTCCGGCCTA
AGCGACTCAACTTCAAGCTCTTCAACATTCAGGTCAAAGAGGTTACGGA
CAACAATGGAGTCAAGACCATCGCCAATAACCTTACCAGCACGGTCCAG
GTCTTCACGGACTCAGACTATCAGCTCCCGTACGTGCTCGGGTCGGCTC
ACGAGGGCTGCCTCCCGCCGTTCCCAGCGGACGTTTTCATGATTCCTCA
GTACGGGTATCTGACGCTTAATGATGGAAGCCAGGCCGTGGGTCGTTCG
TCCTTTTACTGCCTGGAATATTTCCCGTCGCAAATGCTAAGAACGGGTA
ACAACTTCCAGTTCAGCTACGAGTTTGAGAACGTACCTTTCCATAGCAG
CTACGCTCACAGCCAAAGCCTGGACCGACTAATGAATCCACTCATCGAC
CAATACTTGTACTATCTCTCAAAGACTATTAACGGTTCTGGACAGAATC
AACAAACGCTAAAATTCAGTGTGGCCGGACCCAGCAACATGGCTGTCCA
GGGAAGAAACTACATACCTGGACCCAGCTACCGACAACAACGTGTCTCA
ACCACTGTGACTCAAAACAACAACAGCGAATTTGCTTGGCCTGGAGCTT
CTTCTTGGGCTCTCAATGGACGTAATAGCTTGATGAATCCTGGACCTGC
TATGGCCAGCCACAAAGAAGGAGAGGACCGTTTCTTTCCTTTGTCTGGA
TCTTTAATTTTTGGCAAACAAGGAACTGGAAGAGACAACGTGGATGCGG
ACAAAGTCATGATAACCAACGAAGAAGAAATTAAAACTACTAACCCGGT
AGCAACGGAGTCCTATGGACAAGTGGCCACAAACCACCAGAGTGCCCAA
TCTACTACGCTTTATAGTCCTGCACAGGCGCAGACCGGCTGGGTTCAAA
ACCAAGGAATACTTCCGGGTATGGTTTGGCAGGACAGAGATGTGTACCT
GCAAGGACCCATTTGGGCCAAAATTCCTCACACGGACGGCAACTTTCAC
CCTTCTCCGCTGATGGGAGGGTTTGGAATGAAGCACCCGCCTCCTCAGA
TCCTCATCAAAAACACACCTGTACCTGCGGATCCTCCAACGGCCTTCAA
CAAGGACAAGCTGAACTCTTTCATCACCCAGTATTCTACTGGCCAAGTC
AGCGTGGAGATCGAGTGGGAGCTGCAGAAGGAAAACAGCAAGCGCTGGA
ACCCGGAGATCCAGTACACTTCCAACTATTACAAGTCTAATAATGTTGA
ATTTGCTGTTAATACTGAAGGTGTATATAGTGAACCCCGCCCCATTGGC
ACCAGATACCTGACTCGTAATCTG
```

AAV-S is an AAV9 capsid protein variant originally developed for targeting the central nervous system (CNS) (Hanlon et al., Selection of an Efficient AAV Vector for Robust CNS Transgene Expression, *Molecular Therapy Method & Clinical Development*, vol. 15, 320-332, Dec. 13, 2019). The present disclosure, at least in part, is based on the surprising discovery that AAV-S has good transducing efficiency for inner ear cells (e.g., inner hair cells, outer hair cells, and fibrocytes) and/or cells of the eye (e.g., retina cells, such as photoreceptors). In some embodiments, the AAV-S capsid protein is capable of transducing a wide variety of ear cells, including, but not limited to: outer hair cells (OHCs), inner hair cells (IHCs), supporting cells (e.g., border cells, inner phalangeal cells, inner pillar cells, outer pillar cells, Deiters' cells, Hensen's cells, or Claudius' cells), spiral ganglion neuron, spiral limbus cells (e.g., glial cell or interdental cell), inner and outer sulcus cells, cells of the lateral wall, cells of the stria vascularis (e.g., basal cell and intermediate cell), cells of the inner sulcus, cells of the spiral ligament (e.g., fibrocytes), or cells of the vestibular system. In some embodiments, the AAV-S capsid protein is capable of transducing a wide variety of eye cells, including, but not limited to, photoreceptor cells (e.g., rods and cones), cells of the outer plexiform layer (OPL), cells of the inner nuclear layer (INL), cells of the ganglion cell layer (GCL), cells of the inner plexiform layer (IPL), or retinal pigment epithelium (RPE) cells.

In other embodiments, the AAV capsid is an exoAAV. An exoAAV, refers to an exosome-associated AAV. An exoAAV capsid protein can be selected from the group consisting of AAV1, AAV2, AAV3, AAV4, AAV5, AAV6, AAV7, AAV8, AAVrh8, AAV9, AAV10, AAVrh10, and AAV.PHP.B. In some embodiments, the exoAAV is exoAAV1 or exoAAV9.

The skilled artisan will also realize that conservative amino acid substitutions may be made to provide functionally equivalent variants, or homologs, of the capsid proteins. In some aspects, the disclosure embraces sequence alterations that result in conservative amino acid substitutions in the capsid protein. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides (e.g., AAV-S capsid protein) disclosed herein.

(ii) Isolated Nucleic Acid

In some embodiments, the rAAV described herein comprises an isolated nucleic acid encoding a transgene (e.g., transgene for expressing a clarin-1 protein). In some embodiments, the isolated nucleic acid described herein is encapsulated by an AAV capsid (e.g., AAV-S capsid).

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified by, for example, cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated, but a nucleic acid sequence existing in its native state in its natural host is not. An isolated nucleic acid may be substantially purified but need not be. For example, a nucleic acid that is isolated within a cloning or expression vector is not pure in that it may comprise a tiny percentage of the material in the cell in which it resides. Such a nucleic acid is isolated, however, as the term is used herein because it is readily manipulatable by standard techniques known to those of ordinary skill in the art.

The isolated nucleic acids of the invention may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR). The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences (e.g., a promoter), and 5' and 3' AAV inverted terminal repeats (ITRs). The transgene may comprise, as disclosed elsewhere herein, a nucleotide sequence encoding a clarin-1 protein.

Aspects of the present disclosure relate to an isolated nucleic acid comprising a transgene encoding clarin-1. The CLRN1 gene encodes the clarin-1 protein. In some embodiments, the clarin-1 protein is a human clarin-1 protein. In some embodiments, the clarin-1 protein is a non-human primate clarin-1 protein.

Alternative splice forms of mouse clarin-1 protein have been identified. Isoform 2 of clarin-1, which includes exons 1, 3, and 4 of C/m gene, is the predominant isoform of clarin-1 expressed in the inner ear and eye (Zallocchi et al., Localization and expression of clarin-1, the Clrn1 gene product, in auditory hair cells and photoreceptors, *Hear Res.* 2009 September; 255(1-2): 109-120; Västinsalo H, et al. Alternative splice variants of the USH3A gene Clarin 1 (CLRN1). *Eur J Hum Genet.* 2011; 19(1):30-35; Dulon et al., Clarin-1 gene transfer rescues auditory synaptopathy in model of Usher syndrome, *J Clin Invest.* 2018; 128(8):3382-3401). Isoform 3 can also be expressed in the inner ear, but is thought to be non-functional due to the lack of a conserved transmembrane domain. Mouse clarin-1 isoform 1 has an amino acid sequence as set forth in NP_700433.1. Mouse clarin-1 isoform 2 has an amino acid sequence as set forth in NP_700434.1. Mouse clarin-1 isoform 3 has an amino acid sequence as set forth in NP_700435.1. Human clarin-1 isoform a has an amino acid sequence as set forth in NP_777367.1. Human clarin-1 isoform b, which is equivalent to mouse clarin-1 isoform 2, has an amino acid sequence as set forth in AAM88774.1. Human clarin-1 isoform c has an amino acid sequence as set forth in NP_443721.1. Human clarin-1 isoform d has an amino acid sequence as set forth in NP_001182723.1. Human clarin-1 isoform e has an amino acid sequence as set forth in NP_001243748.1.

In some embodiments, the transgene encodes human clarin-1 protein isoform a. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 5.

An exemplary amino acid sequence for human clarin-1 protein isoform a is set forth in SEQ ID NO: 5 (NP_777367.1):

```
MPSQQKKIIFCMAGVFSFACALGVVTALGTPLWIK

ATVLCKTGALLVNASGQELDKFMGEMQYGLFHGEG

VRQCGLGARPFRFSFFPDLLKAIPVSIHVNVILFS

AILIVLTMVGTAFFMYNAFGKPFETLHGPLGLYLL

SFISGSCGCLVMILFASEVKIHHLSEKIANYKEGT

YVYKTQSEKYTTSFWVIFFCFFVHFLNGLLIRLAG

FQFPPFAKSKDAETTNVAADLMY
```

In some embodiments, the transgene encodes human clarin-1 protein isoform b. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 6.

An exemplary amino acid sequence for human clarin-1 protein isoform b is set forth in SEQ ID NO: 6 (AAM88774.1):

```
MPSQQKKIIFCMAGVFSFACALGVVTALGTPLWIK

ATVLCKTGALLVNASGQELDKFMGEMQYGLFHGEG

VRQCGLGARPFRFSFFPDLLKAIPVSIHVNVILFS

AILIVLTMVGTAFFMYNAFGKPFETLHGPLGLYLL

SFISGSCGCLVMILFASEVKIHHLSEKIANYKEGT

YVYKTQSEKYTTSFWVIFFCFFVHFLNGLLIRLAG

FQFPPFAKSKDAETTNVAADLMY
```

In some embodiments, the transgene encodes human clarin-1 protein isoform c. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 7.

An exemplary amino acid sequence for human clarin-1 protein isoform c is set forth in SEQ ID NO: 7 (NP_443721.1):

```
MQALQQQPVFPDLLKAIPVSIHVNVILFSAILIVL

TMVGTAFFMYNAFGKPFETLHGPLGLYLLSFISGS

CGCLVMILFASEVKIHHLSEKIANYKEGTYVYKTQ

SEKYTTSFWLTKGHS
```

In some embodiments, the transgene encodes human clarin-1 protein isoform d. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 8.

An exemplary amino acid sequence for human clarin-1 protein isoform d is set forth in SEQ ID NO: 8 (NP_001182723.1):

```
MPSQQKKIIFCMAGVFSFACALGVVTALGTPLWIK

ATVLCKTGALLVNASGQELDKFMGEMQYGLFHGEG

VRQCGLGARPFRFSFFPDLLKAIPVSIHVNVILFS

AILIVLTMVGTAFFMYNAFGKPFETLHGPLGLYLL

SFISVALWLPATRHQAQGSCGCLVMILFASEVKIH

HLSEKIANYKEGTYVYKTQSEKYTTSFWVIFFCFF

VHFLNGLLIRLAGFQFPFAKSKDAETTNVAADLMY
```

In some embodiments, the transgene encodes human clarin-1 protein isoform e. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 9.

An exemplary amino acid sequence for human clarin-1 protein isoform e is set forth in SEQ ID NO: 9 (NP_001243748.1):

```
MPSQQKKIIFCMAGVFSFACALGVVTALGTPLWIK

ATVLCKTGALLVNASGQELDKFMGEMQYGLFHGEG

VRQCGLGARPFRFSCYFLDPFMGLPTGVPHLLSLP

CSTSCRREHTSERVQEPAGCFSAVRSKLHAGPAAA

TSFSRFAQSNPSEHPRQCHSLLCHPYCVNHGGDSL

LHVQCFWKTF
```

In some embodiments, the transgene encodes a human clarin-1 protein isoform a. In some embodiments, the transgene comprises a nucleotide sequence encoding the human clarin-1 protein isoform a. In some embodiments, the nucleotide sequence encoding human clarin-1 protein isoform b comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to the nucleotide sequence of SEQ ID NO: 19.

An exemplary nucleotide sequence encoding human clarin-1 protein isoform a is set forth in SEQ ID NO: 19:

```
ATGCCAAGCCAACAGAAGAAAATCATTTTTTGCAT

GGCCGGAGTGTTCAGTTTTGCATGTGCCCTCGGAG

TTGTGACAGCCTTGGGGACACCGTTGTGGATCAAA

GCCACTGTCCTCTGCAAAACGGGAGCTCTGCTCGT

CAATGCCTCAGGGCAGGAGCTGGACAAGTTTATGG

GTGAAATGCAGTACGGGCTTTTCCACGGAGAGGGT

GTGAGGCAGTGTGGGTTGGGAGCAAGGCCCTTTCG

GTTCTCATTTTTTCCAGATTTGCTCAAAGCAATCC

CAGTGAGCATCCACGTCAATGTCATTCTCTTCTCT

GCCATCCTTATTGTGTTAACCATGGTGGGGACAGC

CTTCTTCATGTACAATGCTTTTGGAAAACCTTTTG

AAACTCTGCATGGTCCCCTAGGGCTGTACCTTTTG

AGCTTCATTTCAGGCTCCTGTGGCTGTCTTGTCAT

GATATTGTTTGCCTCTGAAGTGAAAATCCATCACC

TCTCAGAAAAAATTGCAAATTATAAAGAAGGGACT

TATGTCTACAAAACGCAAAGTGAAAAATATACCAC

CTCATTCTGGGTCATTTTCTTTTGCTTTTTTGTTC

ATTTTCTGAATGGGCTCCTAATACGACTTGCTGGA

TTTCAGTTCCCTTTTGCAAAATCTAAAGACGCAGA

AACAACTAATGTAGCTGCAGATCTAATGTACTGA
```

In some embodiments, the transgene encodes a human clarin-1 protein isoform b. In some embodiments, the transgene comprises a nucleotide sequence encoding the human clarin-1 protein isoform b. In some embodiments, the nucleotide sequence encoding human clarin-1 protein isoform b comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to the nucleotide sequence of SEQ ID NO: 10.

An exemplary nucleotide sequence encoding human clarin-1 protein isoform b is set forth in SEQ ID NO: 10:

```
ATGCCAAGCCAACAGAAGAAAATCATTTTTTGCAT

GGCCGGAGTGTTCAGTTTTGCATGTGCCCTCGGAG

TTGTGACAGCCTTGGGGACACCGTTGTGGATCAAA

GCCACTGTCCTCTGCAAAACGGGAGCTCTGCTCGT

CAATGCCTCAGGGCAGGAGCTGGACAAGTTTATGG

GTGAAATGCAGTACGGGCTTTTCCACGGAGAGGGT

GTGAGGCAGTGTGGGTTGGGAGCAAGGCCCTTTCG

GTTCTCATTTTTTCCAGATTTGCTCAAAGCAATCC

CAGTGAGCATCCACGTCAATGTCATTCTCTTCTCT

GCCATCCTTATTGTGTTAACCATGGTGGGGACAGC
```

-continued

```
CTTCTTCATGTACAATGCTTTTGGAAAACCTTTTG

AAACTCTGCATGGTCCCCTAGGGCTGTACCTTTTG

AGCTTCATTTCAGGCTCCTGTGGCTGTCTTGTCAT

GATATTGTTTGCCTCTGAAGTGAAAATCCATCACC

TCTCAGAAAAATTGCAAATTATAAAGAAGGGACT

TATGTCTACAAAACGCAAAGTGAAAAATATACCAC

CTCATTCTGGGTCATTTTCTTTTGCTTTTTTGTTC

ATTTTCTGAATGGGCTCCTAATACGACTTGCTGGA

TTTCAGTTCCCTTTTGCAAAATCTAAAGACGCAGA

AACAACTAATGTAGCTGCAGATCTAATGTACTGA
```

In some embodiments, the transgene encodes mouse clarin-1 protein isoform 1. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 11.

An exemplary amino acid sequence for mouse clarin-1 protein isoform 1 is set forth in SEQ ID NO: 11 (NP_700433.1):

```
MPSQQKKIIFCMAGVLSFLCALGVVTAVGTPLWVK

ATILCKTGALLVNASGKELDKFMGEMQYGLFHGEG

VRQCGLGARPFRFSSRSMKERYSLYEDKGETAVFP

DLVQAIPVSIHINIILFSMILVVLTMVGTAFFMYN

AFGKPFETLHGPLGLYLVSFISGSCGCLVMILFAS

EVKVHRLSEKIANFKEGTYAYRTQNENYTTSFWVV

FICFFVHFLNGLLIRLAGFQFPFTKSKETETTNVA

SDLMY
```

In some embodiments, the transgene encodes mouse clarin-1 protein isoform 2. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 12.

An exemplary amino acid sequence for mouse clarin-1 protein isoform 2 is set forth in SEQ ID NO: 12 (NP_700434.1):

```
MPSQQKKIIFCMAGVLSFLCALGVVTAVGTPLWVK

ATILCKTGALLVNASGKELDKFMGEMQYGLFHGEG

VRQCGLGARPFRFSFFPDLVQAIPVSIHINIILFS

MILVVLTMVGTAFFMYNAFGKPFETLHGPLGLYLV

SFISGSCGCLVMILFASEVKVHRLSEKIANFKEGT

YAYRTQNENYTTSFWVVFICFFVHFLNGLLIRLAG

FQFPFTKSKETETTNVASDLMY
```

In some embodiments, the transgene encodes mouse clarin-1 protein isoform 3. In some embodiments, the transgene endonuclease a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 13.

An exemplary amino acid sequence for mouse clarin-1 protein isoform 3 is set forth in SEQ ID NO: 13 (NP_700435.1):

```
MPSQQKKIIFCMAGVLSFLCALGVVTAVGTPLWVK

ATILCKTGALLVNASGKELDKFMGEMQYGLFHGEG

VRQCGLGARPFRFSCSCGCLVMILFASEVKVHRLS

EKIANFKEGTYAYRTQNENYTTSFWVVFICFFVHF

LNGLLIRLAGFQFPFTKSKETETTNVASDLMY
```

In some embodiments, the transgene encodes a mouse clarin-1 protein isoform 2. In some embodiments, the transgene comprises a nucleotide sequence encoding the mouse clarin-1 protein isoform 2. In some embodiments, the nucleotide sequence encoding the clarin-1 protein is codon optimized for expression in mice. In some embodiments, the codon-optimized nucleotide sequence encoding mouse clarin-1 protein isoform 2 comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to the nucleotide sequence of SEQ ID NO: 14.

An exemplary codon-optimized nucleotide sequence encoding mouse clarin-1 protein isoform 2 is set forth in SEQ ID NO: 14.

```
ATGCCATCTCAACAAAAAAAAATAATTTTTTGCAT

GGCAGGGGTTCTGTCTTTTTTGTGTGCCCTTGGAG

TCGTGACTGCAGTTGGGACCCCCCTGTGGGTGAAA

GCTACCATTCTCTGCAAGACAGGTGCTTTGTTGGT

TAATGCCTCTGGTAAAGAATTGGACAAGTTCATGG

GTGAAATGCAATACGGACTCTTCCATGGGAAGGC

GTGAGACAGTGCGGTTTGGGCGCACGCCCCTTCCG

ATTTAGCTTCTTCCCCGACCTGGTCCAAGCCATTC

CCGTAAGCATCCACATAAACATAATACTTTTTTCT

ATGATTCTCGTTGTCCTGACAATGGTCGGTACAGC

TTTCTTCATGTATAATGCTTTTGGCAAACCCTTTG

AGACACTCCATGGTCCCTTGGGCCTGTATTTGGTT

TCATTCATCAGTGGCTCTTGTGGATGTTTGGTAAT
```

```
                    -continued
         GATTCTGTTTGCCTCCGAGGTTAAAGTCCATCGAC

TGTCAGAAAAAATAGCTAATTTCAAAGAAGGAACC

TATGCCTATCGGACTCAGAACGAAAATTATACAAC

CTCATTTTGGGTAGTATTCATCTGCTTTTTCGTGC

ATTTTCTTAACGGTCTGCTCATCAGACTTGCAGGT

TTCCAGTTTCCATTTACAAAAAGCAAGGAGACCGA

AACCACCAATGTGGCTAGTGACCTCATGTACTAG
```

In some embodiments, the transgene encodes non-human primate (e.g., cynomolgus monkey) clarin-1 protein. In some embodiments, the transgene encodes a clarin-1 protein having an amino acid sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to amino acid sequence of SEQ ID NO: 15.

An exemplary amino acid sequence for cynomolgus monkey clarin-1 protein is set forth in SEQ ID NO: 15:

```
         MPSQQKKIIFCMAGVLSFACALGVVTALGTPLWIK

ATILCKTGALLVNASGQELDKFMGEMQYGLFHGEG

VRQCGLGARPFRFSFFPDLLKAIPVSIHVNVILFS

AILIVLTMVGTAFFMYNAFGKPFETLHGPLGLYLL

SFISGSCGCLVMILFASEVKIHHLSEKIANYKEAT

YVYKTQSEKYTTSFWVVFICFFVHFLNGLLIRLAG

FQFPFAKSKDTETTNVAADLMY
```

Clarin-1 protein (e.g., mouse clarin-1 protein isoform 2, or a human clarin-1 protein isoform b) mediates hair cell and eye cell sensory neuron function (e.g., synaptic transmission), and is therefore useful in treating hereditary hearing loss and/or vision loss, for example, in Usher syndrome Type 3A. Generally, Usher syndrome refers to a condition characterized by partial or total hearing loss and vision loss that worsens over time. The hearing loss is classified as sensorineural, which means that it is caused by abnormalities of the inner ear. The loss of vision is caused by an eye disease called retinitis pigmentosa (RP), which affects the layer of light-sensitive tissue at the back of the eye (the retina). There are three major types of Usher syndrome, designated as types I, II, and III. These types are distinguished by the severity of hearing loss, the presence or absence of balance problems, and the age at which signs and symptoms appear. The types are further divided into subtypes based on their genetic cause. Usher Syndrome, Type 3A, is characterized by postlingual, progressive hearing loss, variable vestibular dysfunction, and onset of retinitis pigmentosa symptoms, including nyctalopia, constriction of the visual fields, and loss of central visual acuity, usually by the second decade of life. Usher Syndrome, Type 3A, is caused by mutations in CLRN1 encoding the clarin-1 protein.

An isolated nucleic acid sequence described herein (e.g., the isolated nucleic acid comprising a transgene encoding a clarin-1 protein) may further comprise a promoter operably linked to the coding sequence (e.g., nucleotide sequence encoding the clarin-1 protein). A "promoter" refers to a DNA sequence recognized by the synthetic machinery of the cell, or introduced synthetic machinery, required to initiate the specific transcription of a gene. The phrases "operatively linked," "under control," or "under transcriptional control" means that the promoter is in the correct location and orientation in relation to the nucleic acid to control RNA polymerase initiation and expression of the gene. A promoter may be a constitutive promoter, inducible promoter, or a tissue-specific promoter.

As used herein, a nucleotide sequence (e.g., a nucleotide sequence encoding a clarin-1 protein) and regulatory sequences are said to be operably linked when they are covalently linked in such a way as to place the expression or transcription of the nucleic acid sequence encoding clarin-1 protein under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence, and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide.

In some embodiments, the promoter is a constitutive promoter. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al., *Cell*, 41:521-530 (1985)), the SV40 promoter, the dihydrofolate reductase promoter, the β-actin promoter, the phosphoglycerol kinase (PGK) promoter, and the EF1-α promoter (Invitrogen). In some embodiments, the promoter is hybrid cytomegalovirus (CMV) immediate-early/Chicken beta-actin promoter (CAG promoter). In some embodiments, the promoter is a chicken beta-actin (CBA) promoter. In some embodiments, the promoter is a minimal promoter. A minimal promoter is a part of a promoter located between −35 to +35 region with respect to the transcription start site. It has one or more of 3 conservative sequences, i.e., Tata box, initiator region, binding site for RNA polymerase, and downstream promoter element. Exemplary minimal promoters can be less than 400, 400, 200, 195, 190, 185, 180, or less nucleotides in length. In some examples, the minimal promoter is a minimal CMV promoter. In some embodiments, the minimal promoter is a JeT promoter. In some embodiments, the minimal promoter is a human EF1-α core promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., *Proc. Natl. Acad. Sci. USA*, 93:3346-3351 (1996)), the tetracycline-repressible system (Gossen et al., *Proc. Natl. Acad. Sci. USA*, 89:5547-5551 (1992)), the tetracycline-inducible system (Gossen et al., *Science*, 268:1766-1769 (1995), see also Harvey et al., *Curr. Opin. Chem. Biol.*, 2:512-518 (1998)), the RU486-inducible system (Wang et al., *Nat. Biotech.*, 15:239-243 (1997) and Wang et al., *Gene Ther.*, 4:432-441 (1997)) and the rapamycin-inducible system (Magari et al., *J. Clin. Invest.*, 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene is used. The native promoter may be preferred when native expression of the transgene is desired. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites, or Kozak consensus sequences, may also be used to mimic the native expression. In some embodiments, the promoter is a native promoter. In some examples, the promoter can drive the transgene expression (e.g., clarin-1 protein) in the cells of the eye (e.g., photoreceptors such as rods and cones, horizontal cells, bipolar cells, and muller glias, etc.) (Angueyra et al., Leveraging Zebrafish to Study Retinal Degeneration, *Front Cell Dev Biol.* 2018; 6: 110). Non-limiting exemplary native promoters include a Methyl-CpG Binding Protein 2 (MeCP2) promoter, a Ubiquitin-C (UbiC) promoter, a Bestrophin 1 (Best1) (retina native) promoter, a human red opsin (RedO) promoter, a human rhodopsin kinase (RK) promoter, a mouse cone arrestin (CAR) promoter, a human rhodopsin (Rho) promoter, a UV opsin-specific 1 (opn1sw1) promoter, a UV opsin-specific 2 (opn1sw2) promoter, an Opsin 1, Medium Wave Sensitive 2 (opn1mw2) promoter, an opsin 1, long-wave-sensitive 1 (opn1lw1) promoter, a blue cone specific promoter (sws2), an L-opsin (opn1lw1-cxxc1) promoter, a thyroid hormone receptor β (thrb) promoter, an LIM Homeobox 1a (lhx1a) promoter, a connexin 55.5 (cx55.5) promoter, a metabotropic glutamate receptor 6b (grm6b), a glial fibrillar acidic protein (gfap) promoter, a cone transducin alpha subunit (gnat2) promoter, a connexin 52.7 (cx52.7) promoter, a connexin 52.9 (cx52.9) promoter, a heat shock cognate 70-kd protein,-like (hsp701) promoter, a yeast transcription activator protein-(GAL4-VP16) promoter, a upstream activation sequence (UAS), a visual system homeobox 1 (vsx1) promoter, or a rhodopsin (zop) promoter. In some embodiments, the promoter is a tissue specific promoter. In some embodiments, the promoter is a short photoreceptor-specific promoter. In some embodiments, the short photoreceptor-specific promoter is ProA6. In some embodiments, the promote is a native CLRN promoter.

In some embodiments, the regulatory sequences impart tissue-specific gene expression capabilities. In some cases, the tissue-specific regulatory sequences bind tissue-specific transcription factors that induce transcription in a tissue-specific manner. Such tissue-specific regulatory sequences (e.g., promoters, enhancers, etc.) are well known in the art. In some embodiments, the tissue-specific promoter is an eye-specific promoter. Examples of eye-specific promoters include, but are not limited to, a retinoschisin promoter, K12 promoter, a rhodopsin promoter, a rod-specific promoter, a cone-specific promoter, a rhodopsin kinase promoter, a GRK1 promoter, an interphotoreceptor retinoid-binding protein proximal (IRBP) promoter, and an opsin promoter (e.g., a red opsin promoter, a blue opsin promoter, etc.). In some embodiments, the tissue-specific promoter is an inner ear cell-specific promoter. Examples of inner ear cell-specific promoters include, but are not limited to, the Myosin 7 promoter, Myosin 15 promoter, and TMC1 promoter.

The 5' untranslated region (5' UTR) (also known as a leader sequence or leader RNA) is the region of an mRNA that is directly upstream from the initiation codon. The 5' UTR plays important roles in both transcriptional and translational regulation of the downstream gene (e.g., the CLRN1 gene). In some embodiments, a transgene (e.g., transgene for expressing a clarin-1 protein) comprises a nucleotide encoding a 5' UTR. In some embodiments, the 5' UTR is positioned between the promoter and the nucleotide sequence encoding the clarin-1 gene. In some embodiments, the 5' UTR is a native 5' UTR of the genomic CLRN1 gene. In some embodiments, the nucleotide sequence encoding the 5'UTR comprises a portion of a nucleotide sequence encoding a full-length CLRN1 gene 5' UTR. In some embodiments, the 5' UTR comprises at least 100 consecutive nucleotides, at least 200 consecutive nucleotides, at least 300 consecutive nucleotides, at least 400 consecutive nucleotides, at least 500 consecutive nucleotides, at least 600 consecutive nucleotides, at least 700 consecutive nucleotides, at least 800 consecutive nucleotides, at least 900 consecutive nucleotides, at least 1000 consecutive nucleotides, or more of a native full-length 5' UTR (e.g., the CLRN1 5' UTR). In some embodiments, the transgene comprises a nucleotide sequence encoding a 5' UTR having at least 80%, at least 85%, at least 90%, at least 91%, at least 92%, at least 93%, at least 94%, at least 95%, at least 96%, at least 97%, at least 98%, at least 99%, or 100% sequence identity to a nucleotide sequence encoding the CLRN1 gene 5' UTR as set forth in SEQ ID NO: 16). In some embodiments, an exemplary nucleotide sequence encoding the mouse Clrn1 gene 5' UTR is as set forth in SEQ ID NO: 16.

```
AGTGGGTGAGGAAGGATGCTTCACGGACTGGCGTT

CTGCCTGGTGGAACCACTGTAAGGAAGGGCAGTGT

TTTTCAGCTGCTGTGATAAATGCAGCCGACGGGGC

AGTCGCTACTTGATGCTCACAAAGGTCTTTGTTTT

CAAGTTTGTCTTTACCGAAGCCTTTTCTCGTC
```

The presence of an intron or intervening sequence in mRNA was first described, in vitro, to be important for mRNA processing and increased transgene expression (e.g., Huang Z M, Yen T S. Role of the hepatitis B virus post-transcriptional regulatory element in export of intron less transcripts. Mol Cell Biol. 1995; 15(7):3864-3869; Niwa M, Rose S D, Berget S M. In vitro polyadenylation is stimulated by the presence of an upstream intron. Genes Dev. 1990; 4(9):1552-1559, which are incorporated herein by reference). In some embodiments, an isolated nucleic acid described herein may also contain an artificial intron, desirably located between the promoter/enhancer sequence and the nucleotide sequence encoding a clarin-1 protein). In some embodiments, an intron is a synthetic or artificial (e.g., heterologous) intron. Examples of synthetic introns include an intron sequence derived from SV-40 (referred to as the SV-40 T intron sequence) and intron sequences derived from the chicken beta-actin gene. In some embodiments, a transgene described by the disclosure comprises one or more (1, 2, 3, 4, 5, or more) artificial introns. In some embodiments, the one or more artificial introns are positioned between a promoter and a nucleotide sequence encoding the transgene. In some embodiments, the isolated nucleic acid comprises a chimeric intron.

In some embodiments, the transgene (e.g., the transgene for expressing a clairn-1 protein) expression cassette further comprises a nucleotide sequence encoding a 3' UTR located 3' of the nucleotide sequence encoding the clarin-1 protein. In some embodiments, the 3' UTR is CLRN1 gene 3' UTR. In some embodiments, the nucleotide sequence encoding the 3' UTR have at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 17. An exemplary nucleotide sequence encoding mouse CLRN1 gene 3' UTR is set forth in SEQ ID NO: 17.

```
AAAGCAAATATCTTCATAATTTCTCAATAAGGATA

TGGCTTCCTTTGGCCACTTTTAATATGGGTGATTT

CATCTGTGCATTTAGACTTCTTAAGTACCAAGCCC

TCCTTATGTTATGTTTACAGAGCATGTAGTAAGGA

TTCAGGCTGGAAAATAACAGAAGCAGGAGGATGGT

TTCACTGGGAAGACGTTCTTCCTGATGGGTAATGG

CCTGCATAGTTAGTCCAAAGCAGTTGGCTAGATGG

ACGGATGGTTACTCCATGTCCTTACTGACCGATAA

GATGCACGTTCTCCCAAGCAGAACTCAACAGGCAC

ATGACATACAGTTTTGTAAGACTCCAGGGAGCCTT

AACTTACCAGGGACCCCCTGAGTGGACCACGTGGA

GCTGGGATCAATGCAAAAGCAAGAGGAATTTATT

GTTCCAGTGCACTGGGGTTGTCCCAGATCAACAGT

GCTGGCAGCGACCCCCAGCACCTTTTCAGTGAGTT

TTTATACGGTTTCTAGGGGCAGAATAGAGCATCAG

CAACTAGGCACAATATGATTGATGGAACAGTGCAC

CCTTTAAACTGATTGGTCTTTAAGGAATGAGGTGA

CAAGGACTTCCGTTGTCTGATGGTGGAGGTCCTGT

GGAGTGTGTCCCCACACACAGGTCAGTTCCTGTCC

TTTAGTCTGAGAAATGTTAATTAGCCTCTCCCTTC

CAGAGGGGACGTATTCCATGACCTTCCCAAAGTT

CTTGAGCTGACCTATTCAGTTAAATAAAACAGACG

TTATTTCTAATTGTCCACATAGTCACAGATCCCAG

AAAACAGAGGTGAAATTGGTGTCTTAAACTGACAG

TGCACCGAATCATTGCAAACCTTCAAGTTCTTTGT

AAGTTTGCTTAGAGCATGATGTCATTATGTCTGGT

GGTCAAAACCAGAAAAGTTTATAAGCAAACAAGCA

AGCTAGCAAGAAAGGAAGAAAAAGGAAAGGAAGAA

AGGAAGAAAGGAAGAAAGGAAGAAAGGAAGGAAGG

AAGGAAGGAAGGAAGGAAGGAAGGAAGGAAGACGG

AAAGAAGCAGATCAATGGTTTCTTTCCTTATGCAT

CTGAGTTCATAACAATGGTACTTACAGTGGACAGA

ATCCCTACTAGACAAGTTGGTGAGAGAAACCCACT

GGGAACTGTTTCCAGCTTGGTGTCTTTGGCACTAA

TGAGCTCCAAATCATGAAAATTCAGAATTGAGGTG

GGATTGCAGTGTGTCATGGGAGACATGAAGCATGG

CCCAAGTCAAATCTTTCTCCTTGAATTATTCACCA

AATGAATCTGCTGGAGACCAGAGGCCACAAGTGAG

CCTGAAACTGACACTCCTTAACTCTCAATGTGTTA

CCCTCAGGAAAGAACAAAGGACAAAGACATTATGG

TGCCCTGGCCACAAACACCAGAGATCATAGAGTTT

GGAAATGCTCCAGAAAACCAATCTGGAACTAGGAA

GATGGCTCAGTTGATAAAGGGCTGCCTCAAAAGCT

TGAGAGCCTGAGTTCAGATTCCCCAGCACCCATGA

GAAACGCATGGGTTTCATACATGTCTGTGATCCCA

GCACTGGGAAGGCAGAGCTAGGCAAGTCTTAAAGC

TCACCAGCAAGCCAAGTCAAACCTAATCAGTGCAC

TCCAAGGTCAGTGAGAGACCCTGACTCAAAACAAA

AAAACGGAGGTGATGGAGAAAGGCACCATCAGCCT

CCATGAACCCCTCATGAGCACACACATTTTCATT

TGGGAACAATTTACATACAAGGAAGGAGAGACTGC

ACACCTGAAATATAACCAGCTCTGGTGATGGCCTG

CTGGTTACTCTCAGACATCAGAACATACTTGCTTT

TCTCAGGATGGAGTCCTTTCACCTTAATTCAGGAC

ACTGGAAGTTTCTAGAAGCCCACCAGCTAGTCTGT

CCAGGAGCTGGTGCATGCTTTGGTGATGGGCTAGT

AGTGCCCTGACCTGGAGGTCAGACCCTGAAATTCT

CAAGCACAAAAGGCTGTGTTAGGAGGGAAAGGGAG

GGAGTTGAAGGCTGGAGGATGAATCCCCCTCCTCT

GGCCTCCATCTACCTCTTTCCTCTCTGCTCAGAGG

TCTGAA
```

Aspects of the disclosure relate to gene therapy vectors comprising an isolated nucleic acid as described herein. A gene therapy vector may be a viral vector (e.g., a lentiviral vector, an adeno-associated virus vector, an adenoviral (Ad) vector, etc.), a plasmid, a closed-ended DNA (e.g., ceDNA), a lipid/DNA nanoparticle, etc. In some embodiments, a gene therapy vector is a viral vector. In some embodiments, the transgene (e.g., the transgene for expressing the clarin-1 protein) is flanked by one or more viral replication sequences, for example, adeno-associated virus (AAV) inverted terminal repeats (ITRs).

The isolated nucleic acids of the disclosure may be recombinant adeno-associated virus (AAV) vectors (rAAV vectors). In some embodiments, an isolated nucleic acid as described by the disclosure comprises two adeno-associated virus (AAV) inverted terminal repeats (ITR), or variants thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene (e.g., transgene for expressing a clarin-1 protein), and 5' and 3' AAV inverted terminal repeats (ITRs). The isolated nucleic acids may also comprise a region encoding, for example, 5' and 3' untranslated regions (UTRs), and/or an expression control sequence (e.g., a poly-A tail).

Generally, ITR sequences are about 145 bp in length. Preferably, substantially the entire sequences encoding the ITRs are used in the isolated nucleic acid although some degree of minor modification of these sequences is permissible. The ability to modify these ITR sequences is within the skill of one in the art. (See, e.g., texts such as Sambrook et al., *Molecular Cloning. A Laboratory Manual*, 2d ed., Cold Spring Harbor Laboratory, New York (1989); and K. Fisher et al., *J. Virol.*, 70:520 532 (1996)). An example of such a molecule employed in the present invention is a "cis-acting" plasmid containing the transgene, in which the selected transgene sequence and associated regulatory elements are flanked by the 5' and 3"AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second AAV ITR is an AAV2 ITR. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR, or ΔITR). Without wishing to be bound by any particular theory, a rAAV vector comprising an ITR lacking a functional TRS produces a self-complementary rAAV vector, for example, as described by McCarthy (2008) Molecular Therapy 16(10):1648-1656. In some embodiments, the isolated nucleic acid comprises a 5' AAV2 ITR and a 3' AAV2 ITR.

In some embodiments, the isolated nucleic acid (e.g., rAAV vector) described herein comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70 (Hsp70 5'UTR). In some embodiments, the isolated nucleic acid (e.g., rAAV vector) comprises a woodchuck hepatitis virus posttranscriptional regulatory element (WPRE). In some embodiments, the isolated nucleic acid (e.g., rAAV vector) does not include a woodchuck hepatitis virus posttranscriptional regulatory element (WPRE).

In some embodiments, the vector further comprises conventional control elements which are operably linked with elements of the transgene in a manner that permits its transcription, translation, and/or expression in a cell transfected with the vector or infected with a virus produced using the vector. As used herein, "operably linked" sequences include both expression control sequences that are contiguous with the gene of interest and expression control sequences that act in trans or at a distance to control the gene of interest. Expression control sequences include appropriate transcription initiation, termination, promoter, and enhancer sequences; efficient RNA processing signals, such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product.

A polyadenylation sequence generally is inserted following the coding sequences and optionally before a 3' AAV ITR sequence. In some embodiments, the isolated nucleic acid described herein (e.g., rAAV vector) comprises a bovine growth hormone polyA signal (BGH polyA). A rAAV construct useful in the disclosure may also contain an intron, desirably located between the promoter/enhancer sequence and the transgene. One possible intron sequence is derived from SV-40, and is referred to as the SV-40 T intron sequence.

The present disclosure, at least in part, provides vectors (e.g., AAV vectors) for expressing a transgene (e.g., CLRN1), such vectors include AAV ITRs (e.g., AAV2 ITRs), and a transgene (e.g., transgene for expressing a clarin-1 protein). In some embodiments, the isolated nucleic acid (e.g., the rAAV vector) comprises, from 5' to 3', a 5' AAV ITR, a Human Cytomegalovirus Major Immediate-Early Enhancer (CMV IE enhancer), a promoter (e.g., chicken beta actin promoter), a beta-actin exon, a chimeric intron, a 5' UTR, a Kozak sequence, a nucleotide sequence encoding a clarin-1 protein, a 3' UTR, a bovine growth hormone poly A signal, and a 3' AAV ITR.

The present disclosure, at least in part, provides rAAV vectors for expressing a CLRN1, such vectors include AAV2 ITRs, and a transgene for expressing a clarin-1 protein. In some embodiments, the rAAV vector comprises, from 5' to 3', a 5' AAV ITR, a Human Cytomegalovirus Major Immediate-Early Enhancer (CMV IE enhancer), a CBA promoter, a beta-actin exon, a chimeric intron, a 5' UTR, a Kozak sequence, a nucleotide sequence encoding a clarin-1 protein (e.g., any one of the mouse or human clarin-1 protein known in the art), a 3' UTR, a bovine growth hormone poly A signal, and a 3' AAV ITR.

In some embodiment, the isolated nucleic acid (e.g., AAV vector) comprises a nucleic acid sequence at least 60%, at least 70%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 18. An exemplary AAV vector encoding a clarin-1 protein is set forth in SEQ ID NO: 18 (coding sequence for clarin-1 protein in bold face).

```
GGGGGGGGGGGGGGGGGGTTGGCCACTCCCTCTCTG
CGCGCTCGCTCGCTCACTGAGGCGGGCGACCAAA
GGTCGCCCGACGCCCGGGCTTTGCCCGGGCGGCCT
CAGTGAGCGAGCGAGCGCGCAGAGAGGGAGTGGCC
AACTCCATCACTAGGGGTTCCTAGATCTGAATTCG
GTACCCTAGTTATTAATAGTAATCAATTACGGGGT
CATTAGTTCATAGCCCATATATGGAGTTCCGCGTT
ACATAACTTACGGTAAATGGCCCGCCTGGCTGACC
GCCCAACGACCCCCGCCCATTGACGTCAATAATGA
CGTATGTTCCCATAGTAACGCCAATAGGGACTTTC
CATTGACGTCAATGGGTGGACTATTTACGGTAAAC
TGCCCACTTGGCAGTACATCAAGTGTATCATATGC
CAAGTACGCCCCCTATTGACGTCAATGACGGTAAA
TGGCCCGCCTGGCATTATGCCCAGTACATGACCTT
ATGGGACTTTCCTACTTGGCAGTACATCTACGTAT
TAGTCATCGCTATTACCATGGTCGAGGTGAGCCCC
ACGTTCTGCTTCACTCTCCCCATCTCCCCCCCCTC
CCCACCCCCAATTTTGTATTTATTTATTTTTAAT
TATTTTGTGCAGCGATGGGGCGGGGGGGGGGGG
GGGCGCGCGCCAGGCGGGGCGGGGCGGGGCGAGGG
GCGGGGCGGGGCGAGGCGGAGAGGTGCGGCGGCAG
CCAATCAGAGCGGCGCGCTCCGAAAGTTTCCTTTT
ATGGCGAGGCGGCGGCGGCGGCGGCCCTATAAAAA
GCGAAGCGCGCGGCGGGCGGGAGTCGCTGCGACGC
TGCCTTCGCCCCGTGCCCCGCTCCGCCGCCGCCTC
GCGCCGCCCGCCCCGGCTCTGACTGACCGCGTTAC
TCCCACAGGTGAGCGGGCGGGACGGCCCTTCTCCT
CCGGGCTGTAATTAGCGCTTGGTTTAATGACGGCT
TGTTTCTTTTCTGTGGCTGCGTGAAAGCCTTGAGG
GGCTCCGGGAGCTAGAGCCTCTGCTAACCATGTTC
ATGCCTTCTTCTTTTTCCTACAGCTCCTGGGCAAC
GTGCTGGTTATTGTGCTGTCTCATCATTTTGGCAA
AGAATTCCTCGAAGATCCGAAGGGGTTCAAGCTTA
AAAACTAGTCCGCGGAATTCTCGAGCTAGCGGCCG
CAGTGGGTGAGGAAGGATGCTTCACGGACTGGCGT
TCTGCCTGGTGGAACCACTGTAAGGAAGGGCAGTG
TTTTTCAGCTGCTGTGATAAATGCAGCCGACGGGG
CAGTCGCTACTTGATGCTCACAAAGGTCTTTGTTT
TCAAGTTTGTCTTTACCGAAGCCTTTTCTCGTCGC
CACCATGCCATCTCAACAAAAAAAATAATTTTTT
GCATGGCAGGGGTTCTGTCTTTTTTGTGTGCCCTT
GGAGTCGTGACTGCAGTTGGGACCCCCCTGTGGGT
GAAAGCTACCATTCTCTGCAAGACAGGTGCTTTGT
TGGTTAATGCCTCTGGTAAAGAATTGGACAAGTTC
ATGGGTGAAATGCAATACGGACTCTTCCATGGGA
AGGCGTGAGACAGTGCGGTTTGGGCGCACGCCCCT
TCCGATTAGCTTCTTCCCCGACCTGGTCCAAGCC
ATTCCCGTAAGCATCCACATAAACATAATACTTTT
TTCTATGATTCTCGTTGTCCTGACAATGGTCGGTA
CAGCTTTCTTCATGTATAATGCTTTTGGCAAACCC
TTTGAGACACTCCATGGTCCCTTGGGCCTGTATTT
GGTTTCATTCATCAGTGGCTCTTGTGGATGTTTGG
TAATGATTCTGTTTGCCTCCGAGGTTAAAGTCCAT
CGACTGTCAGAAAAAATAGCTAATTTCAAAGAAGG
AACCTATGCCTATCGGACTCAGAACGAAAATTATA
CAACCTCATTTTGGGTAGTATTCATCTGCTTTTTC
GTGCATTTTCTTAACGGTCTGCTCATCAGACTTGC
AGGTTTCCAGTTTCCATTTACAAAAAGCAAGGAGA
CCGAAACCACCAATGTGGCTAGTGACCTCATGTAC
TAGAAAGCAAATATCTTCATAATTTCTCAATAAGG
ATATGGCTTCCTTTGGCCACTTTTAATATGGGTGA
TTTCATCTGTGCATTTAGACTTCTTAAGTACCAAG
CCCTCCTTATGTTATGTTTACAGAGCATGTAGTAA
GGATTCAGGCTGGAAAATAACAGAAGCAGGAGGAT
GGTTTCACTGGGAAGACGTTCTTCCTGATGGGTAA
TGGCCTGCATAGTTAGTCCAAAGCAGTTGGCTAGA
TGGACGGATGGTTACTCCATGTCCTTACTGACCGA
TAAGATGCACGTTCTCCCAAGCAGAACTCAACAGG
CACATGACATACAGTTTTGTAAGACTCCAGGGAGC
CTTAACTTACCAGGGACCCCCTGAGTGGACCACGT
GGAGCTGGGATCAATGCAAAAAGCAAGAGGAATTT
ATTGTTCCAGTGCACTGGGGTTGTCCCAGATCAAC
AGTGCTGGCAGCGACCCCCAGCACCTTTTCAGTGA
GTTTTTATACGGTTTCTAGGGGCAGAATAGAGCAT
CAGCAACTAGGCACAATATGATTGATGGAACAGTG
CACCCTTTAAACTGATTGGTCTTTAAGGAATGAGG
TGACAAGGACTTCCGTTGTCTGATGGTGGAGGTCC
TGTGGAGTGTGTCCCCACACACAGGTCAGTTCCTG
TCCTTTAGTCTGAGAAATGTTAATTAGCCTCTCCC
TTCCAGAGGGGACGTATTCCATGACCTTCCCAAA
GTTCTTGAGCTGACCTATTCAGTTAAATAAACAG
```

-continued

ACGTTATTTCTAATTGTCCACATAGTCACAGATCC
CAGAAAACAGAGGTGAAATTGGTGTCTTAAACTGA
CAGTGCACCGAATCATTGCAAACCTTCAAGTTCTT
TGTAAGTTTGCTTAGAGCATGATGTCATTATGTCT
GGTGGTCAAAACCAGAAAAGTTTATAAGCAAACAA
GCAAGCTAGCAAGAAAGGAAGAAAAAGGAAAGGAA
GAAAGGAAGAAAGGAAGAAAGGAAGAAAGGAAGGA
AGGAAGGAAGGAAGGAAGGAAGGAAGGAAGGAAGA
CGGAAAGAAGCAGATCAATGGTTTCTTTCCTTATG
CATCTGAGTTCATAACAATGGTACTTACAGTGGAC
AGAATCCCTACTAGACAAGTTGGTGAGAGAAACCC
ACTGGGAACTGTTTCCAGCTTGGTGTCTTTGGCAC
TAATGAGCTCCAAATCATGAAAATTCAGAATTGAG
GTGGGATTGCAGTGTGTCATGGGAGACATGAAGCA
TGGCCCAAGTCAAATCTTTCTCCTTGAATTATTCA
CCAAATGAATCTGCTGGAGACCAGAGGCCACAAGT
GAGCCTGAAACTGACACTCCTTAACTCTCAATGTG
TTACCCTCAGGAAAGAACAAAGGACAAAGACATTA
TGGTGCCCTGGCCACAAACACCAGAGATCATAGAG
TTTGGAAATGCTCCAGAAAACCAATCTGGAACTAG
GAAGATGGCTCAGTTGATAAAGGGCTGCCTCAAAA
GCTTGAGAGCCTGAGTTCAGATTCCCCAGCACCCA
TGAGAAACGCATGGGTTTCATACATGTCTGTGATC
CCAGCACTGGGAAGGCAGAGCTAGGCAAGTCTTAA
AGCTCACCAGCAAGCCAAGTCAAACCTAATCAGTG
CACTCCAAGGTCAGTGAGAGACCCTGACTCAAAAC
AAAAAAACGGAGGTGATGGAGAAAGGCACCATCAG
CCTCCATGAACCCCCTCATGAGCACACACATTTTC
ATTTGGGAACAATTTACATACAAGGAAGGAGAGAC
TGCACACCTGAAATATAACCAGCTCTGGTGATGGC
CTGCTGGTTACTCTCAGACATCAGAACATACTTGC
TTTTCTCAGGATGGAGTCCTTTCACCTTAATTCAG
GACACTGGAAGTTTCTAGAAGCCCACCAGCTAGTC
TGTCCAGGAGCTGGTGCATGCTTTGGTGATGGGCT
AGTAGTGCCCTGACCTGGAGGTCAGACCCTGAAAT
TCTCAAGCACAAAAGGCTGTGTTAGGAGGGAAAGG
GAGGGAGTTGAAGGCTGGAGGATGAATCCCCCTCC
TCTGGCCTCCATCTACCTCTTTCCTCTCTGCTCAG
AGGTCTGAAGTCGACTAGAGCTCGCTGATCAGCCT
CGACTGTGCCTTCTAGTTGCCAGCCATCTGTTGTT
TGCCCCTCCCCCGTGCCTTCCTTGACCCTGGAAGG

-continued

TGCCACTCCCACTGTCCTTTCCTAATAAAATGAGG
AAATTGCATCGCATTGTCTGAGTAGGTGTCATTCT
ATTCTGGGGGGTGGGTGGGGCAGGACAGCAAGGG
GGAGGATTGGGAAGACAATAGCAGGCATGCTGGGG
AGAGATCTAGGAACCCCTAGTGATGGAGTTGGCCA
CTCCCTCTCTGCGCGCTCGCTCGCTCACTGAGGCC
GCCCGGGCAAAGCCCGGGCGTCGGGCGACCTTTGG
TCGCCCGGCCTCAGTGAGCGAGCGAGCGCGCAGAG
AGGGAGTGGCCATGCAGCCAGCTGGCGTAATAGCG
AAGAGGCCCGCACCGATCGCCCTTCCCAACAGTTG
CGTAGCCTGAATGGCGAATGGCGCGACGCGCCCTG
TAGCGGCGCATTAAGCGCGGCGGGTGTGGTGGTTA
CGCGCAGCGTGACCGCTACACTTGCCAGCGCCCTA
GCGCCCGCTCCTTTCGCTTTCTTCCCTTCCTTTCT
CGCCACGTTCGCCGGCTTTCCCCGTCAAGCTCTAA
ATCGGGGGCTCCCTTTAGGGTTCCGATTTAGTGCT
TTACGGCACCTCGACCCCAAAAAACTTGATTAGGG
TGATGGTTCACGTAGTGGGCCATCGCCCTGATAGA
CGGTTTTTCGCCCTTTGACGTTGGAGTCCACGTTC
TTTAATAGTGGACTCTTGTTCCAAACTGGAACAAC
ACTCAACCCTATCTCGGTCTATTCTTTTGATTTAT
AAGGGATTTTGCCGATTTCGGCCTATTGGTTAAAA
AATGAGCTGATTTAACAAAAATTTAACGCGAATTT
TAACAAAATATTAACGTTTACAATTTCCTGATGCG
GTATTTTCTCCTTACGCATCTGTGCGGTATTTCAC
ACCGCATATGGTGCACTCTCAGTACAATCTGCTCT
GATGCCGCATAGTTAAGCCAGCCCCGACACCCGCC
AACACCCGCTGACGCGCCCTGACGGGCTTGTCTGC
TCCCGGCATCCGCTTACAGACAAGCTGTGACCGTC
TCCGGGAGCTGCATGTGTCAGAGGTTTTCACCGTC
ATCACCGAAACGCGCGAGACGAAAGGGCCTCGTGA
TACGCCTATTTTTATAGGTTAATGTCATGATAATA
ATGGTTTCTTAGACGTCAGGTGGCACTTTTCGGGG
AAATGTGCGCGGAACCCCTATTTGTTTATTTTTCT
AAATACATTCAAATATGTATCCGCTCATGAGACAA
TAACCCTGATAAATGCTTCAATAATATTGAAAAAG
GAAGAGTATGAGTATTCAACATTTCCGTGTCGCCC
TTATTCCCTTTTTTGCGGCATTTTGCCTTCCTGTT
TTTGCTCACCCAGAAACGCTGGTGAAAGTAAAAGA
TGCTGAAGATCAGTTGGGTGCACGAGTGGGTTACA

```
TCGAACTGGATCTCAACAGCGGTAAGATCCTTGAG

AGTTTTCGCCCCGAAGAACGTTTTCCAATGATGAG

CACTTTTAAAGTTCTGCTATGTGGCGCGGTATTAT

CCCGTATTGACGCCGGGCAAGAGCAACTCGGTCGC

CGCATACACTATTCTCAGAATGACTTGGTTGAGTA

CTCACCAGTCACAGAAAAGCATCTTACGGATGGCA

TGACAGTAAGAGAATTATGCAGTGCTGCCATAACC

ATGAGTGATAACACTGCGGCCAACTTACTTCTGAC

AACGATCGGAGGACCGAAGGAGCTAACCGCTTTTT

TGCACAACATGGGGATCATGTAACTCGCCTTGAT

CGTTGGGAACCGGAGCTGAATGAAGCCATACCAAA

CGACGAGCGTGACACCACGATGCCTGTAGCAATGG

CAACAACGTTGCGCAAACTATTAACTGGCGAACTA

CTTACTCTAGCTTCCCGGCAACAATTAATAGACTG

GATGGAGGCGGATAAAGTTGCAGGACCACTTCTGC

GCTCGGCCCTTCCGGCTGGCTGGTTTATTGCTGAT

AAATCTGGAGCCGGTGAGCGTGGGTCTCGCGGTAT

CATTGCAGCACTGGGGCCAGATGGTAAGCCCTCCC

GTATCGTAGTTATCTACACGACGGGGAGTCAGGCA

ACTATGGATGAACGAAATAGACAGATCGCTGAGAT

AGGTGCCTCACTGATTAAGCATTGGTAACTGTCAG

ACCAAGTTTACTCATATATACTTTAGATTGATTTA

AAACTTCATTTTTAATTTAAAAGGATCTAGGTGAA

GATCCTTTTTGATAATCTCATGACCAAAATCCCTT

AACGTGAGTTTTCGTTCCACTGAGCGTCAGACCCC

GTAGAAAAGATCAAAGGATCTTCTTGAGATCCTTT

TTTTCTGCGCGTAATCTGCTGCTTGCAAACAAAAA

AACCACCGCTACCAGCGGTGGTTTGTTTGCCGGAT

CAAGAGCTACCAACTCTTTTTCCGAAGGTAACTGG

CTTCAGCAGAGCGCAGATACCAAATACTGTCCTTC

TAGTGTAGCCGTAGTTAGGCCACCACTTCAAGAAC

TCTGTAGCACCGCCTACATACCTCGCTCTGCTAAT

CCTGTTACCAGTGGCTGCTGCCAGTGGCGATAAGT

CGTGTCTTACCGGGTTGGACTCAAGACGATAGTTA

CCGGATAAGGCGCAGCGGTCGGGCTGAACGGGGGG

TTCGTGCACACAGCCCAGCTTGGAGCGAACGACCT

ACACCGAACTGAGATACCTACAGCGTGAGCATTGA

GAAAGCGCCACGCTTCCCGAAGGGAGAAAGGCGGA

CAGGTATCCGGTAAGCGGCAGGGTCGGAACAGGAG

AGCGCACGAGGGAGCTTCCAGGGGGAAACGCCTGG

TATCTTTATAGTCCTGTCGGGTTTCGCCACCTCTG

ACTTGAGCGTCGATTTTTGTGATGCTCGTCAGGGG

GGCGGAGCCTATGGAAAAACGCCAGCAACGCGGCC

TTTTTACGGTTCCTGGCCTTTTGCTGGCCTTTTGC

TCACATGTTCTTTCCTGCGTTATCCCCTGATTCTG

TGGATAACCGTATTACCGCCTTTGAGTGAGCTGAT

ACCGCTCGCCGCAGCCGAACGACCGAGCGCAGCGA

GTCAGTGAGCGAGGAAGCGGAAGAGCGCCCAATAC

GCAAACCGCCTCTCCCCGCGCGTTGGCCGATTCAT

TAATGCAGCTGGGCTGCAGGGGGGGGGGGGGGGG

GT
```

As used herein, the term "sequence identity" refers to the percentage of amino acid (or nucleic acid) residues of a candidate sequence that are identical to the amino acid (or nucleic acid) residues of a reference sequence, e.g., clarin-1 protein disclosed herein and its coding sequences, after aligning the sequences and introducing gaps, if necessary, to achieve the maximum percent identity (e.g., gaps can be introduced in one or both of the candidate and reference sequences for optimal alignment and non-homologous sequences can be disregarded for comparison purposes). Alteration of the amino acid sequence or nucleic acid coding sequences can be obtained by deletion, addition or substitution of residues of the reference sequence. Alignment for purposes of determining percent identity can be achieved in various ways that are within the skill of one in the art, for instance, using publicly available computer software, such as BLAST, BLAST-2, BLAST-P, BLAST-N, BLAST-X, WU-BLAST-2, ALIGN, ALIGN-2, CLUSTAL, or Megalign (DNASTAR) software. Those skilled in the art can determine appropriate parameters for measuring alignment, including any algorithms needed to achieve maximal alignment over the full length of the sequences being compared. For instance, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of A/B})$$

where A is the number of amino acid (or nucleic acid) residues scored as identical in the alignment of the candidate sequence and the reference sequence, and where B is the total number of amino acid (or nucleic acid) residues in the reference sequence. In particular, a reference sequence aligned for comparison with a candidate sequence can show that the candidate sequence exhibits from, e.g., 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, 50%, 60%, 70%, 80%, 90%, 95%, 98%, 99%, or 100% of the length of the reference sequence. When a position in the candidate sequence is occupied by the same amino acid (or nucleic acid) residue as the corresponding position in the reference sequence, then the molecules are identical at that position.

In some embodiments, the rAAV is a single stranded AAV (ssAAV). An ssAAV, as used herein, refers to a rAAV with the coding sequence and complementary sequence of the transgene expression cassette on separate strands and packaged in separate viral capsids. In some embodiments, the rAAV is a self-complementary AAV (scAAV). A scAAV, as used herein, refers to an rAAV with both the coding and complementary sequence of the transgene expression cassette are present on each plus- and minus-strand genome. The coding region of a scAAV was designed to form an intra-molecular double-stranded DNA template. Upon infection, rather than waiting for cell-mediated synthesis of the second strand, the two complementary halves of scAAV associate to form one double stranded DNA (dsDNA) unit that is ready for immediate replication and transcription.

In some embodiments, the rAAV, as provided herein, is capable of delivering the transgene (e.g., the transgene for expressing clarin-1 protein) to a mammal. In some embodiments, the mammal is a human. In some embodiments, the mammal is a non-human mammal, such as a mouse, a rat, or a non-human primate (e.g., cynomolgus monkey), a cat, a dog, a pig, a horse, a donkey, a camel, a sheep, or a goat.

In some embodiments, the rAAV, as provided herein, is capable of delivering the transgene (e.g., the transgene for expressing a clarin-1 protein) to the inner ear cells (e.g., inner hair cells, outer hair cells, and fibrocytes) and/or the eye cells (e.g., retina cells, such as photoreceptors). In some embodiments, the rAAV described herein is capable of transducing a wide variety of ear cells, including, but not limited to: outer hair cell (OHCs), inner hair cell (IHCs), supporting cell (e.g., border cell, inner phalangeal cell, inner pillar cell, outer pillar cell, Deiters' cell, Hensen's, or Claudius' cell), spiral ganglion neuron, spiral limbus cells (e.g., glial cell or interdental cell), outer sulcus cells, cells of the lateral wall, cells of the stria vascularis (e.g., basal cell and intermediate cell), cells of the inner sulcus, cells of the spiral ligament (e.g., fibrocytes), or cells of the vestibular system. In some embodiments, rAAV described herein is capable of transducing a wide variety of eye cells, including, but not limited to: photoreceptor cells (e.g., rods and cones), cells of the outer plexiform layer (OPL), cells of the inner nuclei layer (INL), cells of the ganglion cell layer (GCL), cells of the inner plexiform layer (IPL), or retinal pigment epithelium (RPE) cells.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be alternatively under the control of a constitutive promoter. Examples of suitable inducible and constitutive promoters are provided herein, in the discussion of regulatory elements suitable for use with the transgene. In still another alternative, a stable host cell may contain selected component(s) under the control of a constitutive promoter, and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing the isolated nucleic acid described herein (e.g., the isolated nucleic acid for expressing clarin-1 protein). In some embodiments, the instant disclosure relates to a host cell containing the rAAV encoding the clarin-1 protein. In some embodiments, the host cell is a mammalian cell (e.g., a human cell), a yeast cell, a bacterial cell, an insect cell, a plant cell, or a fungal cell.

The recombinant AAV vector, rep sequences, cap sequences, and helper functions required for producing the rAAV of the disclosure may be delivered to the packaging host cell using any appropriate genetic element (e.g., vector). The selected genetic element may be delivered by any suitable method, including those described herein and those known in the art. The methods used to construct any embodiment of this disclosure are known to those with skill in nucleic acid manipulation and include genetic engineering, recombinant engineering, and synthetic techniques. See, e.g., Sambrook et al., *Molecular Cloning: A Laboratory Manual*, Cold Spring Harbor Press, Cold Spring Harbor, N.Y. Similarly, methods of generating rAAV virions are known in the art, and the selection of a suitable method is not a limitation on the present disclosure. See, e.g., K. Fisher et al., *J. Virol.*, 70:520-532 (1993) and U.S. Pat. No. 5,478,745; each of which is incorporated herein by reference.

In some embodiments, recombinant AAVs may be produced using the triple transfection method (described in detail in U.S. Pat. No. 6,001,650, which is incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both of which are incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those proteins involved in activation of AAV gene transcription, stage specific AAV mRNA splicing, AAV DNA replication, synthesis of cap expression products, and AAV capsid assembly. Viral-based accessory functions can be derived from any of the known helper viruses, such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, A Laboratory Manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest (e.g., nucleic acid, virus). Often a host cell is a mammalian cell. A host cell may be used as a recipient of an AAV helper construct, an AAV plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the expression of a polypeptide or production of a nucleic acid, such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements, and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter.

The term "expression vector or construct" means any type of genetic construct containing a nucleic acid in which part or all of the nucleic acid encoding sequence is capable of being transcribed.

The foregoing methods for packaging recombinant vectors in desired AAV capsids to produce the rAAVs of the disclosure are not meant to be limiting and other suitable methods will be apparent to the skilled artisan.

In some embodiments, rAAV described herein comprises an isolated nucleic acid (e.g., the rAAV vector) comprising, from 5' to 3', a 5' AAV ITR, a Human Cytomegalovirus Major Immediate-Early Enhancer (CMV IE enhancer), a promoter (e.g., chicken beta actin promoter), a beta-actin exon, a chimeric intron, a 5' UTR, a Kozak sequence, a nucleotide sequence encoding a clarin-1 protein, a 3' UTR, a bovine growth hormone poly A signal, and a 3' AAV ITR. In addition, the rAAV may additionally comprise a capsid protein (e.g., AAV-S capsid). Such rAAV can deliver transgenes (e.g., CLRN1) to target tissues (e.g., ear cells such as the inner hair cells, outer hair cells, fibrocytes, and/or eye cells such as photoreceptors).

II. Pharmaceutical Composition

The rAAVs may be delivered to a subject in compositions according to any appropriate methods known in the art. The rAAV, preferably suspended in a physiologically compatible carrier (i.e., in a composition), may be administered to a subject, i.e. host animal. In some embodiments, the host animal is a mammal. In some examples, the mammal is a human. In other embodiments, the mammal can be a non-human mammal, such as a human, mouse, rat, cat, dog, sheep, rabbit, horse, cow, goat, pig, guinea pig, hamster, chicken, turkey, or a non-human primate (e.g., cynomolgus monkey).

Delivery of the rAAVs to a mammalian subject may be by, for example, injection to the ear or the eye. In some embodiments, the injection is to the ear through round window membrane of the inner ear or topical administration (e.g., ear drops). In some embodiments, the injection is the eye (e.g., intravitreal injection) or topical administration (e.g., eye drops). In some embodiments, the injection is not topical administration. Combinations of administration methods (e.g., topical administration and injection through round window membrane of the inner ear) can also be used.

The compositions of the disclosure may comprise a rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., *Remington: The Science and Practice of Pharmacy* 20th Ed. (2000) Lippincott Williams and Wilkins, Ed. K. E. Hoover. For example, one acceptable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

The rAAV containing pharmaceutical composition disclosed herein may further comprise a suitable buffer agent, include, but are not limited to, HEPES (4-(2-hydroxyethyl)-1-piperazineethanesulfonic acid) buffer, Dulbecco's phosphate-buffered saline (DPBS) buffer, or Phosphate-buffered Saline (PBS) buffer. Such buffers may comprise disodium hydrogen phosphate and sodium chloride, or potassium dihydrogen phosphate and potassium chloride.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAV containing pharmaceutical composition described herein comprises one or more suitable surface-active agents, such as a surfactant. Surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Suitable surfactants include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example, mannitol or other pharmaceutically acceptable vehicles, if necessary.

The rAAVs are administered in sufficient amounts to transduce the cells of a desired tissue (e.g., inner hair cells, outer hair cells, fibrocytes in the inner ear or photoreceptors of the eye) and to provide sufficient levels of gene transfer and expression without undue adverse effects. Examples of pharmaceutically acceptable routes of administration include, but are not limited to, direct delivery to the selected organ (e.g., the ear and/or the eye), injection through the round window membrane of the inner ear, intraocular, intravitreal, subretinal, intravenous, intramuscular, subcutaneous, intradermal, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of a rAAV is an amount sufficient to target infect an animal (e.g., mouse, rat, non-human primate or human), target a desired tissue (e.g., the inner ear or the eye). The effective amount will depend primarily on factors such as the species, age, weight, health of the subject, and the tissue to be targeted, and may thus vary among animal and tissue. For example, an effective amount of the rAAV is generally in the range of from about 1 µl to about 100 ml of solution containing from about $10^9$ to $10^{16}$ genome copies. In some cases, a dosage between about $10^{11}$ to $10^{13}$ rAAV genome copies is appropriate. In certain embodiments, $10^9$ rAAV genome copies is effective to target inner ear tissue (e.g., inner hair cells, outer hair cells or fibrocytes of the inner ear). In some embodiments, a dose more concentrated than $10^9$ rAAV genome copies is toxic when administered to the eye of a subject. In some embodiments, an effective amount is produced by multiple doses of a rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year). In some embodiments, a dose of rAAV is administered to a subject once.

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright et al., *Molecular Therapy* (2005) 12, 171-178, the contents of which are incorporated herein by reference.)

Formulation of pharmaceutically acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to inner ear tissue (e.g., inner hair cells, outer hair cells or fibrocytes of the inner ear) and/or the eye (e.g., photoreceptors). The rAAVs in suitably formulated pharmaceutical compositions disclosed herein are delivered directly to the ear (e.g., inner hair cells, outer hair cells or fibrocytes of the inner ear) and/or the eye (e.g., photoreceptors). However, in certain circumstances it may be desirable to separately or in addition deliver the rAAV-based therapeutic constructs via another route, e.g., subcutaneously, intranasally, parenterally, intravenously, intramuscularly, or intraperitoneally. In some embodiments, the administration modalities as described in U.S. Pat. Nos. 5,543,158; 5,641,515 and 5,399,363 (each of which is incorporated herein by reference in its entirety) may be used to deliver rAAVs.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases, the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation and in such amount as is therapeutically effective. The formulations are easily administered in a variety of dosage forms, such as injectable solutions, drug-release capsules, and the like.

As used herein, "carrier" or "excipient" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically acceptable" refers to molecular entities and compositions that do not produce an allergic or similar untoward reaction when administered to a host.

Delivery vehicles, such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, a nanoparticle, or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516, which is incorporated herein by reference). Further, various methods of liposome and liposome like preparations as potential drug carriers have been described (U.S. Pat. Nos. 5,567,434; 5,552,157; 5,565,213; 5,738,868 and 5,795,587; each of which is incorporated herein by reference).

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable poly-alkyl-cyanoacrylate nanoparticles that meet these requirements are contemplated for use.

III. Method for Treating Usher Syndrome, Type 3A

The present disclosure also provides methods for delivering a transgene to the ear and/or the eye. In some embodiments, the method is for delivering a transgene (e.g., the transgene for expressing the clarin-1 protein) to cochlear (e.g., inner hair cells, outer hair cells or fibrocytes of the inner ear) tissue in a subject. In other embodiments, the method is for delivering a transgene (e.g., the transgene for expressing the clarin-1 protein) to cells in the eye (e.g., photoreceptors) of a subject. The methods typically involve administering to a subject an effective amount of a rAAV comprising a nucleic acid for expressing a transgene (e.g., the transgene for expressing the clarin-1 protein) in the subject. An "effective amount" of a rAAV is an amount sufficient to infect a sufficient number of cells of a target tissue (e.g., in the ear or eye) in a subject. In some embodiments, a target tissue is cochlear (e.g., inner hair cells, outer hair cells or fibrocytes of the inner ear.) tissue. In some embodiments, a target tissue is ocular tissue (e.g., retina cells, such as photoreceptors). An effective amount of a rAAV may be an amount sufficient to have a therapeutic benefit in a subject, e.g., to improve in the subject one or more symptoms or signs of a disease, e.g., a symptom of a hereditary hearing loss and/or vision loss (e.g., Usher syndrome type 3A). In some cases, an effective amount of a rAAV may be an amount sufficient to produce a stable somatic transgenic animal model. The effective amount will depend on a variety of factors, such as, for example, the species, age, weight, health of the subject, and the tissue (e.g., inner ear and/or ocular tissue) to be targeted, and may thus vary among subjects and tissues to be treated.

An effective amount may also depend on the rAAV used. The invention is based, in part on the recognition that rAAV comprising capsid proteins having a particular serotype (e.g., AAV-S capsid protein) mediate more efficient transduction of cochlear (e.g., inner hair cells, outer hair cells, or fibrocytes of the inner ear) tissue and/or ocular tissue (e.g., retina cells, such as photoreceptors) than rAAV comprising capsid proteins having a different serotype (e.g., AAV 9 capsid protein).

In certain embodiments, the effective amount of rAAV is $10^{10}$, $10^{11}$, $10^{12}$, $10^{13}$, or $10^{14}$ genome copies per kg of the subject. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting a cochlear (e.g., inner hair cells, outer hair cells, or fibrocytes of the inner ear.) tissue by injection through the round window membrane of the inner ear may require different (e.g., higher or lower) doses, in some cases, than targeting a cochlear (e.g., inner hair cells, outer hair cells, or fibrocytes of the inner ear.) tissue by another method (e.g., systemic administration, topical administration). Thus, in some embodiments, the injection is an injection through the round window membrane of the inner ear. In some embodiments, the administration is topical administration (e.g., topical administration to an ear). In other cases, targeting the eye (e.g., photoreceptors) by injection into the eye (e.g., intravitreal injection) may require different does, in some cases, than targeting the eye (e.g., photoreceptors) by another method (e.g., systemic administration, topical administration). In some embodiments, the administration is via injection, optionally subretinal injection or intravitreal injection. In some embodiments, the administration is topical administration (e.g., topical administration to an eye). In some cases, multiple doses of a rAAV are administered.

Without wishing to be bound by any particular theory, efficient transduction of cochlear cells (e.g., inner hair cells, outer hair cells, or fibrocytes of the inner ear) and/or (ocular tissue (e.g., retina cells, such as photoreceptors) by rAAV described herein may be useful for the treatment of a subject having a hereditary hearing loss and/or vision loss (e.g., Usher syndrome type 3A). Accordingly, methods and compositions for treating hereditary hearing loss and/or vision loss (e.g., Usher Syndrome, Type 3A) are also provided herein, the method comprising: administering to a subject having or suspected of having a hereditary hearing loss an effective amount of rAAV, wherein the rAAV comprises (i) a capsid protein having a serotype of AAV-S, and (ii) a nucleic acid comprising a promoter operably linked to a transgene (e.g., a transgene for expressing a clarin-1 protein).

In some embodiments, the subject being treated is a mammal. In some embodiments, the subject is a human or a non-human mammal, such as a mouse, rat, or non-human primate (e.g., cynomolgus monkey), a dog, a cat, a pic, a cow, a sheep, a goat, a camel, or a donkey. In some embodiments, the subject is a human.

Aspects of the invention relate to certain protein-encoding transgenes (e.g., CLRN1) that when delivered to a subject are effective for promoting communication between nerve cells (neurons) in the inner ear and/or for promoting communication between nerve cells in the retina of the subject. In some embodiments, the subject has or is suspected of having hearing loss and/or vision loss. In some embodiments, the hearing loss and/or vision loss is associated with the CLRN1 gene. In some examples, the hearing loss and/or vision loss is associated with a mutation in the CLRN1 gene. In some embodiments, the hearing loss and/or vision loss is associated with a lack of function of the CLRN1 gene. In some embodiments, the hearing loss and/or vision loss is associated with a lack of expression of the CLRN1 gene. In one example, the subject is diagnosed with Usher Syndrome, Type 3A.

Accordingly, methods and compositions described by the disclosure are useful, in some embodiments, for the treatment of Usher syndrome, Type 3A. In some embodiments, methods and composition described by this disclosure are useful, in some embodiments, for the treatment of disorders associated with mutations or deletions of the CLRN1 gene (e.g., such as sensorineural hearing loss, deafness, and/or progressive vision loss). In some embodiments, methods and compositions described by the disclosure are useful for the treatment of hearing loss and/or vision loss.

Methods for delivering a transgene (e.g., the transgene for expressing a clarin-1 protein) to a subject are provided by the disclosure. In some embodiments, the methods involve administering to a subject an effective amount of an isolated nucleic acid encoding clarin-1. In some embodiments, the methods typically involve administering to a subject an effective amount of rAAV comprising a nucleic acid for expressing clarin-1.

In some embodiments, the hearing loss and/or vision loss is Usher syndrome, Type 3A. Generally, a mutation or mutations in CLRN1 account for Usher syndrome, Type 3A. In some embodiments, the CLRN1 mutation can be, but are not limited to, point mutations, missense mutations, nonsense mutations, insertions, or deletions. In some examples, the CLRN1 gene mutations associated with Usher syndrome, type 3A, include, but are not limited to, c.528T>G, c.149delCAGG/insTGTCCAAT, c.165delC, or c.144T>G. All the mutations known in the art and described by, for example, Fields et al. (2002) *Am J Hum Genet.* 71(3):607-617, are encompassed by the present disclosure. Mutations in a CLRN1 gene of a subject (e.g., a subject having or suspected of having Usher Syndrome type 3A associated with a deletion or mutation of CLRN1 gene) may be identified from a sample obtained from the subject (e.g., a DNA sample, RNA sample, blood sample, or other biological sample) by any method known in the art. For example, in some embodiments, a nucleic acid (e.g., DNA, RNA, or a combination thereof) is extracted from a biological sample obtained from a subject, and nucleic acid sequencing is performed in order to identify a mutation in the CLRN1 gene.

In some aspects, the disclosure provides methods for treating an Usher syndrome, Type 3A, in a subject in need thereof, the method comprising administering to a subject having or suspected of having Usher syndrome, Type 3A, a therapeutically effective amount of an isolated nucleic acid, or a rAAV, by injection through the round window membrane of the inner ear. In other embodiments, the injection is to the eye (e.g., intravitreal injection).

In some aspects, the disclosure provides an rAAV (e.g., rAAV comprising AAV-S protein and an isolated nucleic acid encoding a clarin-1 protein) for use in a therapy. In some aspects, the disclosure provides an rAAV (e.g., rAAV comprising AAV-S protein and an isolated nucleic acid encoding a clarin-1 protein) for use in the treatment of hearing loss and/or vision loss. In some aspects, the disclosure provides an rAAV (e.g., rAAV comprising AAV-S protein and an isolated nucleic acid encoding a clarin-1 protein) for use in the treatment of Usher Syndrome, Type 3A. In some aspects, the disclosure provides an rAAV (e.g., rAAV comprising AAV-S protein and an isolated nucleic acid encoding a clarin-1 protein) for use in the treatment of a CLRN-1 associated disease. In some aspects, the disclosure provides an rAAV (e.g., rAAV comprising AAV-S protein and an isolated nucleic acid encoding a clarin-1 protein) for the manufacture of a medicament in treating hearing loss and/or vision loss. In some aspects, the disclosure provides an rAAV (e.g., rAAV comprising AAV-S protein and an isolated nucleic acid encoding a clarin-1 protein) for the manufacture of a medicament in treating Usher Syndrome, Type 3A. In some aspects, the disclosure provides an rAAV (e.g., rAAV comprising AAV-S protein and an isolated nucleic acid encoding a clarin-1 protein) for the manufacturing of a medicament in treating a CLRN-1 associated disease.

IV. Kits and Related Composition

The agents described herein may, in some embodiments, be assembled into pharmaceutical or research kits to facilitate their use in therapeutic, or research applications. A kit may include one or more containers housing the components described herein and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid comprising a transgene encoding a clarin-1 protein having the amino acid sequence at least 60%, at least 70%, at least 80%, at least 85%, at least 90%, at least 91%, at least 92%, at least 93%, at least 94%, at least 95%, at least 96%, at least 97%, at least 98%, at least 99%, or 100% identical to amino acid sequences as set forth in SEQ ID NOs: 5-9 or 11-13. In some embodiments, the kit further comprises a container housing an isolated nucleic acid encoding an AAV capsid protein, for example, an AAV-S capsid protein (e.g., SEQ ID NO: 3). In some embodiments, the kit comprises additional reagents (e.g., vectors encoding the rep gene, transfection reagent, etc.) for packaging of the rAAV.

The kit may be designed to facilitate use of the methods described herein by researchers and can take many forms. Each of the compositions of the kit, where applicable, may be provided in liquid form (e.g., in solution) or in solid form (e.g., a dry powder, a lyophilized powder). In certain cases, some of the compositions may be constitutable or otherwise processable (e.g., to an active form), for example, by the addition of a suitable solvent or other species (for example, water, buffered solution, or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), internet, and/or web-based communications, etc. The written instructions may be in a form prescribed by a governmental agency (e.g., US FDA or European Medicines Agency) regulating the manufacture, use or sale of pharmaceuticals or biological products, which instructions can also reflect approval by the agency of manufacture, use, or sale for animal administration and/or human use.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel, or solid (e.g., powder). The agents may be prepared sterilely, packaged in syringe, and shipped refrigerated. Alternatively, it may be housed in a vial or other container for storage. A second container may have other agents prepared sterilely. Alternatively, the kit may include the active agents premixed and shipped in a syringe, vial, tube, or other container.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

VI. General Techniques

The practice of the present invention will employ, unless otherwise indicated, conventional techniques of molecular biology (including recombinant techniques), microbiology, cell biology, biochemistry, and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995)

Without further elaboration, it is believed that one skilled in the art can, based on the present disclosure, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Exemplary embodiments of the invention will be described in more detail by the following examples. These embodiments are exemplary of the invention, which one skilled in the art will recognize is not limited to the exemplary embodiments.

EXAMPLES

Example 1

AAV-S capsid protein is a AAV9 capsid variant, which has a 7-amino-acid peptide, STTLYSP (SEQ ID NO: 2), inserted between positions 588 and 589 of the AAV9 VP1 capsid protein. AAV-S capsid was originally developed to be a brain-targeting capsid protein, but failed to effectively cross the blood-brain barrier (Hanlon et al., Selection of an Efficient AAV Vector for Robust CNS Transgene Expression, *Molecular Therapy Methods & Clinical Development*, Volume 15, 13 Dec. 2019, Pages 320-332). Surprisingly, AAV-S showed good tropism for peripheral organs. In the present Example, it was observed that AAV-S could efficiently transduce cells of the inner ear of mice and non-human primates (NHP). AAV-S-CLRN1 was tested for its capability to drive CRLN1 expression in the NHP inner ear and retina, and its effectiveness in treating Usher syndrome, type 3A. The cell types (e.g., inner and outer hair cells, and a wide variety of other cells) that can be transduced are evaluated.

Usher syndrome, type 3A (Usher 3A), causes progressive hearing loss and progressive blindness due to mutations in the CLRN1 gene, which encodes a small membrane protein, clarin-1. The ability of AAV-S to rescue the deafness phenotype in a mouse model of Usher 3A by delivering CLRN1 gene to hair cells was tested.

A recombinant adeno-associated virus (rAAV) comprising an AAV-S capsid and an EGFP expression cassette including an EGFP coding sequence under the control of the chicken beta-actin (CBA) promoter and a Woodchuck Hepatitis Virus (WHP) Posttranscriptional Regulatory Element (WPRE) was made. This rAAV was used to test the transduction capability of AAV-S of mouse inner ear cells and retina cells. C57/BL6 mice were injected at P1 with $2\times10^{10}$ vector genomes (VG) through the round window membrane. Mice were euthanized at P6, and cochleas were dissected and imaged for GFP expression.

Figure 1B:
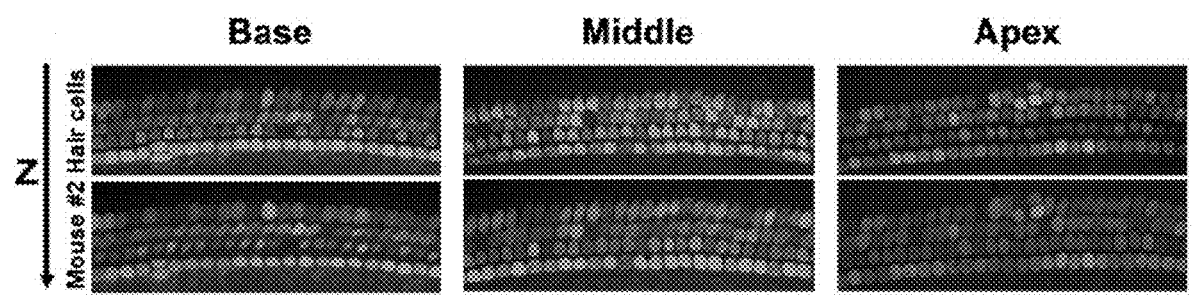
Figure 1C:
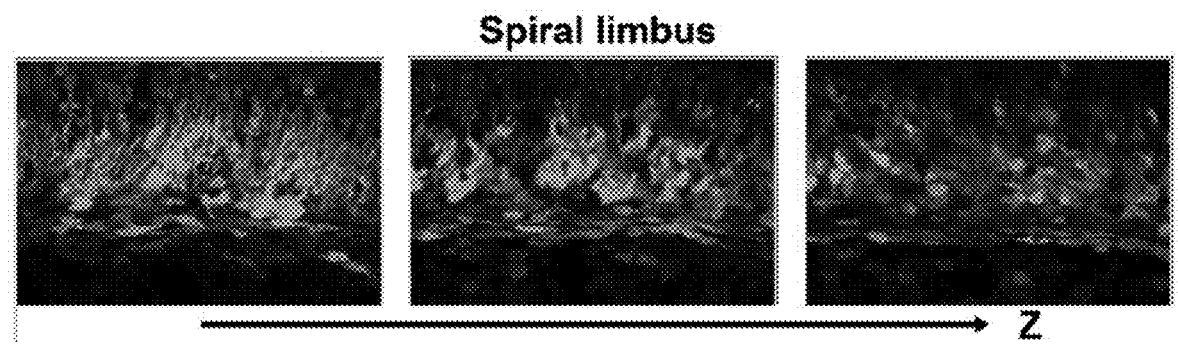
Figure 1D:
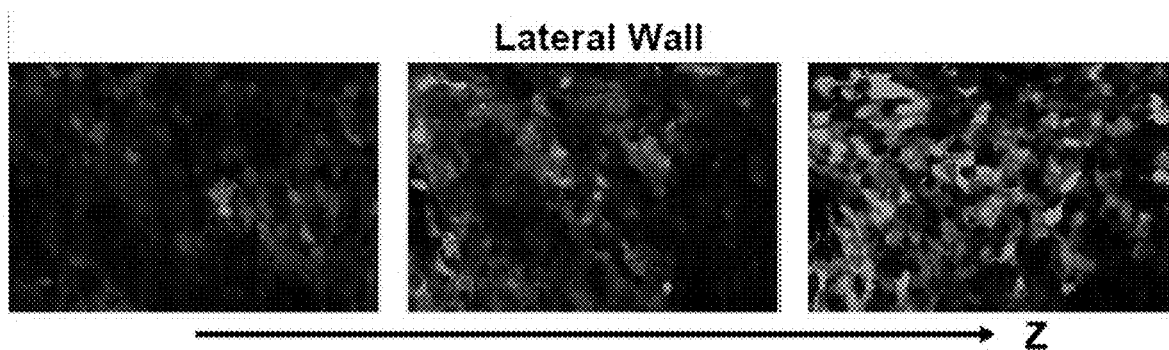

AAV-S transduced hair cells of the mouse cochlea extremely well. Both inner and outer hair cells were transduced with efficiencies of up to 100% and 99% (FIGS. 1A-1B). There was also significant transduction of the spiral limbus and lateral wall (FIGS. 1C-1D).

Figure 2A:
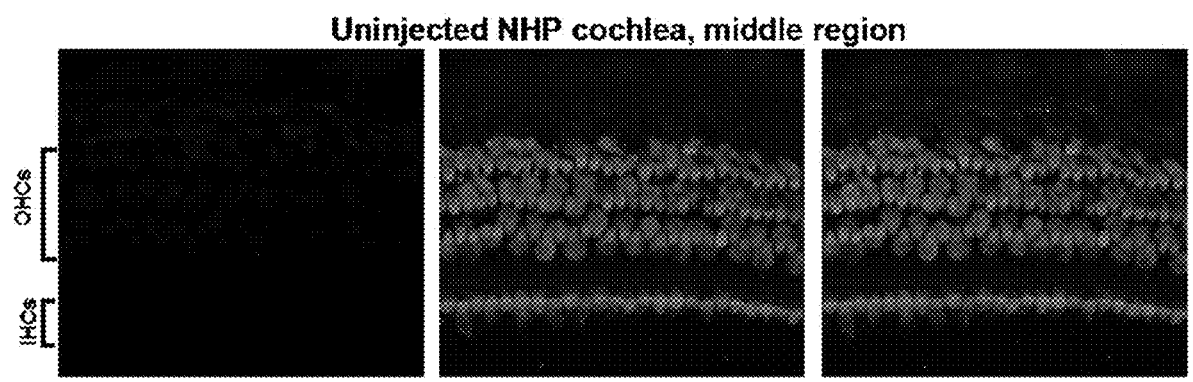
FIGS. 2A-2C show AAV-S GFP expression in a non-human primate cochlea. *Cochleae* were stained with anti-GFP (1:200 dilution).
Figure 2B:
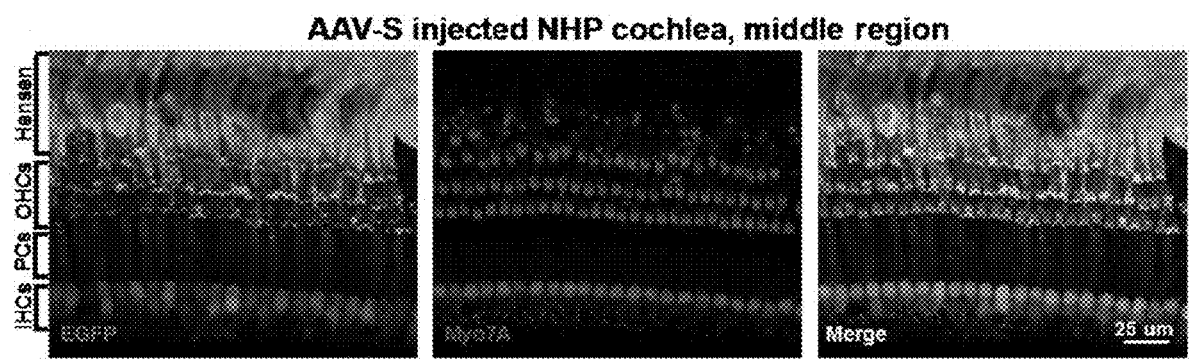
Figure 2C:
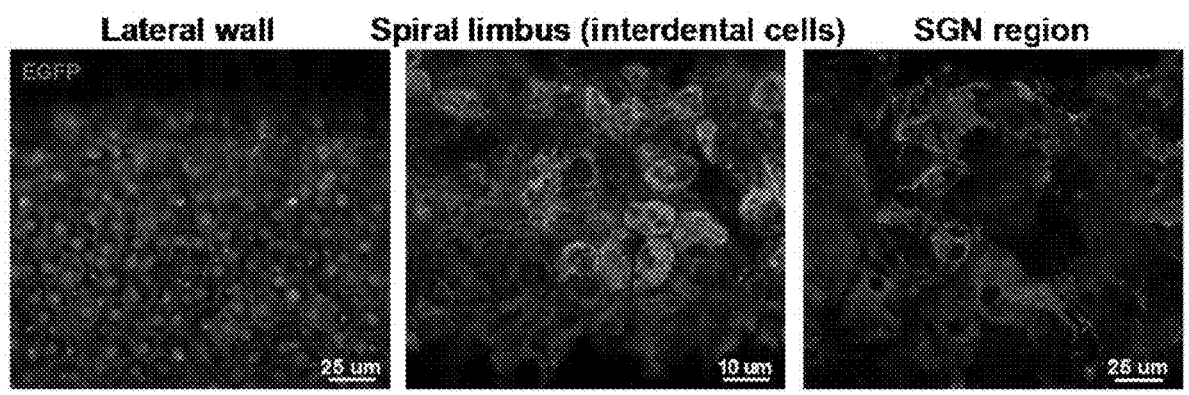

Primate work was carried out on cynomolgus monkey. The Cynomolgus Macaque (cyno) was injected through the round window membrane following mastoidectomy to expose the round window. 20 µl of vector was administered at a total dose of $5\times10^{11}$ VG (viral genome) of AAV-S-EGFP. The Cynomolgus Macaque was euthanized three weeks later, and the cochlea processed. No GFP expression was observed in the cochlea of the uninjected Cynomolgus Macaque. High levels of EGFP expression was observed in inner and outer hair cells of the cyno that received AAV-S-EGFP injection (FIG. 2B), as did supporting cells in the organ of Corti. Significant transduction was also observed in the lateral wall, spiral limbus, and spiral ganglion (FIG. 2C).

Figure 5:
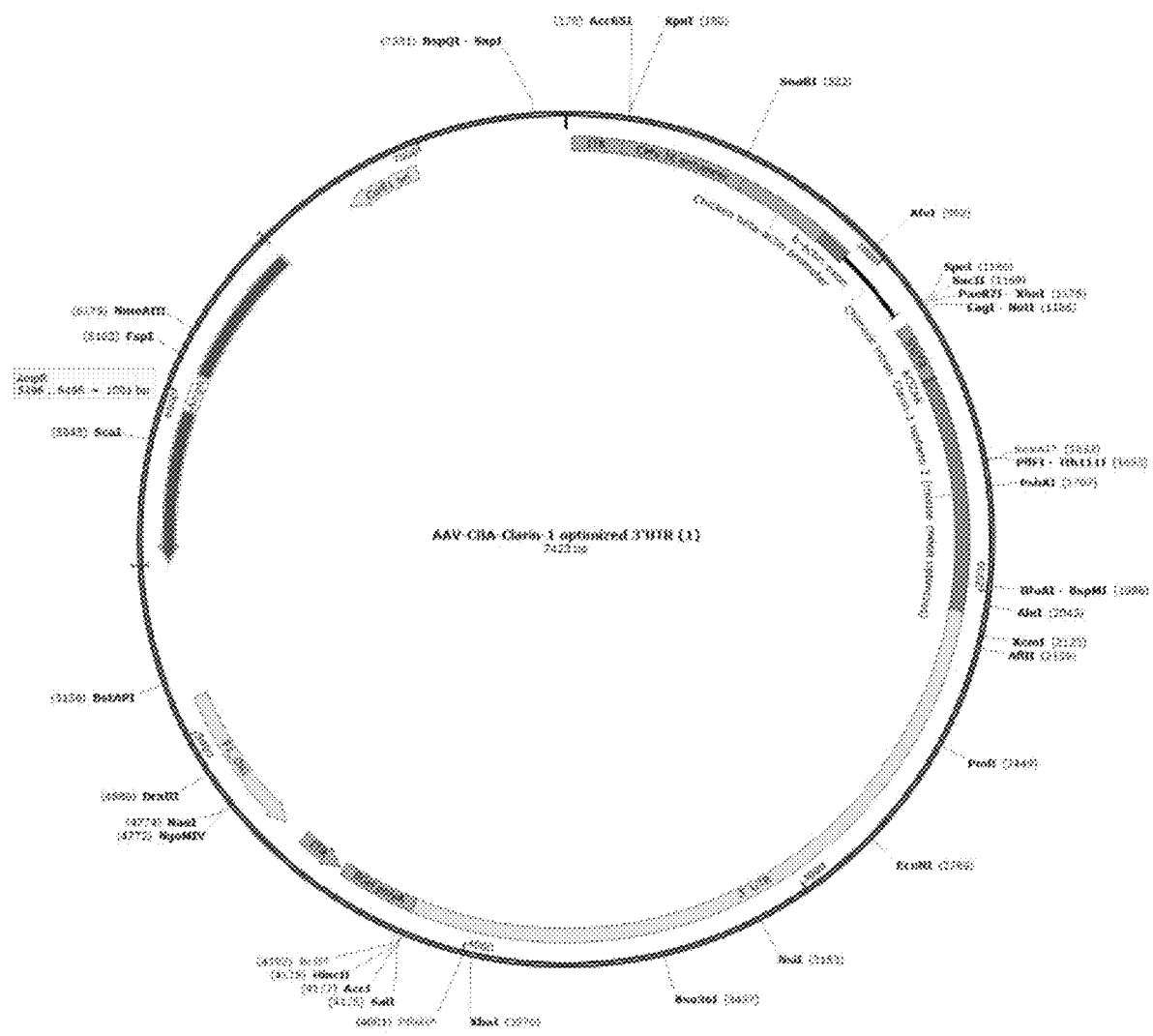
FIG. 5 shows a map of the AAV vector encoding clarin-1 protein.

Subsequently, a second rAAV comprising AAV-S and a codon-optimized Clrn1 gene under the control of a CBA promoter, and flanked by the 5' and 3' untranslated regions of the Clrn1 gene (optiClarin-1, FIG. 5) was also produced. This rAAV was tested for its capability to rescue hearing in a Clrn1 knock out mouse model. In this mouse model, endogenous Clrn1 was knocked out, and the mice temporarily express Clrn1 under the control of a mouse Atoh1 promoter (TgAC1/Clrn1-KO). In humans, Usher 3A causes progressive hearing loss during the first three decades of life. This mouse model more accurately mimics the progressive disease pathogenesis than the congenitally deaf Clrn1 knockout. TgAC1/Clrn1-KO mice were injected at P1 with 2×1010 vector genomes (VG) through the round window membrane. Auditory brainstem response (ABR) and distortion product oto-acoustic emission (DPOAE) tests were performed on TgAC1/Clrn1-KO mice at P35, P60, and P90 (separate groups).

Figure 3A:
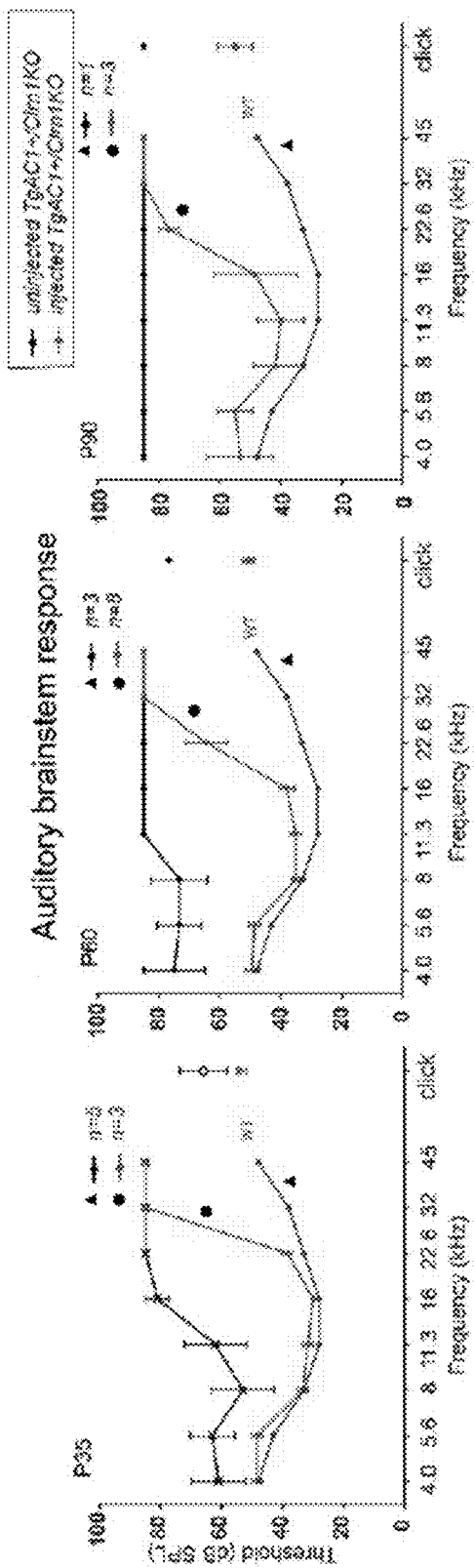
FIGS. 3A-3B show rescue of hearing in an Usher 3A mouse model with AAV-S encoding Clarin-1. Hearing tests were conducted on three groups of animals, at P35, P60, and P90.
Figure 3B:
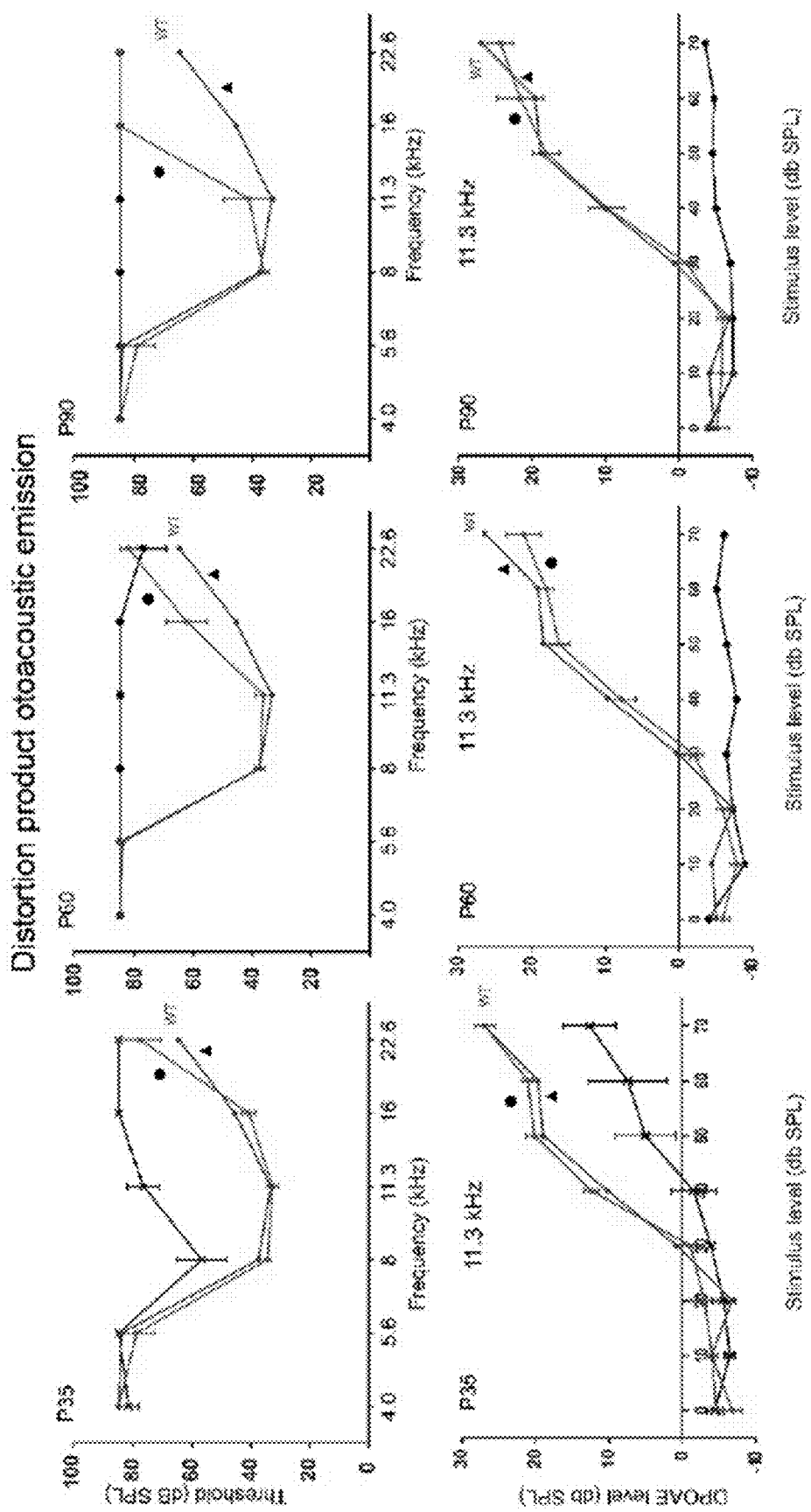

ABR data showed that TgAC1/Clrn1-KO mice at age P35 had significant mid- and high-frequency hearing loss (>80 dB threshold above 12 kHz, ~50-60 dB threshold below 12 kHz; FIG. 3A). Mice injected with AAV-S-codon optimized CLRN1 demonstrated rescue at low and mid frequencies (up to 22 kHz), with thresholds in the mid-frequency range equivalent to hearing controls (FIG. 3A). DPOAEs in this group also showed excellent rescue at mid and high frequencies (FIG. 3B).

Mice were retested at P60 alongside a second group; Auditory Brainstem Response (ABRs) were similar to the P35 group, with somewhat less rescue at 22.6 kHz (FIG. 3A). Similarly, Distortion product otoacoustic emissions (DPOAEs) in the P60 group nearly unchanged from P35 (FIG. 3B). At P90, the untreated mice were completely deaf, but most treated mice still showed good rescue of the ABR. DPOAE thresholds were largely unchanged except for loss of sensitivity at 16 kHz. Better rescue was observed than previously reported in these mice by others using different AAV capsids.

Figure 4:
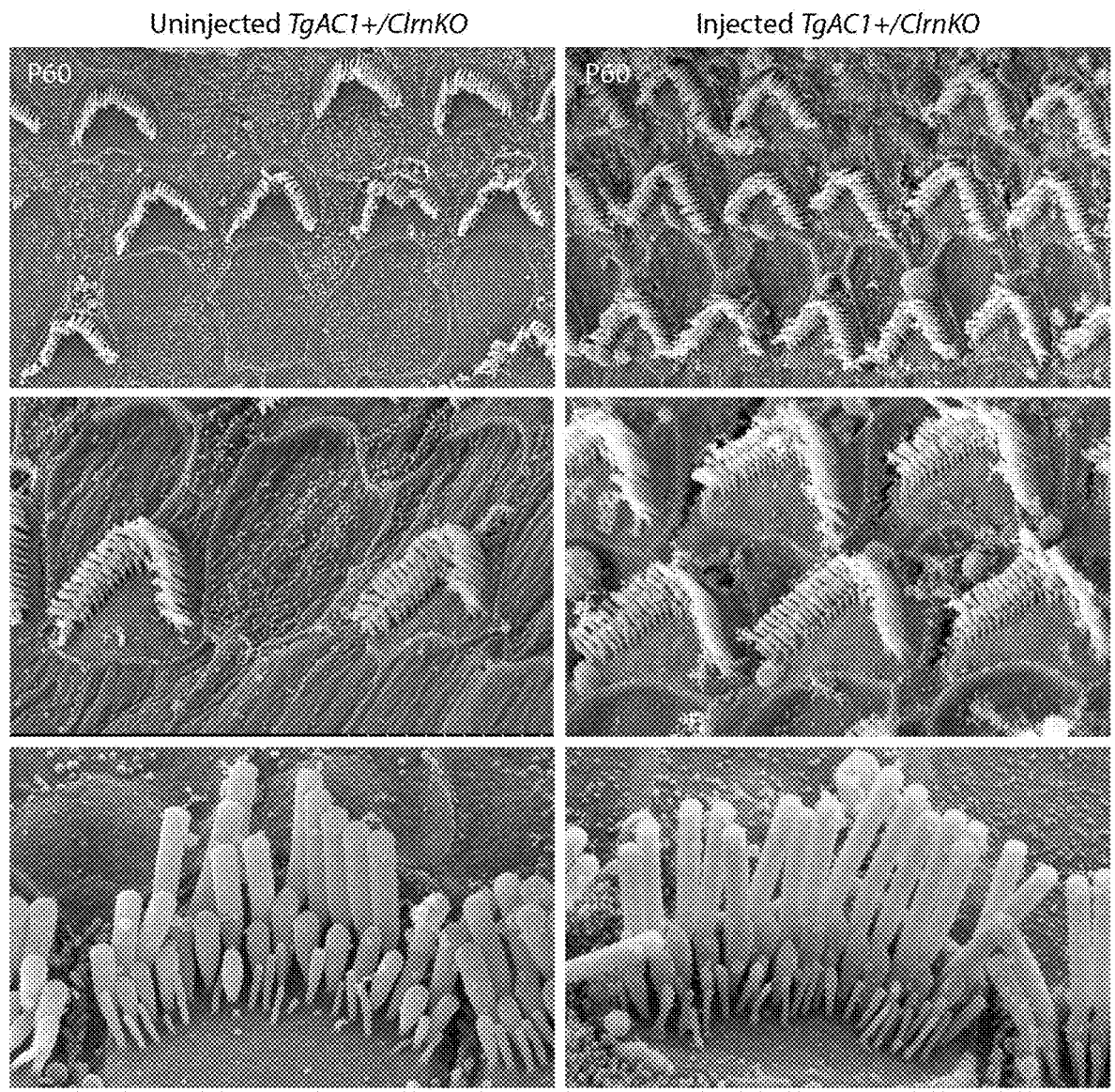
FIG. 4 shows scanning electron microphotographs of the organ of Corti, taken at age P60, from TgAC1+/ClrnKO mice either uninjected or injected with AAV-S-Clrn-opt at P1. Left, Uninjected animals show many missing hair cells and disorganized hair bundles. Right, Injected animals show most hair bundles intact, and normal morphology of hair bundles. Preservation of hair cells indicates long-term rescue of the hearing organ.

Mice at age P60 were evaluated for preservation of hair bundle morphology (FIG. 4). TgAC1/Clrn1-KO mice that were not injected with AAV-S-codon optimized CLRN1 showed widespread loss of hair bundles, and remaining bundles were disorganized. TgAC1/Clrn1-KO mice that were injected with AAV-S-codon optimized CLRN1 showed few missing hair bundles and the bundle had normal morphology.

C57/BL6 mice were also injected at P30 with $2\times10^{10}$ vector genomes (VG) through intravitreal injection. Mice are euthanized at P50, and retinas are dissected and imaged for GFP expression. It is observed that AAV-S is capable of transducing retinal cells such as photoreceptors.

These experiments proved that AAV-S is a useful vector for gene delivery in the inner ear and retina. It enabled transgene expression in the inner ears and retina of mice, particularly in hair cells and photoreceptors affected by the loss of Clarin-1. Further, using AAV-S to deliver an optimized version of Clarin-1 to a mouse model of Usher 3A showed powerful rescue of hearing and vision maintained for at least up to P90.

Example 2

Protein Modeling Suggests that the AAV-S Peptide Insertion in the Variable Region VIII (VR-VIII) Loop of the AAV Capsid is Unlikely to Disrupt Structure An AAV9 capsid variant, AAV-S, was previous identified in a screen for variants that could efficiently target the brain. While AAV-S did not effectively pass the blood-brain barrier, it was highly efficient at targeting peripheral organs. AAV-S contains a 7-amino-acid insert (STTLYSP (SEQ ID NO: 2)) between positions 588 and 589 of the AAV9 VP1 capsid protein (FIG. 6A). This is the same location as the unique insert in AAV9-PHP.B (TLAVPFK (SEQ ID NO: 23)), another variant selected in brain that can efficiently transduce cells in the inner ear. As crystal structures for these variants are unavailable, SWISS-MODEL was used to model the effect of the insertion on the structure of the viral capsid protein (FIG. 6B). As expected, the insertions into the VR-VIII loop do not seem to have a dramatic effect on the protein structure outside of the insertion point. Both AAV-S and AAV9-PHP.B peptides are predicted to form a short loop extending from VR-VIII, but not to affect the structure of the rest of the protein (VR-IV is shown as an example in FIG. 6C). The AAV-S peptide shares some similarity with PHP.B (a single proline and an aromatic residue), but the AAV-S peptide is more polar (STT.S (SEQ ID NO: 24)) than that of PHP.B (T . . . K), while the lysine in PHP.B confers a positive charge that AAV-S lacks.

Figure 7A:
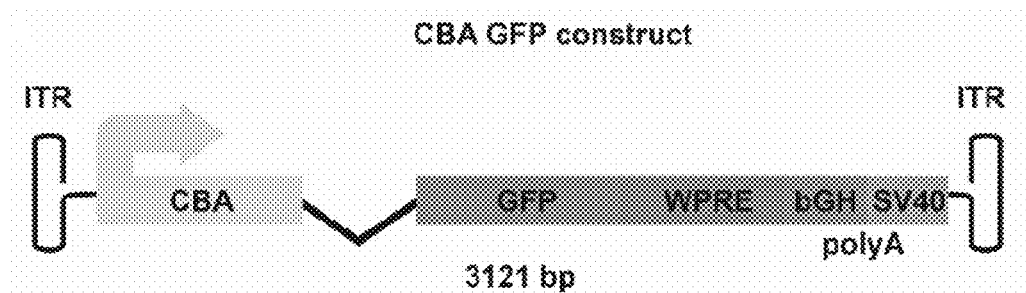
FIGS. 7A-7B show Schematic representation of single-stranded AAV vectors.
Figure 8A:
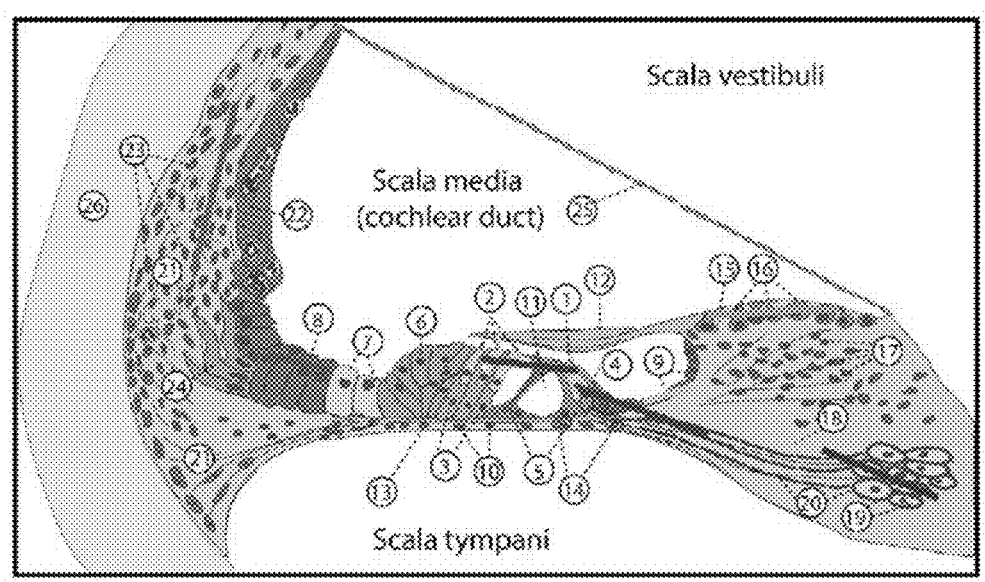
FIGS. 8A-8K show AAV-S efficiently transduces multiple cell types in the neonatal mouse cochlea.
Figure 8B:
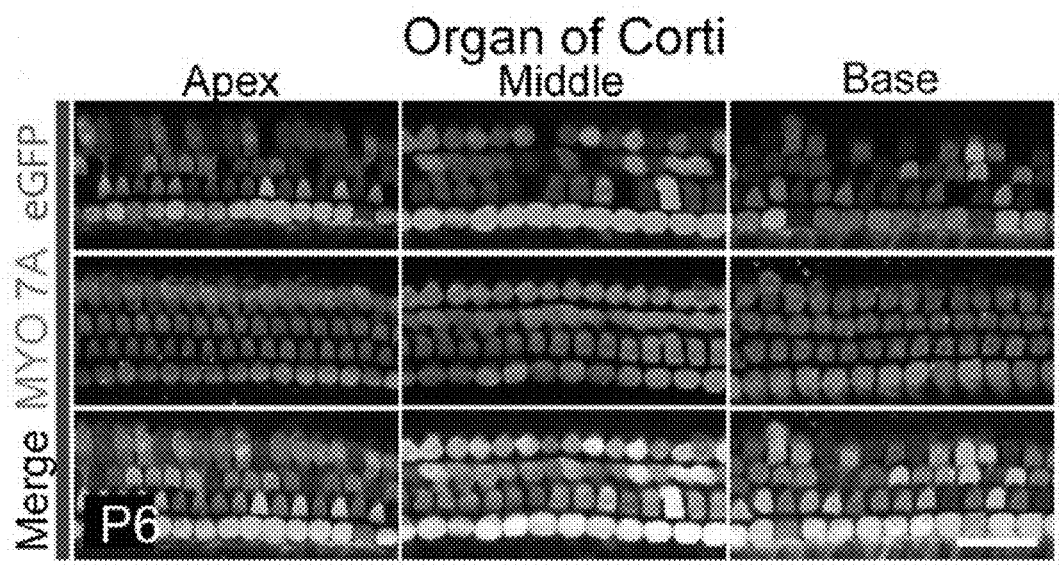
Figure 8C:
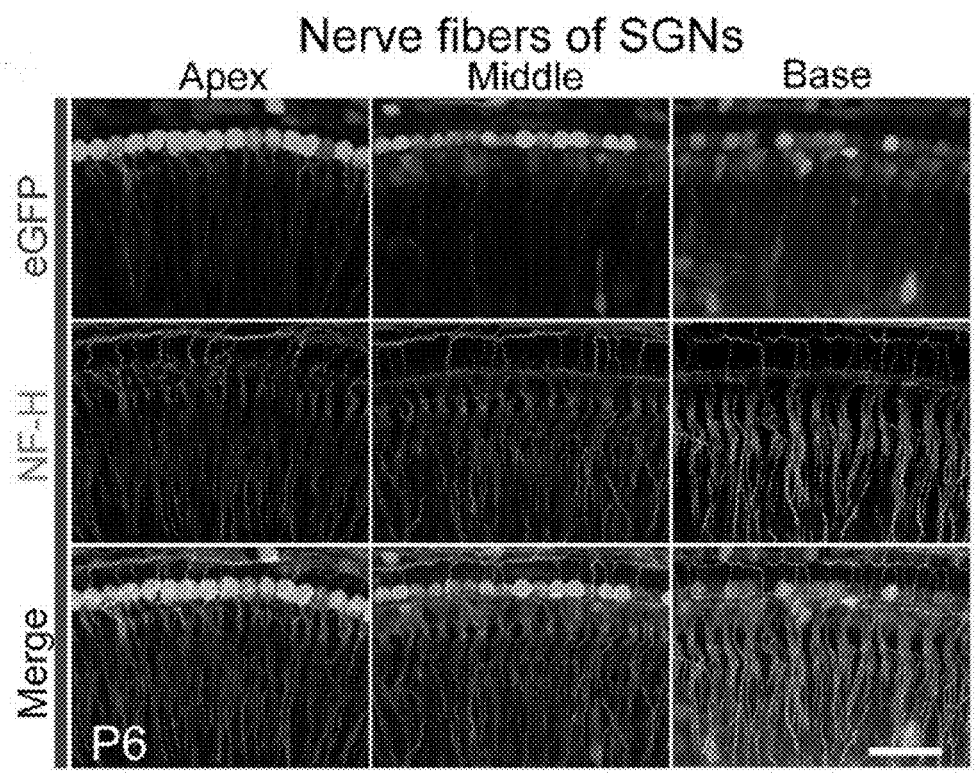
Figure 8D:
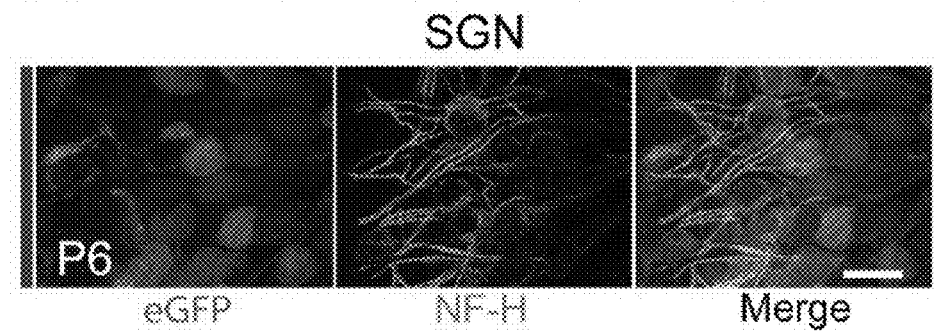
Figure 8E:
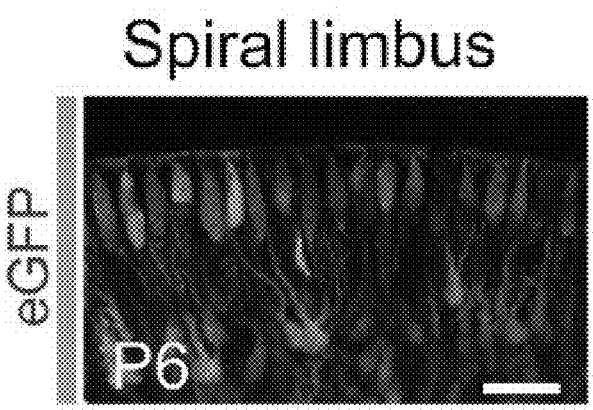
Figure 8F:
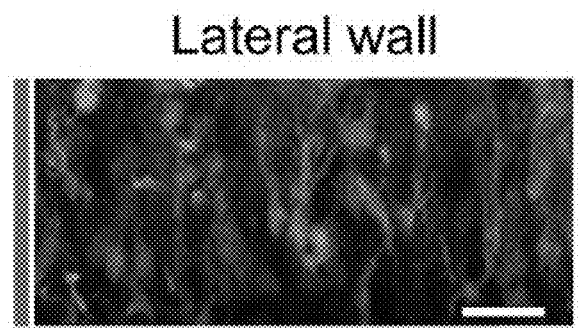
Figure 8G:
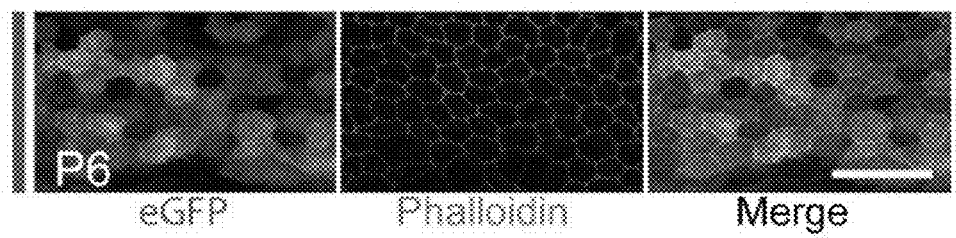
Figure 8H:
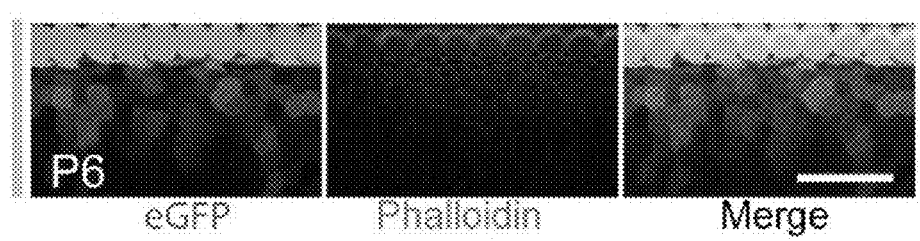
Figure 8I:
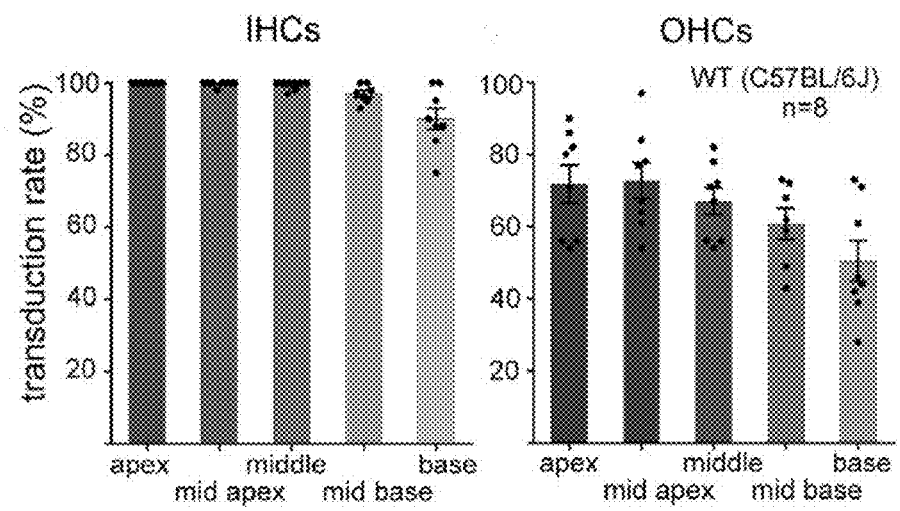
Figure 8J:
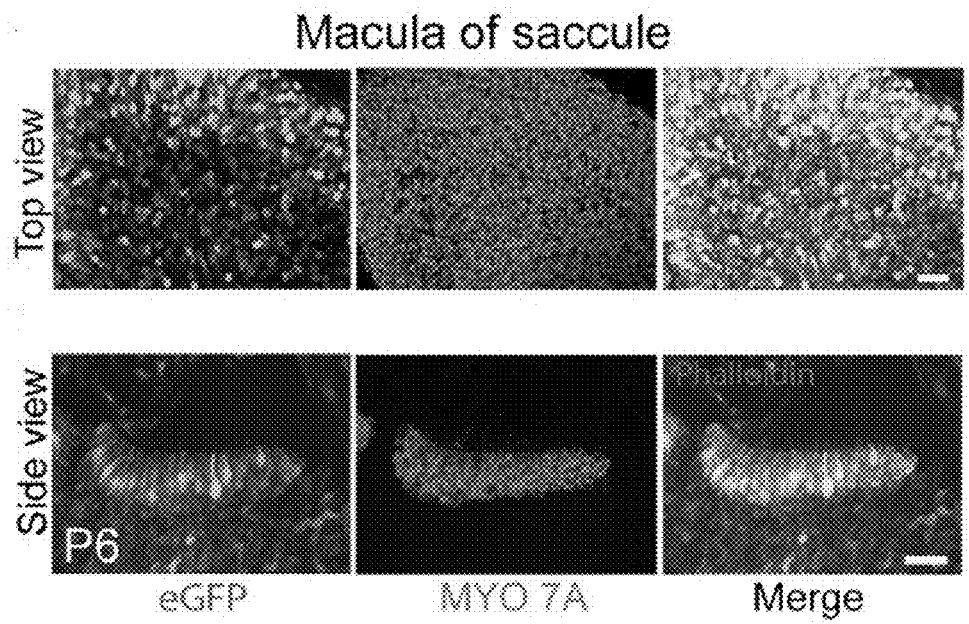

The AAV-S Capsid Mediates Efficient Transgene Expression in a Variety of Cell Types in the Mouse Inner Ear Because AAV-S targets a variety of cell types, whether it transduced cells in the mammalian inner ear was investigated. To gauge the efficacy of AAV-S, a rAAV comprising AAV-S and a vector encoding EGFP (FIG. 7A) under the control of the chicken beta actin (CBA) promoter was injected to the cochleas of wild-type C56BL/6J mice. At postnatal day 1 (P1), mice were injected with $3\times10^{10}$ vector genomes (VG) via the round window membrane (RWM). At P6, cochleas were dissected, immunostained, and imaged (FIGS. 8A-8K). Overall, high levels of transduction throughout the inner ear with AAV-S-CBA-EGFP. In the organ of Corti, a majority of hair cells were transduced, with nearly 100% of IHCs and well over half of OHCs expressing EGFP (FIGS. 8B and 8I). OHC expression varied from apex to base, with ~75% of apical OHCs transduced (reaching up to 100%) versus ~50% of basal OHCs. A similar gradient has been observed for a number of different AAV vectors. The modest transduction in basal OHCs is unlikely to be a consequence of limited vector diffusion, because the basal turn of the cochlea is nearest the injection site and because labeled cells were observed throughout the inner ear. It might reflect a gradient in a capsid receptor or in promoter efficacy.

Aside from hair cells, AAV-S targeted many cell types in the cochlea. In neonatal mice, nerve fibers of SGNs from apex to base were labeled with EGFP (FIG. 8C), as well as SGN cell bodies (FIG. 8D) as confirmed by co-labeling for the neuronal marker neurofilament H (NF-H). Interestingly, transduction in supporting cells, in interdental cells, and in fibrocytes of the spiral limbus (FIG. 8E) and lateral wall (FIG. 8F) was observed, as well as consistent expression in inner and outer sulcus cells and Claudius cells (FIGS. 8G-8H). However, little if any GFP expression was observed in Hensen's cells.

Since the perilymph of the cochlea is continuous with that of the vestibular organs, RWM injection would be a suitable delivery route for targeting vestibular hair cells. Analysis of whole-mount saccular macula samples revealed a wide array of type I and type II hair cells, as well as supporting cells transduced within this vestibular organ (FIG. 8J), further highlighting the efficiency of AAV-S.

Figure 8K:
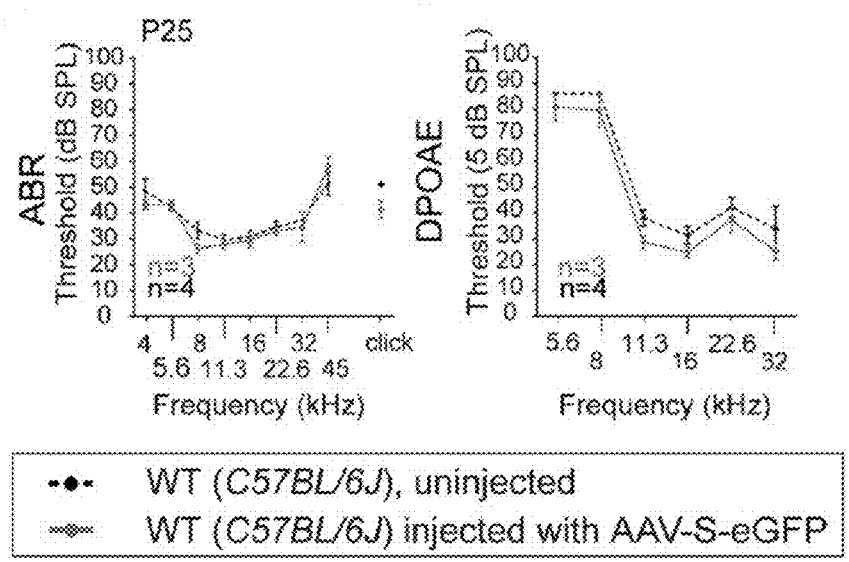

To determine whether vector transduction with AAV-S-CBA-EGFP disrupts auditory function, the auditory brainstem response (ABR) and distortion product otoacoustic emissions (DPOAEs) at P25 was measured in mice that received $3\times10^{10}$ VG of AAV-S-CBA-EGFP at P1. Only mice with confirmed cochlear expression of EGFP were included in the ABR and DPOAE analysis. No significant differences in ABR or DPOAE thresholds for any frequency was found relative to uninjected wild-type mice, confirming that AAV5-mediated EGFP expression did not affect hearing function (FIG. 8K).

Figure 9A:
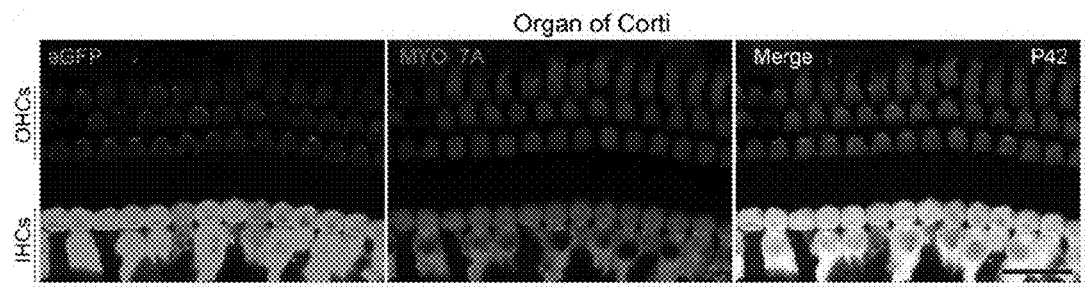
FIGS. 9A-9E show transduction efficiency of AAV-S-CBA-eGFP in C57BL/6J mice after injection into adult posterior semicircular canal. They are Confocal images of whole-mount cochlea and saccule. Animals were injected at P21 with AAV-S-CBA-eGFP ($3\times10^{10}$ VG) via the posterior semicircular canal and the inner ear was dissected and mounted at P42 (n=4).

While high-level transduction of the inner ear can be achieved in neonatal mice, it is often much more challenging in adult mice. To test the efficacy of AAV-S, adult mice were injected with $3\times10^{10}$ VG via the posterior semicircular canal (PSC), and the inner ear was dissected, immunostained, and mounted at P42 (FIGS. 9A-9E). Broad transduction of AAV-S-CBA-EGFP. IHCs were as effective as in other studies, but while most OHCs were transduced, expression levels were extremely weak (FIG. 9A). There was no detectible transduction in supporting cells of the organ of Corti.

Figure 9B:
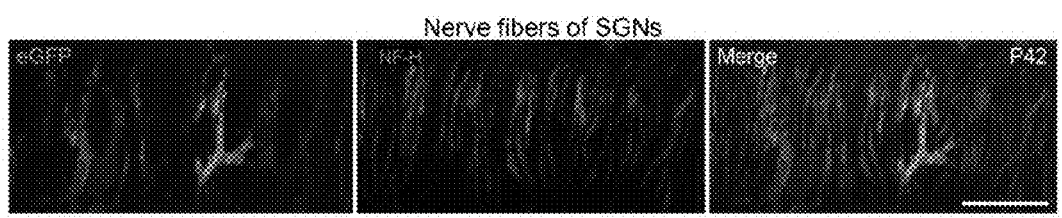
Figure 9C:
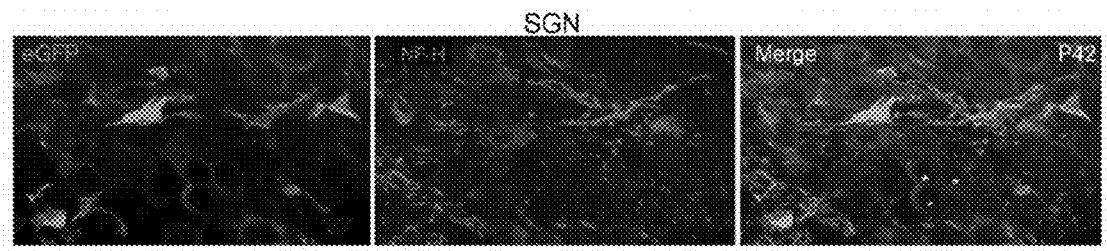
Figure 9D:
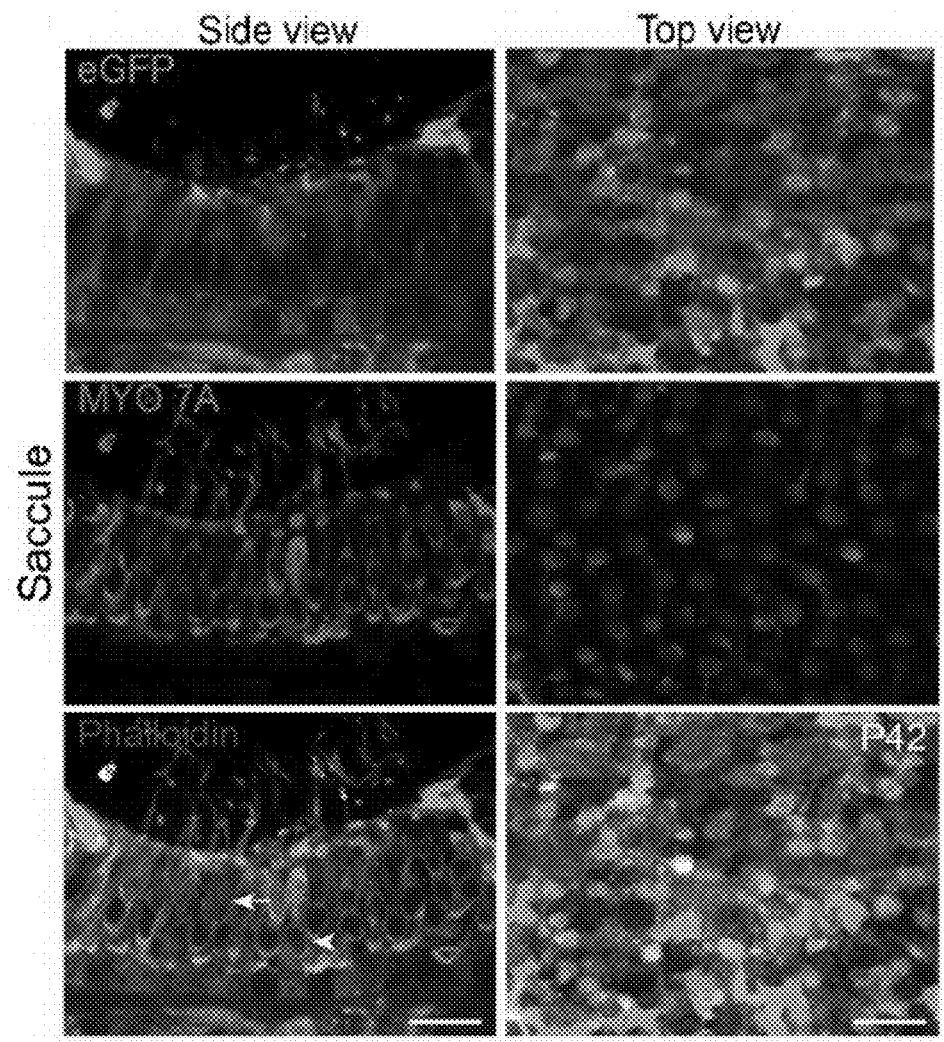
Figure 9E:
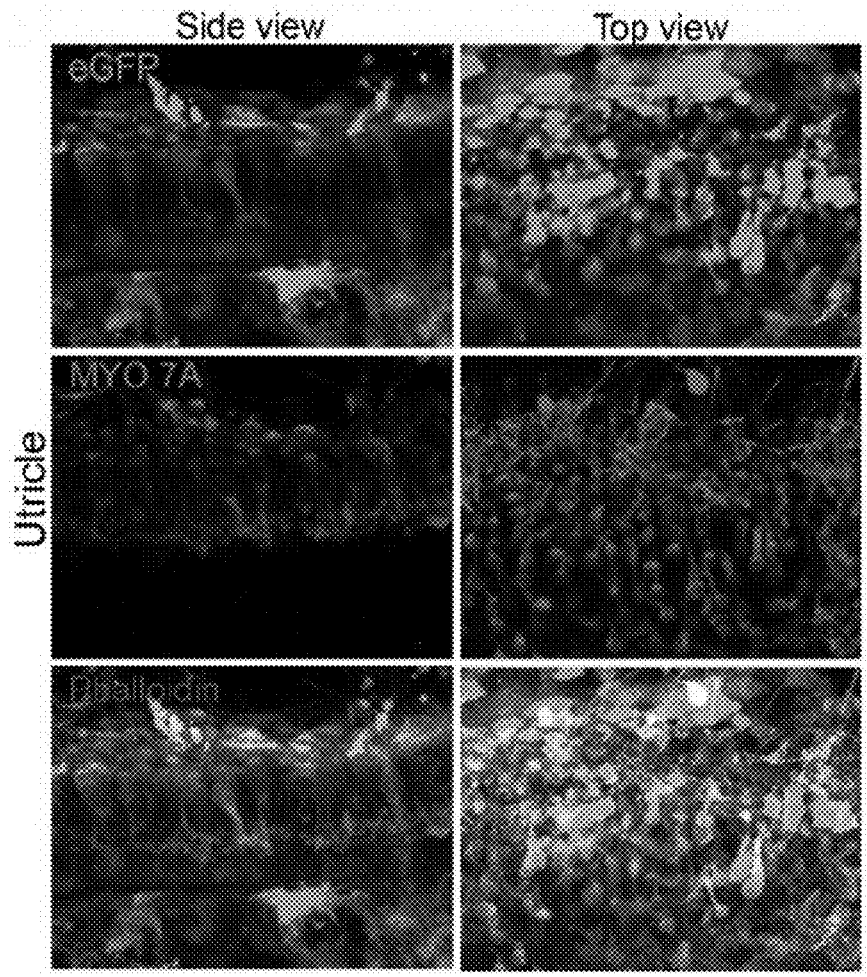

Images of whole mounts immunostained for the neuronal marker NF-H were analyzed and high transduction in satellite glial cells of SGNs and fibrocytes were observed, but no transduction was observed in SGNs and nerve fibers of SGNs (FIGS. 9B-9C). A high level of EGFP expression also was detected in hair cells and supporting cells throughout the saccule and utricle (FIGS. 9D-9E).

Figure 7B:
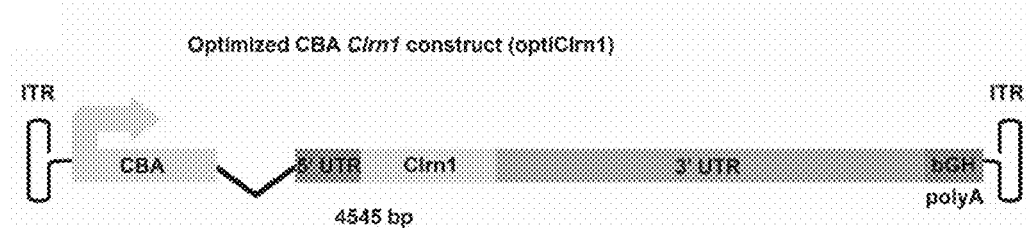

AAVS-CBA-optiClrn1 Mediates Robust and Durable Rescue of Hearing in the TgAC1+/ClrnKO Mouse Model of Usher 3A In order to gauge the clinical relevance of AAV-S-mediated transgene delivery, a therapeutic construct was tested in a mouse model of deafness. Usher syndrome type 3A is caused by recessive mutations in the CLRN1 gene, encoding the small four-pass transmembrane protein clarin-1, and features a relatively late onset of symptoms, with deafness developing as late as the second decade of life. A homozygous Clrn1 knockout mouse model)(Clrn1$^{KO/KO}$) that also incorporates a transgene that transiently expresses Clrn1 under the control of the Atoh1 promoter (TgAC1+). By delaying the loss of CLRN1, this mouse more accurately mimics the phenotype in humans. A mouse codon-optimized Clrn1 coding sequence flanked by 50 and 30 UTRs, under the control of the CBA promoter (optiClrn1; FIG. 7B) was packaged into AAV-S capsid.

Figure 10A:
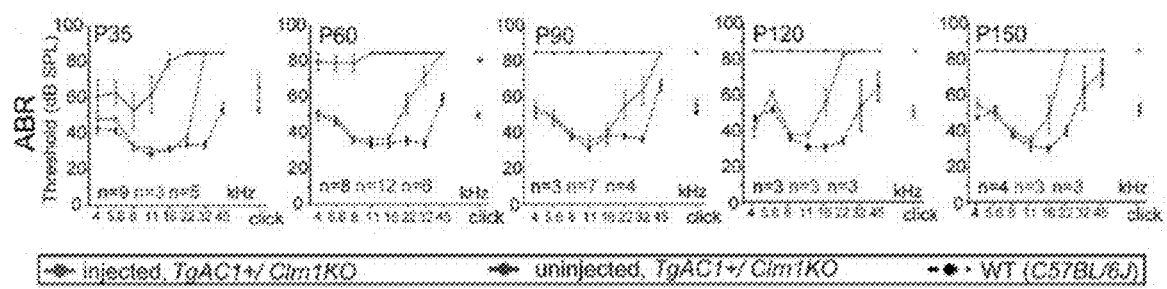
FIG. 10A-10H show AAV-S-optiClrn1 delivery robustly and durably rescues hearing and morphology of hair bundles and auditory nerve fibers in the TgAC1$^+$/ClrnKO mouse model of Usher 3A.
Figure 10B:
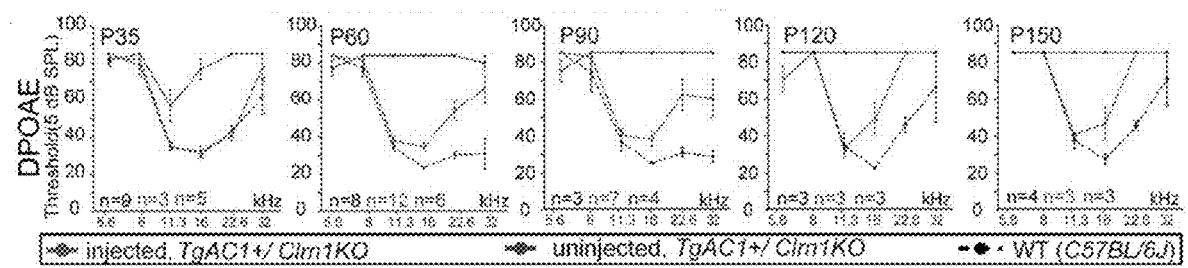
Figure 10C:
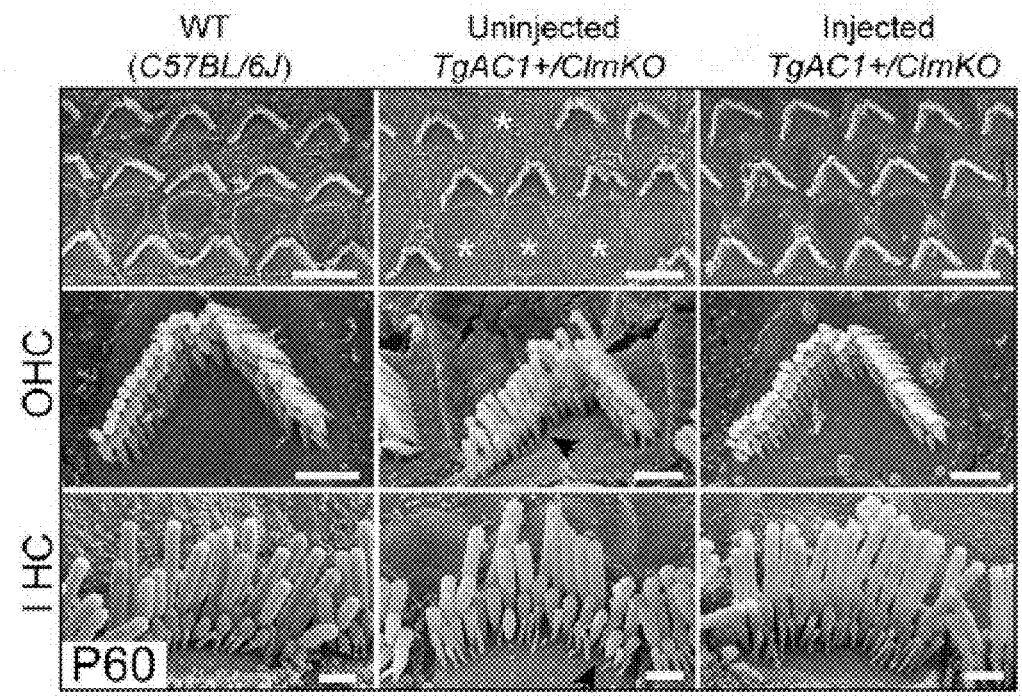
Figure 10D:
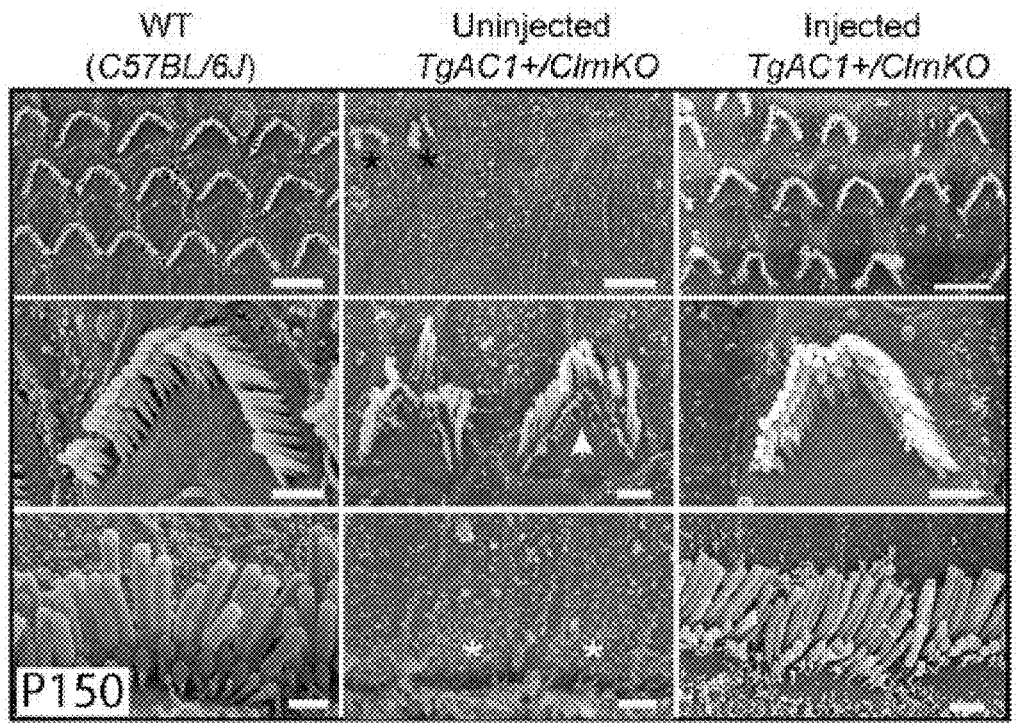

Knockout mice carrying the transgene (TgAC1+/ClrnKO) were injected at P1 with $1.9\times10^{10}$ VG of AAV-S-optiClrn1 and their ability to hear at ages P30, P60, P90, P120, and P150 was assayed (FIGS. 10A-10B). The untreated TgAC1+/Clrn1KO mice progressively lost hearing and were deaf (threshold above 85 dB, the highest tested) by P90. In treated mice, a striking rescue of hearing when tested with both ABR and DPOAE (FIGS. 10A-10B) was found. ABR showed that TgAC1+/ClrnKO mice treated with AAV-S-optiClrn1 had hearing as sensitive as wild-type mice at low and middle frequencies. This rescue persisted to P150 (FIG. 10A). Hearing at a high frequency (22.6 kHz) was significantly better in treated than in untreated TgAC1+/ClrnKO up to P90 (FIG. 10A). DPOAEs showed a similar pattern, with robust rescue across all frequencies at P30-P90 and a weakening at high frequencies at age P120-P150 (FIG. 10B). DPOAE amplitude measured at a representative mid-range frequency (11.3 kHz) showed rescue to wild-type level in TgAC1+/ClrnKO mice treated with AAV-S-optiClrn1, while untreated TgAC1+/ClrnKO mice had no detectable DPOAEs (FIG. 10G). Wild-type mice injected with AAV-S-optiClrn1 showed no difference in ABR or DPOAE when compared with uninjected controls, suggesting that the surgery and vector expression were well tolerated (FIG. 10H).

Clrn1 Delivery with AAV-S Rescues Morphology of Hair Bundles and Auditory Nerve Fibers in the TgAC1+/ClrnKO Mouse Model of Usher 3A To better understand the AAV-S-mediated rescue of hearing, scanning electron microscopy at P60 and P150 in untreated wild-type and TgAC1+/ClrnKO mice and in mice treated at P1 with $1.9\times10^{10}$ VG of AAV-S-optiClrn1 were performed. Scanning electron microscopy revealed that wild-type C57BL/6J mice had well-organized hair bundles in IHCs and OHCs (FIGS. 10C-10D). In untreated TgAC1+/ClrnKO mice, both IHC and OHC hair bundles showed a loss of short-row stereocilia (FIG. 10C, middle column, black arrow) at P60, and some hair bundles were missing entirely (FIG. 10C, middle column, white asterisk). The degeneration progressed: whereas wild-type mice showed good bundle morphology at P150 (FIG. 10D), most hair cells were gone by P150 in TgAC1+/ClrnKO mice (FIG. 10 D, middle column), with just a few patches of surviving OHCs (FIG. 10D, middle column, black asterisk). Even those were severely disorganized and showed loss of short- and middle-row stereocilia (FIG. 10D, middle column, white arrow). In contrast, TgAC1+/ClrnKO mice injected with AAV-S-optiClrn1 displayed robust rescue of hair bundle morphology at all tested ages FIG. 10C, right column and FIG. 10D, right column).

Figure 10E:

Phalloidin staining of hair bundle actin also showed that untreated TgAC1+/ClrnKO mice had disorganized bundles in OHCs, with loss of short and middle stereocilia rows and preservation of only the tallest row (FIG. 10E). Similarly, Clrn1 delivery with AAV-S into TgAC1+/ClrnKO mice fully rescued the morphology of OHCs, with bundles appearing like those observed in wild-type C57BL/6J mice at P90 (FIG. 10E).

Figure 10F:
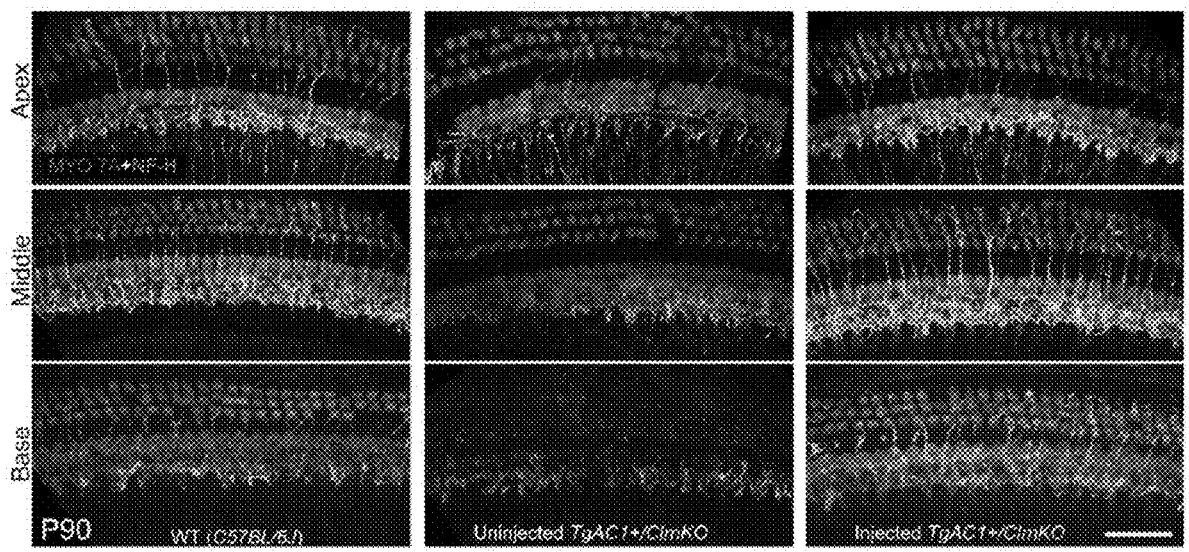
Figure 10G:
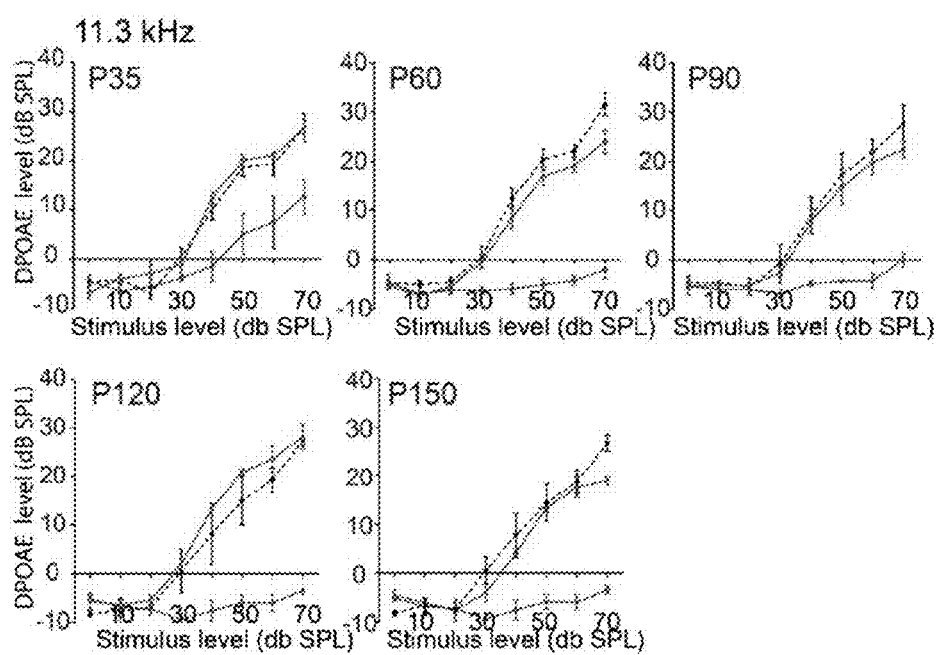
Figure 10H:
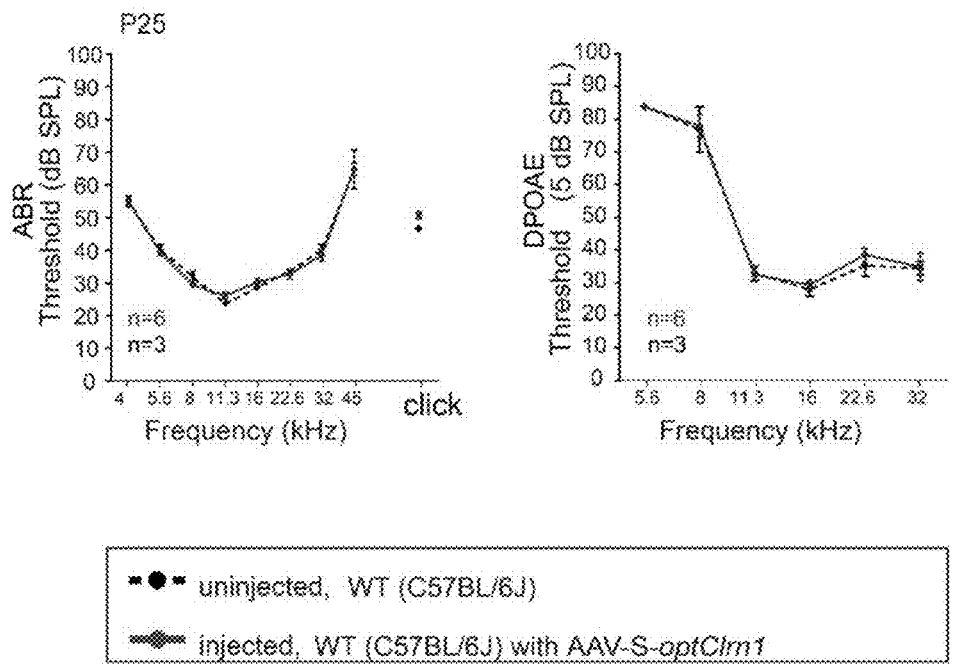

Innervation of hair cells in treated and untreated animals at P90—an age when untreated TgAC1+/ClrnKO mice were deaf—were also evaluated using immunofluorescence to observe hair cells with anti-MYO7A and nerve fibers with anti-NF-H. TgAC1+/ClrnKO mice had a significant loss of auditory nerve fibers across the cochlea and total loss of hair cells in the basal region of the cochlea compared to wild-type controls (FIG. 10F). TgAC1+/ClrnKO mice injected at P1 with AAV-S-optiClrn1 showed no detectible loss of hair cells or nerve fibers compared to wild-type C57BL/6J mice (FIG. 10F).

AAV-S Mediates Efficient Transgene Expression in the NHP Inner Ear

Larger animals such as NHPs provide a much more relevant model for transgene delivery to the human inner ear. An effective surgical approach for delivering AAV vectors to the inner ears of cynomolgus monkeys was previously reported. The method was used to test whether AAV-S can transduce the cochleas of NHPs in this study, using the same EGFP reporter cassette as in the mouse. Three cynomolgus monkeys (*Macaca fascicularis* were injected. The first received AAV-S-EGFP via RMW injection in one ear ($5.8 \times 10^{11}$ VG). For the two other monkeys, two cochleas were injected with another "high" dose ($4.7 \times 10^{11}$ VG), a third with a "low" dose ($8 \times 10^{10}$ VG), and the last with phosphate-buffered saline (PBS). Three weeks post-injection, animals were euthanized. Cochleas were extracted from the temporal bones of animals, further trimmed, and decalcified in 10% EDTA for ~2 weeks. These cochleas were either whole-mounted or embedded in optimal cutting temperature (OCT) compound and cryosectioned. All cochleas were stained with anti-EGFP antibodies, as well as for markers of various cell types.

Anti-EGFP immunostaining at low magnification revealed broad transduction throughout the NHP organ of Corti (FIGS. 11A-11H). Almost all cell types of the cochlea were transduced at the high doses (see schematics in FIG. 11F and FIG. 12B; linking to Table 1).

TABLE 1

Relative transduction efficiency of AAV-S-CBA-EGFP in neonatal and adult mice and NHPs

| Region | Cell type | Neonatal mouse | Adult mouse | NHP |
|---|---|---|---|---|
| | Organ of Corti | | | |
| 1 | IHCs | +++ | +++ | +++ |
| 2 | OCHs | +++ | ++ | +++ |
| 3 | Deiters' cells | +++ | − | +++ |
| 4 | inner phalangeal cells | +++ | − | +++ |
| 5 | pillar cells | +++ | − | +++ |
| 6 | Hensen's cells | − | − | +++ |
| 7 | Claudius cells | ++ | + | +++ |
| 8 | outer sulcus cells | +++ | + | +++ |
| 9 | inner sulcus (border) cells | +++ | +++ | +++ |
| 10 | fibrocytes of basilar membrane | +++ | +++ | +++ |
| 11 | tunnel | − | − | − |
| 12 | tectorial membrane | ++ | +++ | +++ |
| 13 | basilar membrane | − | − | − |
| 14 | spiral vessels | nd | nd | nd |
| 15 | spiral limbus | | | |
| 16 | interdental cells of spiral limbus | +++ | +++ | +++ |
| 17 | fibrocytes of spiral limbus | +++ | +++ | +++ |
| 18 | nerve fibers | ++ | − | − |
| 19 | spiral ganglion neurons | +++ | − | − |
| 20 | glial cells | +++ | ++ | +++ |
| 21 | lateral wall | | | |
| 22 | stria vascularis | nd | + | + |
| 23 | fibrocytes of spiral ligament | +++ | +++ | +++ |
| 24 | root cells | nd | nd | +++ |
| 25 | epithelial cells of Reissner's membrane | +++ | +++ | +++ |
| 26 | bone | | | |
| | Saccule and utricle | | | |
| | vestibular hair cells | +++ | ++ | +++ |
| | vestibular supporting cells | +++ | +++ | − |
| | Scarpa's ganglion neurons | +++ | − | − |
| | glial cells | +++ | ++ | +++ |

CBA is a broadly active promoter.
Efficiency graded as follows: −, <1%; +, 1%-20%; ++, 20%-50%; +++, >50%;
nd, not determined.

Figure 11A:
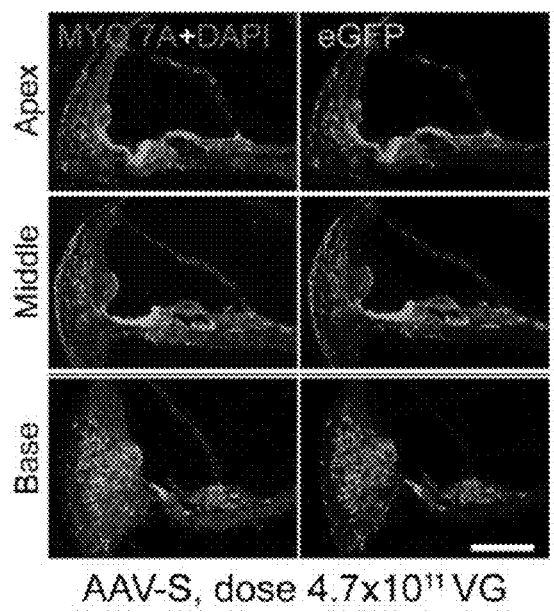
FIGS. 11A-11I show AAV-S mediates robust transgene expression in a variety of cell types in the NHP cochlea and saccule.
Figure 11B:
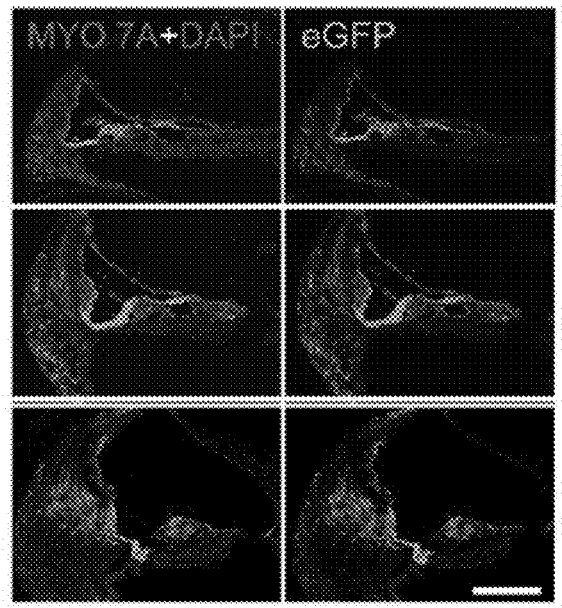
Figure 11C:
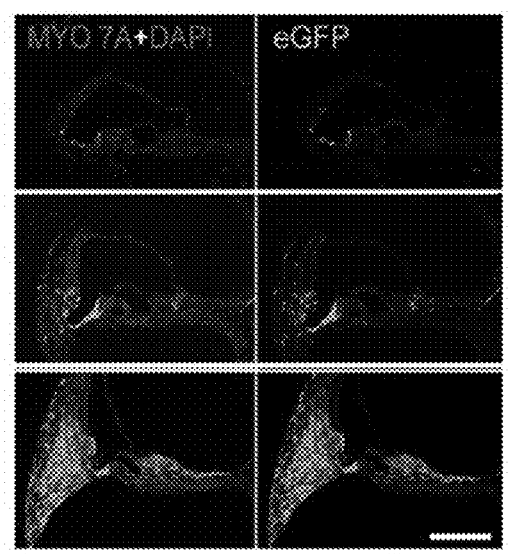
Figure 11D:
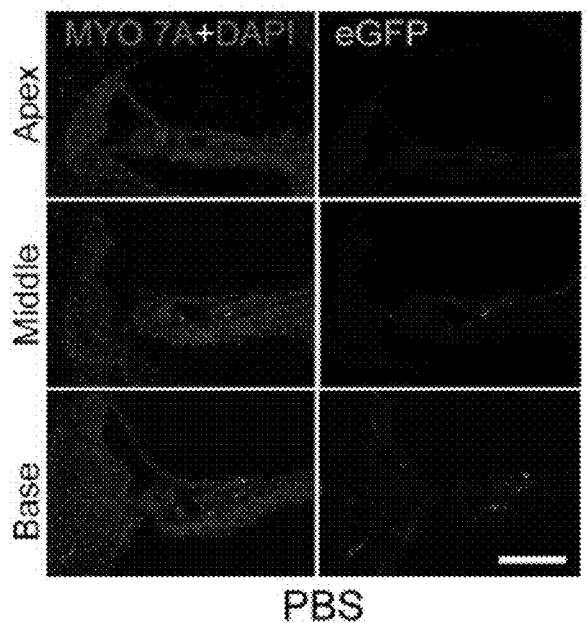
Figure 11E:
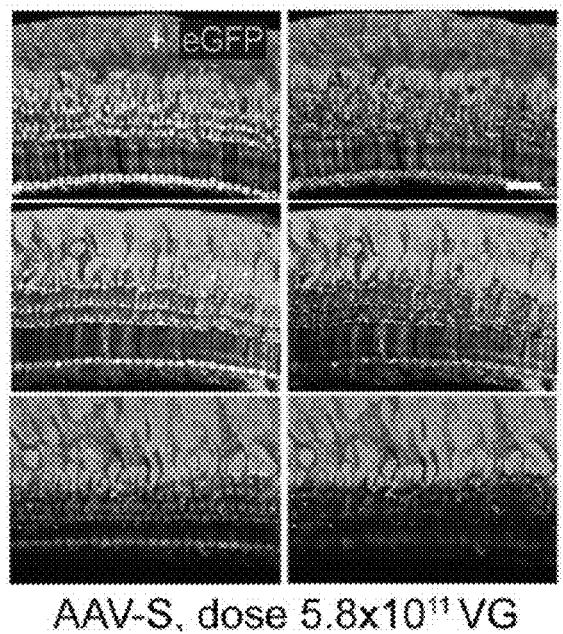
Figure 11F:
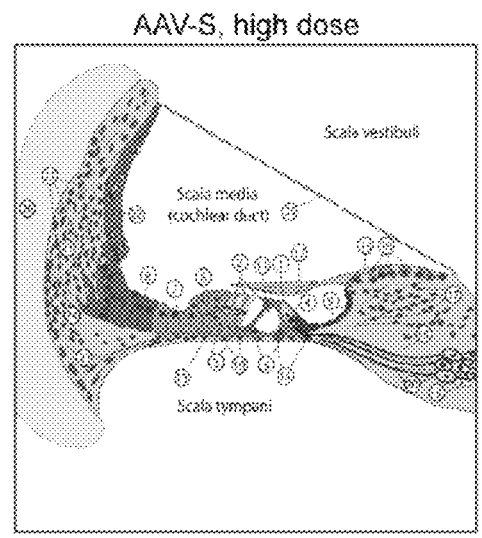

In particular, a very high level of EGFP expression in the organ of Corti, outer and inner sulcus cells, spiral limbus, lateral wall, and Reissner's membrane (FIGS. 11A, 11B and 11E) was observed. The low-dose ($8 \times 10^{10}$ VG) cochlea showed a greatly reduced transduction efficiency in all cells of the cochlea with the exception of the lateral wall, spiral limbus, and outer sulcus epithelium in the base, which had good transduction (FIG. 11C). No specific signal was observed in the cochlea injected with PBS (FIG. 11D and FIG. 11I).

Figure 11I:
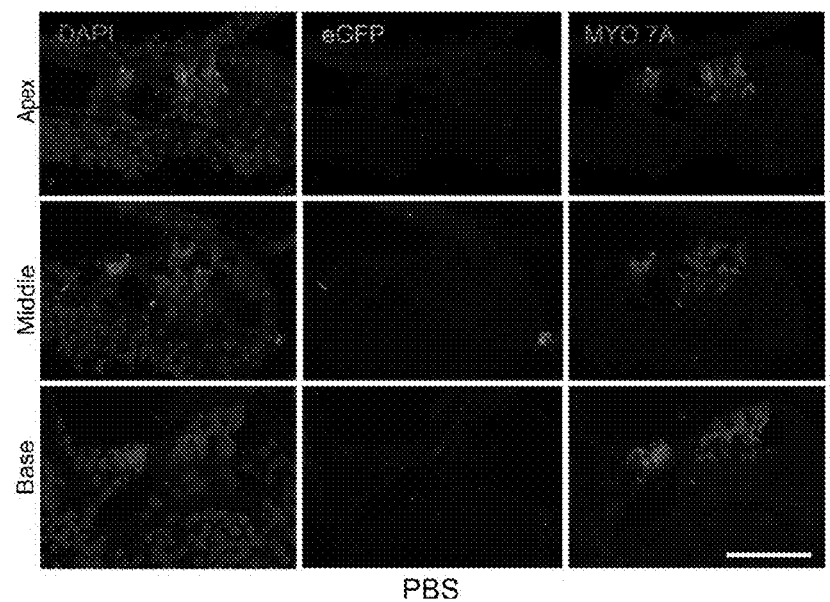
Figure 12A:
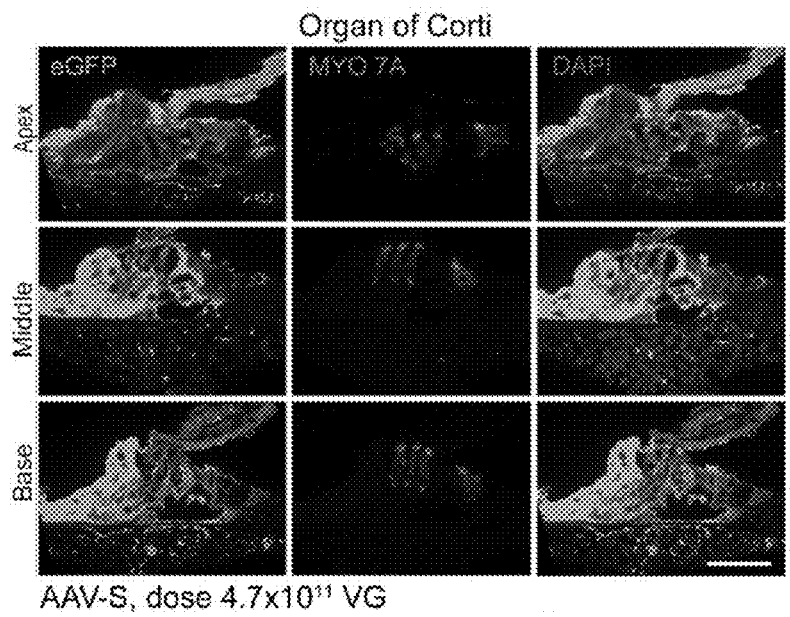
FIGS. 12A-12F show robust transgene expression is observed in the organ of Corti and vestibule in NHPs injected with AAV-S-CBA-EGFP.
Figure 12B:
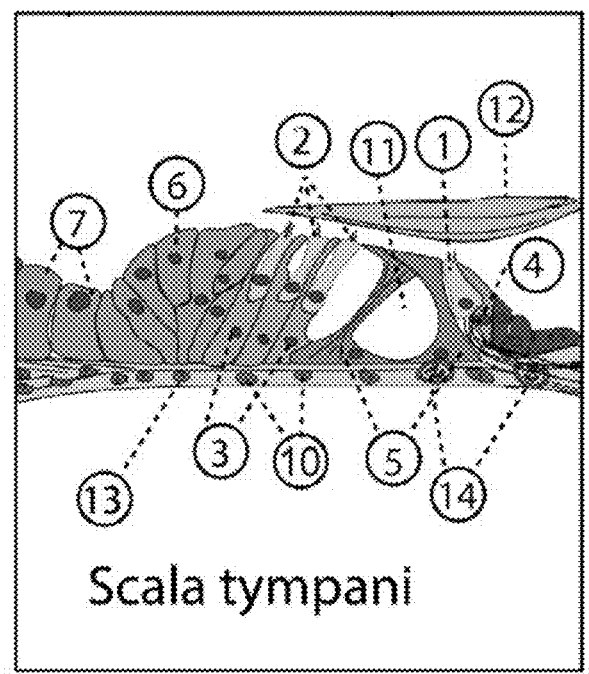
Figure 12C:
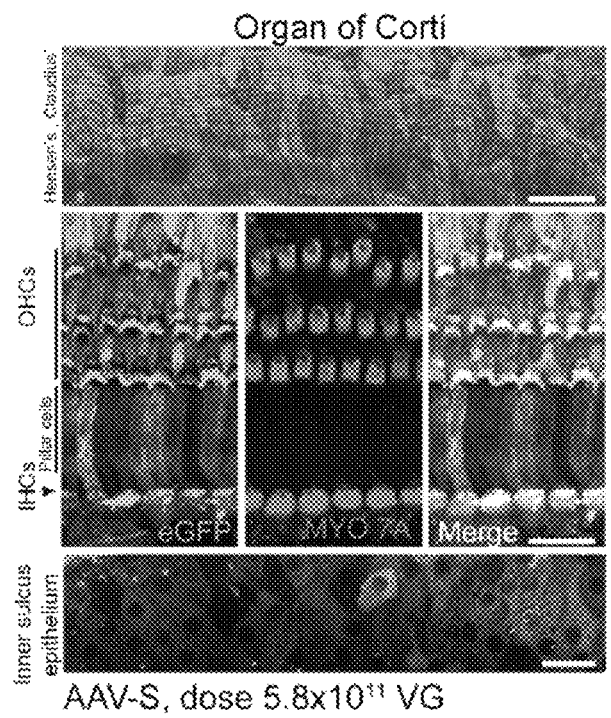
Figure 12D:
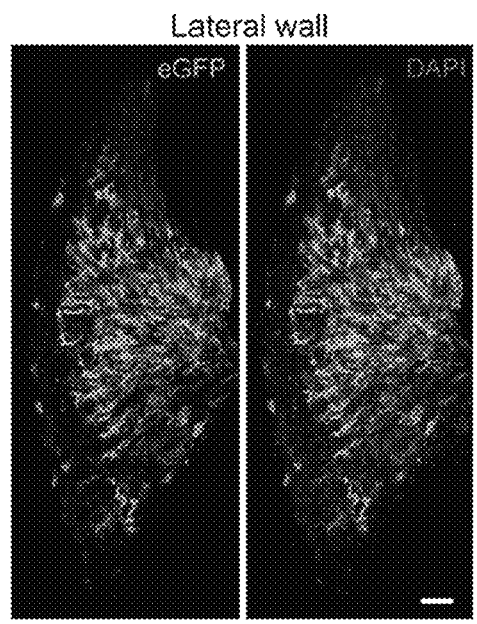
Figure 12E:
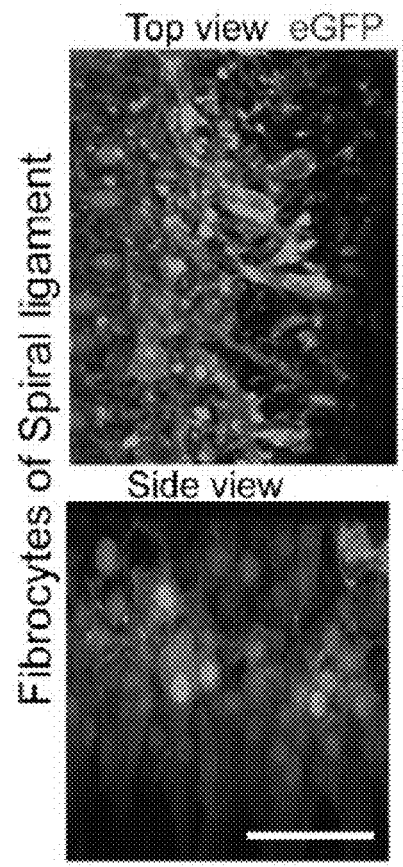
Figure 13A:
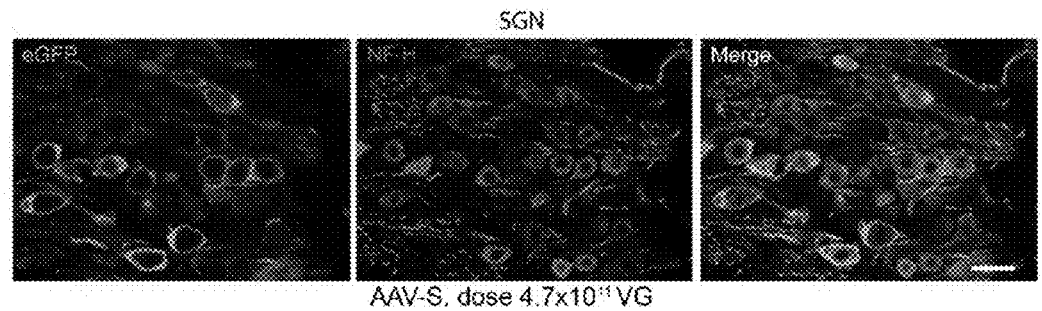
FIGS. 13A-13B show spiral ganglion and Scarpa's ganglion in an NHP ear injected with AAV-S-CBA-eGFP. NHP ear injected with AAV-S-CBA-eGFP ($4.7 \times 10^{11}$ VG) and immunostained with anti-eGFP and anti-NF-H.

Higher-magnification images of the organ of Corti from base to apex were analyzed (FIG. 12A and FIG. 12C, top and bottom panel). In the cochleas administrated with the highest doses ($4.7 \times 10^{11}$ and $5.8 \times 10^{11}$ VG) the hair cells, Deiters' cells, inner phalangeal cells, pillar cells, Hensen's, and Claudius cells appeared to be completely transduced (FIGS. 12A-12C). Epithelial cells of the inner sulcus, as well as basilar membrane fibrocytes, were also highly transduced (FIGS. 12A, 12B and 12C bottom panel). The spiral ligament of the lateral wall revealed significant transduction in fibrocytes (FIGS. 12D-12E). Notably, high magnification images from the modiolus region of the cochlea injected with $4.7 \times 10^{11}$ VG showed high EGFP expression in satellite glial cells and Schwann cells, but almost no transduction of SGNs (FIG. 13A). No specific signal was observed in the organ of Corti injected with PBS (FIG. 11I).

Figure 11G:
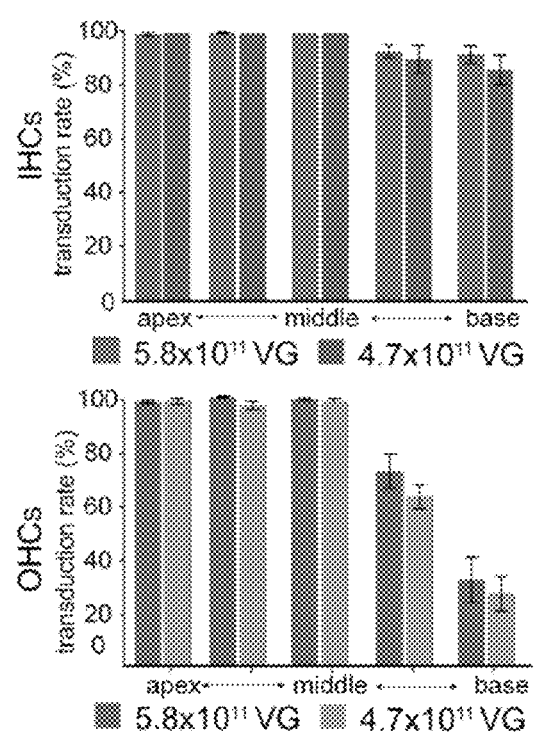

Quantification of vector transduction efficiency in IHCs and OHCs in a cochlea injected with $5.8 \times 10^{11}$ VG of AAV-S-CBA-EGFP and analyzed with whole-mount imaging showed that at the high dose, AAV-S transduced nearly 100% of both IHCs and OHCs in the apical, mid-apical, and middle regions (FIG. 11G). The transduction remained at 100% in IHCs but showed a decrease in OHCs to 70% in the mid-base region and 30% in the basal region of the cochlea. The same pattern of transduction was observed in ears injected with $4.7\times10^{11}$ VG of AAV-S-CBA-EGFP (FIG. 11G).

Figure 11H:
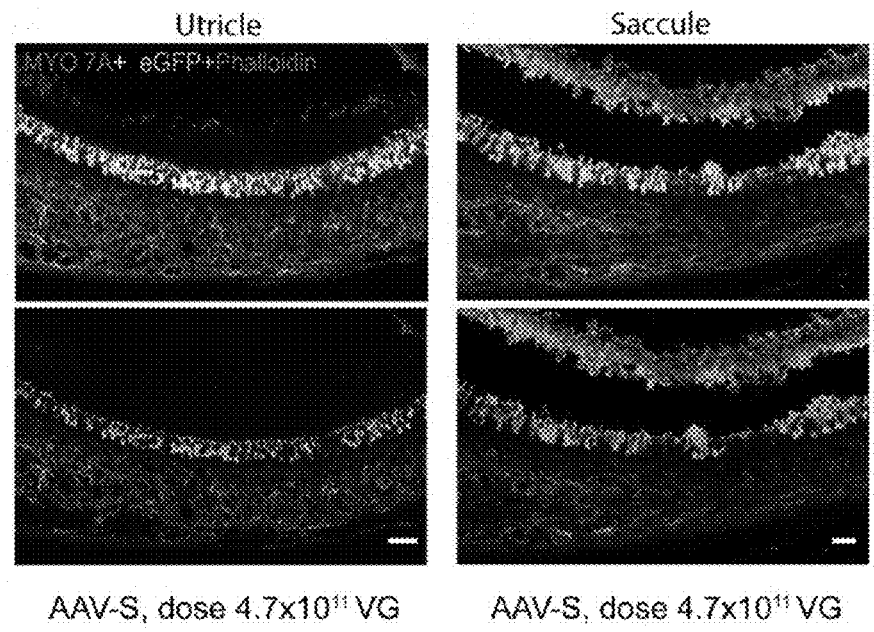
Figure 12F:
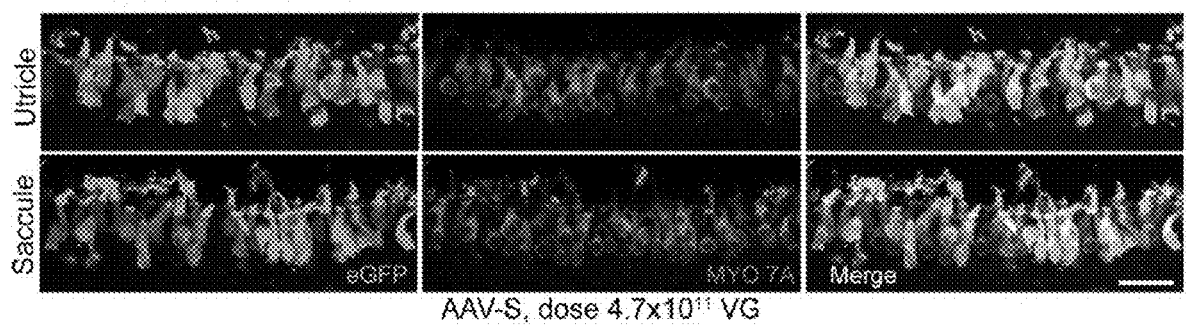

Some forms of genetic deafness also cause vestibular dysfunction. Since the cochlear perilymph is continuous with perilymph that fills the vestibular labyrinth, whether AAV-S-CBA-EGFP injected via the RWM would transduce vestibular sensory organs in NHPs and could be a useful vector for gene delivery into human vestibular organs was investigated. Indeed, immunofluorescence images of frozen sections of vestibular epithelia injected with $4.7\times10^{11}$ VG of AAV-S-CBA-EGFP revealed robust EGFP expression of the saccule and utricle, the vestibular organs sensitive to gravity and linear head movements (FIG. 11H). Analysis of high-magnification images from the saccule and utricle revealed robust EGFP expression in both type I hair cells (flask shaped with an enveloping post-synaptic calyx) and type II hair cells (cylindrical with punctate synapses) (FIG. 12F).

Figure 13B:
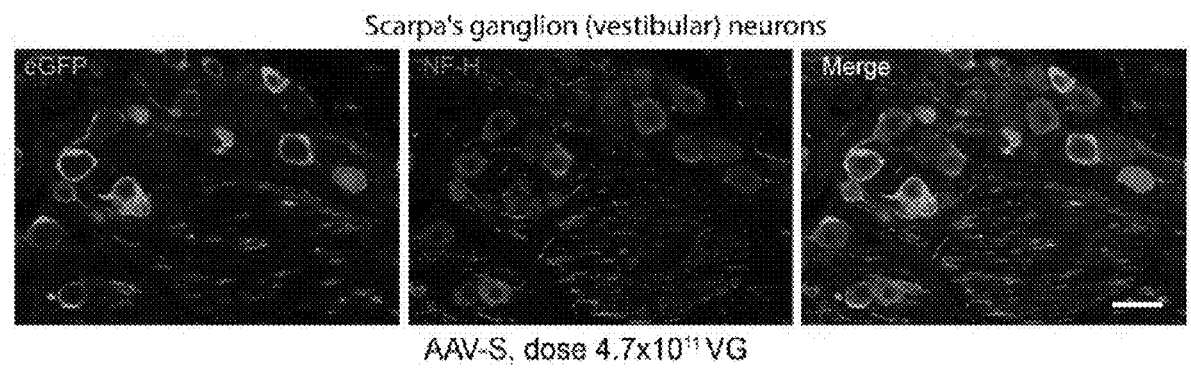

High-magnification images of Scarpa's ganglion (vestibular) neurons in the ear injected with $4.7\times10^{11}$ VG were also analyzed. Labeling was similar to that in spiral ganglion: high EGFP expression in satellite glial cells and Schwann cells with almost no detectable transduction of vestibular neurons (FIG. 13B).

Histopathological Analysis of NHPs Injected with AAV-S-CBA-EGFP

Figure 14A:
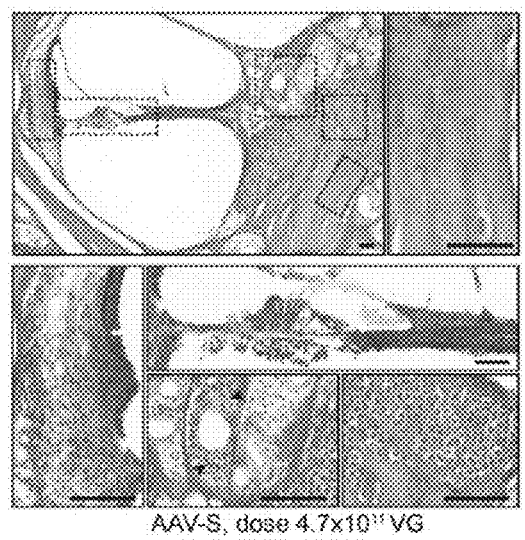
FIGS. 14A-14B show NHPs injected with AAV-S-CBA-EGFP show minimal immune infiltration in the inner ear.
Figure 14B:
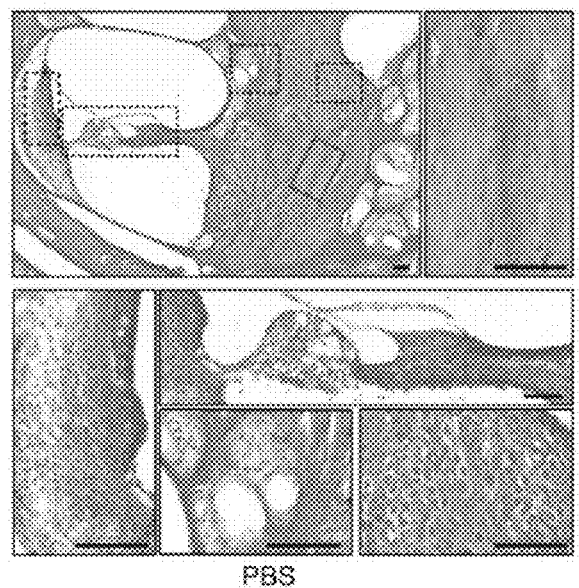

Hematoxylin and eosin (H&E)-stained frozen tissue sections from injected and uninjected cochleas to assess pathology were analyzed. Normal tissue morphology and architecture appeared to be preserved in both treated and untreated groups, with no notable abnormalities (FIGS. 14A-14B). Slight immune infiltration in treated cochleas was observed (FIG. 14A) that was not seen in PBS-injected cochlea (FIG. 14B). Specifically, perivascular mononuclear cell infiltration was present in the modiolus region, and not in the organ of Corti, spiral limbus, or lateral wall. This infiltration was focal and did not appear to prevent the expression of EGFP. Minor changes associated with surgery and vector injection and dissection were observed in all cochleas.

ABR Test of NHPs Injected with AAV-S-CBA-EGFP

Figure 15A:
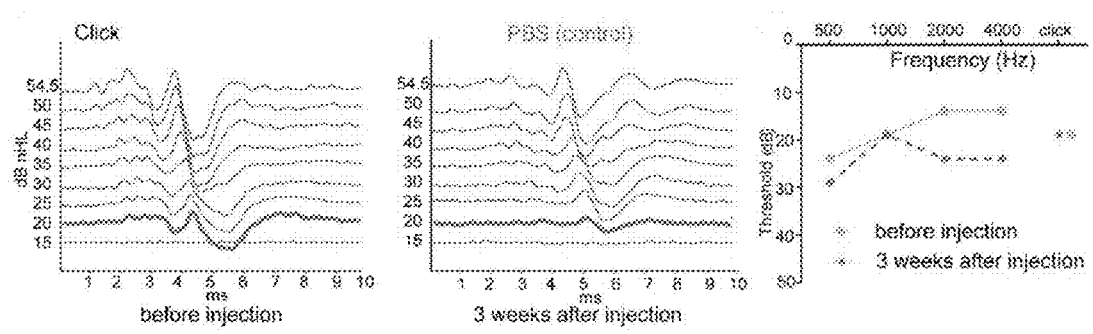
FIG. 15A-15D show ABR testing of NHPs before and after injection of AAV-S-CBA-EGFP showed no loss of sensitivity for most injections NHPs were tested with click and tone ABR before AAV-S vector injection or PBS control injection and then three weeks later before euthanasia.

ABR thresholds were tested in 4 ears of two cynomolgus monkeys, before and 3 weeks after the injections (FIGS. 15A-15D). The pre-injection normal threshold (mean±SD) for click ABR was 16.2±2.5 dB normal hearing level (nHL); thresholds for 500 Hz, 1,000 Hz, 2,000 Hz, and 4,000 Hz pure tones were 25±4.1, 18.8±4.8, 11.3±2.5, and 13.8±2.5 dB nHL, respectively. Pre-injection thresholds to thresholds 3 weeks after injection to assess changes that may be due to the vector were compared. In the PBS-injected cochlea, no difference was seen in the click ABR threshold after injection (FIG. 15A). In the pure tone ABR, there was a small (10 dB) reduction in sensitivity at the two higher frequencies, likely attributable to the injection procedure itself (FIG. 15A, middle panel).

Figure 15B:
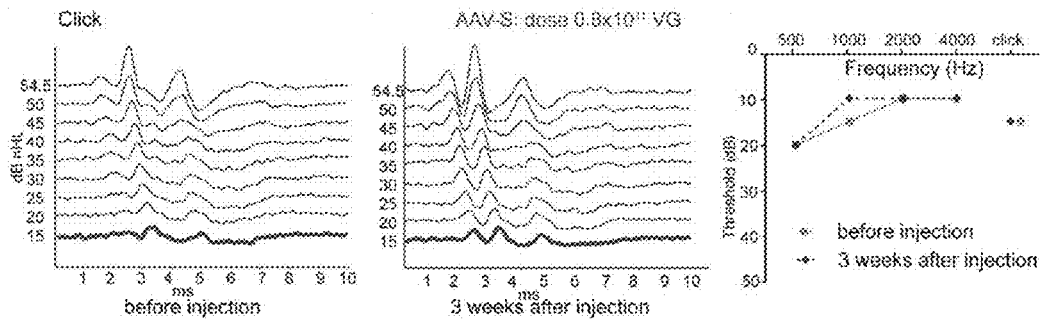
Figure 15C:
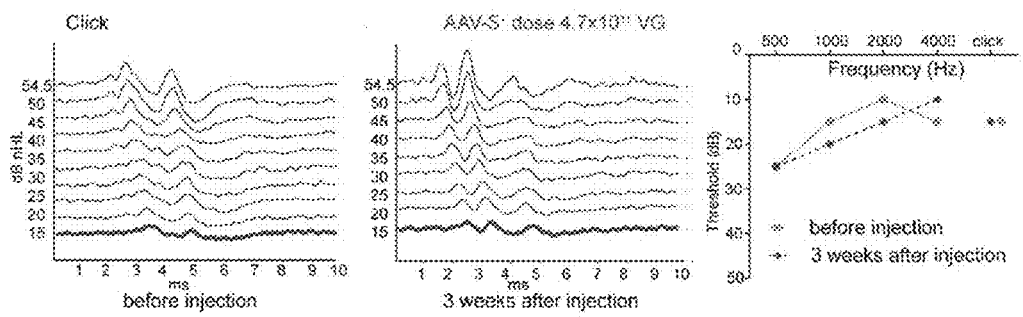
Figure 15D:
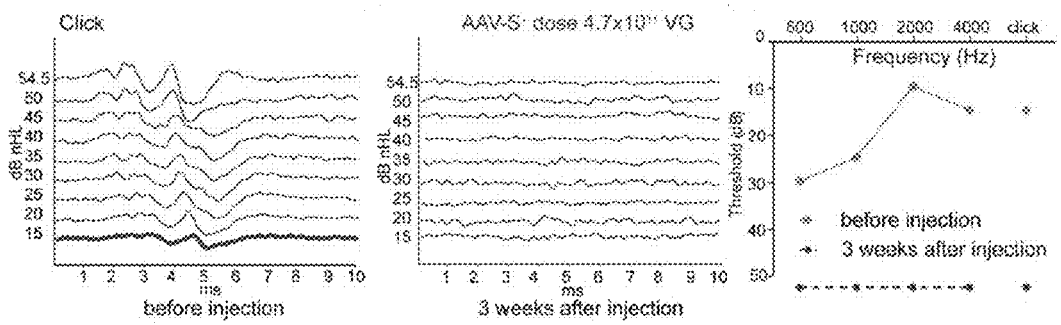

In the low-dose cochlea ($8\times10^{10}$ VG; FIG. 15B), no change in sensitivity in either click or tone ABR was observed, so the injection procedure does not reproducibly cause a loss of sensitivity. Similarly, in one high-dose cochlea ($4.7\times10^{11}$ VG; FIG. 15C), there was no systematic change in sensitivity, so the vector seems not to show toxicity. However, in the other high-dose cochlea ($4.7\times10^{11}$ VG; FIG. 15D), hearing was lost altogether. Because the same vector dose did not damage hearing in the other cochlea (FIG. 15C), it is unlikely to be a consequence of the vector but may have been due to mastoid surgery complications such as effusion into the middle ear, which can result in transient conductive hearing loss.

Material and Methods

AAV Vector Production, Purification, Titration, and Endotoxin Testing

An AAV plasmid carrying a single-stranded EGFP cassette was used as previously described. EGFP was driven by a hybrid cytomegalovirus immediate-early enhancer/chicken beta-actin (CBA) promoter and contained a woodchuck hepatitis virus post-transcriptional regulatory element (WPRE) and SV40 and bovine growth hormone (BGH) poly(A) sequences, flanked by AAV2 inverted terminal repeats (ITRs).

The clarin-1 AAV expression construct (optiClrn1) contained a short (172 bp) 50 UTR, a mouse codon-optimized Clrn1 coding sequence (isoform 2), and a long (2.1 kb) 30 UTR. Expression was driven by a CBA promoter, and the construct contained a BGH poly(A) sequence.

AAV production was performed as previously described. In brief, HEK293T cells were triple transfected (calcium phosphate method) with (1) AAV rep/cap plasmid encoding AAV2 rep and AAV9 capsid sequence with the AAV-S peptide insert immediately following the nucleotide trio encoding amino acid 588 of VP1; (2) an adenovirus helper plasmid, pAdDF6; and (3) the AAV expression plasmid with the ITR-flanked transgene expression cassette. Cell lysates were harvested 68-72 h post-transfection and purified by iodixanol density gradient ultracentrifugation. Iodixanol was removed and buffer exchanged to PBS using Zeba desalting columns, 7 kDa molecular weight cutoff (MWCO; Thermo). Vector was concentrated from 4 mL to approximately 100 µL using 2 mL Amicon Ultra 100 kDa MWCO ultrafiltration devices. Vector titers in VG/mL were determined by Taqman qPCR in an ABI Fast 7500 real-time PCR system (Applied Biosystems) using probes and primers to the BGH poly(A) signal and an AAV plasmid standard curve. Endotoxin levels of AAV preparations used in NHP experiments were determined using an Endosafe nexgen-PTS instrument and Endosafe LAL cartridges (Charles River Laboratories). All vector preparations used in NHP studies contained <1.0 EU/mL. Vectors were pipetted into single-use aliquots and stored at −80° C. until use.

Mouse Breeding and Housing

Animal handling, breeding, and all procedures were performed in compliance with NIH ethics guidelines and with a protocol approved by the Animal Care Committee. Mice were housed and bred at the animal facility. In this study, C57BL/6J mice were used as the wild-type mice, and all the wild-type control material was obtained from this genetic background. C57BL/6J P1 pups were used for AAV-S-CBA-EGFP transduction experiments. TgAC1$^+$/Clrn1KO mice were bred. Genotyping was done as previously described.

Neonatal Mouse RWM Injection

The RWM injections were performed under a stereomicroscope (Nikon SMZ1500). P1 pups were anesthetized using hypothermia by exposure on ice and then kept on an ice pack during the procedure. Injections were done via the RWM as previously described. For EGFP expression experiments, 1.5 µL of AAV-S-CBA-EGFP vector solution ($3\times10^{10}$ VG) was injected with a micropipette needle at a rate of 150 nL/min using a Nanoliter 2000 Injector (World Precision Instruments). For Clrn1-mediated rescue experiments, 1.2 µL of AAV-S-optiClrn1 viral particle solution ($1.9\times10^{10}$ VG)

was injected with a micropipette needle at a rate of 60 nL/min. Standard postoperative care was applied after the injection.

Adult Mouse Posterior Canal (PSC) Injections

Adult mouse PSC injections were done as described previously with modifications. C57BL/6J P21 mice were anesthetized with ketamine (100 mg/kg) and xylazine (10 mg/kg) through intraperitoneal injection. GenTeal lubricant eye gel was applied to protect the cornea. After the fur behind the left ear was shaved, the surgical area was cleansed with an antiseptic solution. The area was isolated with sterile drapes and swabbed along the proposed incision with 10% povidoneiodine. A 10- to 15-mm postauricular skin incision was made. After exposing the facial nerve and the sternocleidomastoid muscle by blunt dissection, the tissue covering the temporal bone was retracted. A small 35 G hole was made in the PSC, and then a 35 G blunt needle was inserted into the opening. A viral suspension of AAV-S-CBA-EGFP (1.5 µL; dose $3\times10^{10}$ VG) at 150 nL/min was injected using the Nanoliter 2000 Injector (World Precision Instruments). The hole was filled in with tissue and sealed with glue. The wound was closed with 7-0 vicryl-coated sutures and swabbed with 10% povidone-iodine. The mouse was placed on a heating pad until full recovery. Animals received an intraperitoneal injection of meloxicam (5 mg/kg body weight) after surgery and once more within the first 24 h. Injected mice were checked daily for 5 days following surgery.

Mouse Cochlear Histology and Imaging

In experiments where transduction efficiency of AAV-S-EGFP was detected via its intrinsic fluorescence, organ of Corti explants or utricle and saccule were dissected at P6 in L-15 medium and fixed with 4% formaldehyde in Hank's balanced salt solution (HBSS) for 1 h, washed three times with HBSS, and then blocked and permeabilized with 10% donkey and 10% goat serum with 0.3% Triton X-100 for 1 h at room temperature. Rabbit polyclonal anti-MYO7A antibody (Proteus Biosciences) was used to label hair cells, and chicken anti-neurofilament-H antibody (Millipore) was used to label nerve fibers and SGNs. They were diluted 1:500 in 10% donkey/10% goat serum supplemented with 0.1% Triton X-100/PBS and incubated overnight at room temperature followed by several rinses in HBSS. Next, samples were incubated in blocking solution for 30 min and incubated overnight at room temperature with a donkey anti-rabbit immunoglobulin G (IgG) secondary antibody conjugated to Alexa Fluor 593 in a 1:500 dilution in blocking solution or with a goat anti-chicken IgG secondary antibody conjugated to Alexa Fluor 593 in a 1:500 dilution in blocking solution. To label hair bundle actin, we used phalloidin conjugated to Alexa Fluor 405 (1:20; Life Technologies).

In experiments where the transduction efficiency of AAV-S-EGFP was assessed in the adult cochlea, the intrinsic EGFP signal was amplified with anti-EGFP antibodies. Dissected in L-15 medium, cochleas were immediately fixed with 4% formaldehyde in HBSS for 1 h at room temperature, then washed with HBSS and transferred to fresh 10% EDTA for 2 days. After samples were fully decalcified, the organs of Corti were micro dissected, blocked, and permeabilized with 10% donkey/10% goat serum with 0.5% Triton X-100 for 1 h at room temperature. Samples were then stained with rabbit monoclonal anti-EGFP (Thermo Fisher) and chicken anti-Neurofilament-H (Millipore) antibodies or with rabbit polyclonal anti-MYO7A (Proteus Biosciences) and chicken anti-EGFP (Ayes) antibodies. They were diluted 1:500 in 10% donkey/10% goat serum supplemented with 0.1% Triton X-100/PBS and incubated overnight at 4° C. temperature followed by several rinses in HBSS. Next, samples were incubated in blocking solution for 30 min at room temperature and incubated overnight at room temperature with a donkey anti-rabbit IgG secondary antibody conjugated to Alexa Fluor 488 and with a goat anti-chicken IgG secondary antibody conjugated to Alexa Fluor 593, or with a donkey anti-rabbit IgG secondary antibody conjugated to Alexa Fluor 593 and with a goat anti-chicken IgG secondary antibody conjugated to Alexa Fluor 488, in a 1:500 dilution in blocking solution. To label hair bundle actin, phalloidin-Alexa Fluor 405 was used.

In rescue experiments of TGAC1$^+$/ClrnKO P90 mice, the protocol above was used to assess changes in hair cells and nerve fibers. Rabbit polyclonal anti-MYO7A (Proteus Biosciences) and chicken anti-neurofilament-H (Millipore) antibodies were used at 1:500 dilution. To label hair bundle actin, phalloidin-Alexa Fluor 405 was used. Tissues were mounted on a Colorfrost glass slide (Thermo Fisher Scientific) using Prolong Gold Antifade mounting medium (Thermo Fisher Scientific). Imaging was performed with a Nikon Ti2 inverted spinning disk confocal using a Plan Apo λ20×/0.8 objective, Plan Fluor 40×/1.3 oil objective, Plan Apo λ60×/1.4 oil objective, or Plan Apo λ100×/1.45 oil objective.

Quantification of Transduction Efficiency in Neonatal Mice

Whole-mount cochleas, immunostained as described, were imaged with a Nikon Ti2 inverted spinning disk confocal using a Plan Fluor 40×/1.3 oil objective. Five different regions (apex, mid-apex, middle, mid-base, and base) along the cochlea were imaged and transduced cells quantified. The laser intensity was chosen based on the specimen with the strongest EGFP signal to prevent fluorescence saturation, and the same settings were then used for each image of a set. The efficiency of IHC and OHC transduction was evaluated by two blinded investigators using the ImageJ program (NIH Image). HCs were identified with immunolabeling for MYO7A. Control samples without AAV were used to exclude autofluorescence. Segments with dissection-related damage were removed from the analysis.

Scanning Electron Microscopy

Adult mice (P60 and P150) were anesthetized with an intraperitoneal injection of ketamine (100 mg/kg)-xylazine (10 mg k/g). Mice were decapitated after they no longer responded to painful stimuli. Cochleas were extracted in L-15 medium. The stapes from the oval window was removed and the RWM punctured with fine forceps. Under a stereomicroscope, a small hole was made in the apex of the cochlea using a 27 G needle connected to a 1-mL syringe. Cochleas then were immediately fixed with a mixture of 1% glutaraldehyde/4% formaldehyde in 0.1 M cacodylate buffer (pH 7.2), supplemented with 2 mM CaCl2 for 1 h at room temperature. Additionally, samples were gently and slowly perfused with 1% glutaraldehyde/4% formaldehyde solution via the round and oval windows until the solution washed out of the small hole at the apex. Then, samples were post-fixed with 2.5% glutaraldehyde in 0.1 M cacodylate buffer (pH 7.2), supplemented with 2 mM CaCl2 for 1 h at room temperature. Samples were rinsed in 0.1 M cacodylate buffer (pH 7.2) and then in distilled water. After peeling cochlear bone with the 27 G needle, the organ of Corti was micro dissected and the tectorial membrane was pulled out. Then, samples were immersed in a saturated aqueous solution of 1% osmium tetroxide for 1 h in the dark, washed with water, and postfixed with 1% tannic acid aqueous solution for 1 h in the dark. Samples were rinsed in distilled water. The osmium-tannic steps were repeated once more. Samples were rinsed in distilled water, dehydrated in an ascending series of ethanol, and critical-point dried from liquid CO2 (Tousimis Autosamdri 815). Samples were then mounted on aluminum stubs with carbon conductive tabs and were sputter-coated with 5-nm platinum and observed in a field-emission scanning electron microscope (Hitachi S-4700).

ABR and DPOAE Testing

ABRs and DPOAEs were recorded using an EPL acoustic system (Massachusetts Eye and Ear, Boston, MA, USA) in an acoustically and electrically shielded room. Adult mice (from P25 to P150) were anesthetized with an intraperitoneal injection of ketamine (100 mg/kg)-xylazine (20 mg/kg) cocktail and placed on a temperature-controlled heating pad set to 37° C. for the duration of the experiment. Acoustic stimuli were delivered via a custom acoustic assembly consisting of two electrostatic drivers as sound sources and a miniature microphone at the end of a probe tube to measure sound pressure in situ. ABRs were recorded using three subdermal needle electrodes: reference electrode in the scalp between the ears, recording electrode just behind the pinna, and ground electrode in the back near the tail.

For ABRs, 5-ms tone-pip stimuli with a 0.5 ms rise-fall time at frequencies from 5.6-45.2 kHz were delivered in alternating polarity at 30 s$^{-1}$. The response was amplified (×10,000), band-pass filtered (0.3-3 kHz), and averaged (×512) with a PC-based data acquisition system using the Cochlear Function Test Suite software package (Massachusetts Eye and Ear, Boston, MA, USA). Sound levels were incremented in 5-dB steps, from ~20 dB below threshold up to 80 dB sound pressure level (SPL). ABR Peak Analysis software (v1.1.1.9, Massachusetts Eye and Ear, Boston, MA, USA) was used to determine the ABR thresholds. ABR thresholds were confirmed by visual examination, as the lowest stimulus level in which a repeatable waveform could be observed. DPOAEs were recorded for primary tones (frequency ratio $f_2/f_1=1.2$, level ratio L1=L2+10), where $f_2$ varied from 5.6 to 45.2 kHz in half-octave steps. Primary tones were swept in 5 dB steps from 10 to 80 dB SPL (for $f_2$). DPOAE threshold was determined from the average spectra as the $f_1$ level required to produce a DPOAE of 5-dB SPL.

NHP Study Design

Three juvenile male cynomolgus monkeys (*Macaca fascicularis*) (1-3 years old, weighing 1.7-3.2 kg) were used in this study. Primate work was performed according to animal use guidelines and approved procedures. Each animal was considered acclimated to the environment at the time of the study. NHPs were healthy and without a history of ear inflammation, ear surgery, signs of balance disorders, or other risk factors for dysfunction of the inner or middle ear. Monkeys received transmastoid/trans-RWM injections of 20 µL of AAV-SCBA-EGFP with doses of $5.8\times10^{10}$ VG (n=1 ear), $4.7\times10^{11}$ VG (n=2 ears), and $0.8\times10^{11}$ VG (n=1 ear). One animal was injected in one ear with vehicle (PBS) control.

NHP Surgical Procedures: Pre- and Post-Operative Anesthesia and Analgesia

Animals were sedated with ketamine hydrochloride (10 mg/kg) administered intramuscularly and pre-medicated with atropine (0.04 mg/kg) following overnight food deprivation. Prior to surgery, the animals were administered with dexamethasone (1 mg/kg) and buprenorphine (0.03 mg/kg) and received a single dose of buprenorphine sustained release (SR) (0.2 mg/kg) administered subcutaneously and cefazolin (20 mg/kg). To facilitate induction and intubation procedures, the animals were masked with isoflurane (1%-4%). Animals were intubated and maintained with oxygen (0.5-4 l) and isoflurane (~1%-5%) for the duration of the surgical procedure. Animals received warmed lactated Ringer's solution intravenously (10 mL/kg/h) during the surgery to improve recovery. A non-medicated lubricant was applied to protect the corneas. Hair was clipped from the surgical site, and any loose hair was removed. The surgical injection site was prepared for surgery using a povidone-iodine scrub solution and sponges soaked in 70% isopropyl alcohol. The animals were kept warm throughout the surgical preparation and procedure using warm-water-circulating heating blankets. Heart rate, respiratory rate, blood pressure (as applicable), end tidal carbon dioxide, and body temperature were continually monitored throughout the procedure and recorded at least every 20 min. The surgical site was prepared for aseptic surgery with a final application of Dura-Prep and allowed to dry prior to sterile draping. Bupivacaine (0.25-0.5 mL per site) was injected subcutaneously for local anesthesia at the incision sites either before the procedure or upon incision closure.

Injection Procedure

All viral inner-ear administrations were performed via the facial recess approach, with round-window injection as described. In brief, following a retroauricular incision, the mastoid bone was exposed and cortical mastoidectomy was performed. When the fossa incudis was reached, a 1- to 2-mm facial recess was then identified. A low drill speed and continuous fluid irrigation were used at this area to minimize thermal injury to the facial nerve. Then, the facial recess was opened to approach the RWM. Under direct visualization through the operating microscope, the needle was manually positioned into the round window and the needle held in place during the infusion. Viral vector injection was performed using a microinjection syringe pump (World Precision Instruments) at 2.0 µL/min for 10 min (for 20 µL total volume), using a Hamilton syringe connected via a thin, relatively non-compliant silicone tube to a 29 G, ~2-cm-long, sharp-end stainless steel injection needle. The syringe and catheter were filled with sterile saline and the needle backfilled with 30 µL of vector separated from saline by an air bubble in the catheter. Once the injection was completed, the surgical site was gently flushed with warm saline. The temporal muscles were approximated with interrupted tension sutures (far-near near-far sutures of 3-0 polydioxanone suture (PDS) followed by continuous subcutaneous and subcuticular sutures of absorbable suture material (4-0 PDS). The skin surrounding the surgical site was cleaned with saline in order and a topical antibiotic ointment was administered to the surgical site immediately after surgery. The surgical wounds were monitored for proper healing daily for 2 weeks.

Postoperative Treatment

The animal was allowed to recover from anesthesia and monitored continuously until fully alert. Local anesthesia for the skin incision was achieved using subcutaneous injection of bupivacaine (0.03 mg/kg) in the evening following surgery (day 0) and twice daily on days 1-3 post-surgery. Dexamethasone (0.5 mg/kg intramuscular) was administrated daily every 8-12 h for up to 5 days after surgery, to reduce fibrosis and inflammatory responses and nausea associated with surgery. Animals received cefazolin (20 mg/kg intramuscular) in the evening following surgery and 3 days later after surgery. Daily wound checks were performed throughout the study. Animals were monitored for evidence of pain and recovery and treated accordingly following completion of the regimen outlined above.

NHP Cochlear Processing, Histology, and Imaging

NHPs were euthanized at 21 days after vector injection and were perfused with heparinized saline followed by 4% formaldehyde. Collected temporal bones were postfixed for another 48 h in 4% formaldehyde. Then, cochleas were dissected from the temporal bones under a microscope as described 6 and were transferred to fresh 10% EDTA for 10-15 days until fully decalcified. For whole mounts, cochleas were micro dissected and immunostained. For cryosectioning, samples were cryoprotected by incubating in 10%, 20%, and 30% sucrose in PBS and then in NEG-50 (Richard-Allan Scientific) for 2 days, all at 4° C. Cochleas were embedded in NEG-50 and stored at −80° C. prior to sectioning. Cryosections were generated using a LeicaCM3050 S cryostat at 20 μm step size. After sectioning, slides were allowed to dry at −80° C. overnight.

The same protocol was used for whole-mount immunostaining and cochlear frozen sections. The following primary antibodies and secondary antibodies were used: rabbit polyclonal anti-MYO7A (Proteus Biosciences), mouse polyclonal anti-MYO7A (Proteus Biosciences), chicken anti-neurofilament-H (Millipore), rabbit monoclonal anti-EGFP (Thermo Fisher), chicken anti-EGFP (Ayes), donkey anti-rabbit IgG secondary antibody conjugated to Alexa Fluor 593, goat anti-chicken IgG conjugated to Alexa Fluor 488, a goat anti-chicken IgG conjugated to Alexa Fluor 647, donkey anti-mouse IgG conjugated to Alexa Fluor 593, and donkey anti-rabbit IgG conjugated to Alexa Fluor 488.

Samples were blocked and permeabilized with 10% donkey/10% goat serum with 0.3% Triton X-100 for 1 h at room temperature. Anti-MYO7A antibodies were used to label hair cells, anti-EGFP to amplify the EGFP signal, and anti-neurofilament-H to label nerve fibers and SGNs. Antibodies were diluted 1:500 in 10% donkey/10% goat serum supplemented with 0.1% Triton X-100/PBS and incubated overnight at room temperature followed by several rinses in HBSS. Next, samples were incubated in blocking solution for 30 min and incubated overnight at room temperature with secondary antibody in a 1:500 dilution in blocking solution. To label hair bundle actin, phalloidin conjugated to Alexa Fluor 405 (Life Technologies) (1:20) was used. DAPI was used to label cell nuclei.

Tissues were mounted on a Colorfrost glass slide (Thermo Fisher Scientific) using Prolong Gold Antifade mounting medium (Thermo Fisher Scientific). Imaging was performed with a Nikon Ti2 inverted spinning disk confocal using a Plan Apo λ20x/0.8 objective, Plan Fluor 40x/1.3 oil objective, Plan Apo λ60x/1.4 oil objective, or Plan Apo λ100x/1.45 oil objective.

For H&E-stained slides, samples were dried at 37° C. for 30 min. They were immersed in hematoxylin for 2 min, followed by rinsing in water and destaining with 0.5% hydrochloric acid in 70% ethanol, and rinsed again. Slides were then dipped in eosin for approximately 5 s and rinsed twice each for 1 min in 95% ethanol, 100% ethanol, and xylene. Samples were left to dry and were mounted with SignalStain mounting medium (Cell Signaling Technology). Slides were imaged using a Keyence BZ-X800 microscope, using BZ-Nikon Plan Apo λ10x/0.45 and Apo λ20x/0.75 objectives.

Quantification of Transduction Efficiency in Mice and NHPs

Whole-mount cochleas, immunostained as described earlier, were imaged with a Nikon Ti2 inverted spinning disk confocal using a Plan Fluor 40x/1.3 oil objective. Multiple images were taken along the cochlea from apical, mid-apical, middle, mid-basal, and basal regions. The laser intensity was chosen based on the specimen with the strongest EGFP signal to prevent fluorescence saturation, and the same settings were then used for each image of a set. The efficiency of IHC and OHC cell transduction was evaluated by two blinded investigators using the ImageJ program (NIH Image). HCs were identified with immunolabeling for MYO7A. Control uninjected whole-mount NHP samples were used to exclude autofluorescence.

ABR test in NHPs

A hearing test was performed before and 3 weeks after unilateral injection. The monkeys were anesthetized with a mixture of ketamine (10-15 mg/kg) and atropine (0.04 mg/kg). To facilitate induction and intubation procedures, the animal was masked with isoflurane (1%-4%). The animal was then intubated and maintained on isoflurane anesthesia (~1%-5% oxygen 0.5-4 l). After sedation, hair was clipped and skin cleaned with alcohol. The animals were kept warm throughout the testing procedure using warm-water-circulating heating blankets. Vital signs were monitored. The entire recording procedure generally lasted 40-60 min.

ABRs were acquired using a clinical-grade auditory evoked potential system (GSI Audera v2.7). Scalp potentials were recorded using subdermal needle electrodes applied in a 3-electrode configuration: the positive electrode at the high forehead, the negative electrode above the mastoid ipsilateral to the stimulated ear, and the common electrode at the low forehead at the midline just above the brow ridge. The click and tone pips stimulus were presented at alternate polarity with a tubal insert phone (TIP) 50 GSI generic. The acoustic click was presented at a repetition rate of 11.1 Hz, and waveforms were averaged across 2,004 stimulus repetitions. Clicks were a condensation stimulus of 100-ms duration. Sound levels were incremented in 5-dB steps, from ~15 dB nHL up to 54.5 dB nHL.

Tone frequencies of 500, 1,000, 2,000, and 4,000 Hz were used. The tone pips were presented at a repetition rate of 27 Hz. and wave forms were averaged across 2,016 stimulus repetitions. Sound levels were incremented in 5-dB steps, from ~10 dB nHL up to 59.5 dB nHL. GSI Audera v2.7 software was used to determine the ABR thresholds.

Statistics

Statistics was performed using GraphPad Prism. The IHC and OHC cell counting was performed by two blinded investigators using the ImageJ program (NIH Image). The results are shown as mean±SEM and as indicated in figure legends. Randomization was used whenever possible.

REFERENCES

1. Van Camp, G., and Smith, R. J. Hereditary Hearing Loss Homepage. hereditaryhearingloss.org.
2. Delmaghani, S., and El-Amraoui, A. (2020). Inner ear gene therapies take off: current promises and future challenges. J. Clin. Med. 9, 2309.
3. Yu, Q., Wang, Y., Chang, Q., Wang, J., Gong, S., Li, H., and Lin, X. (2014). Virally expressed connexin26 restores gap junction function in the cochlea of conditional Gjb2 knockout mice. Gene Ther. 21, 71-80.
4. György, B., Sage, C., Indzhykulian, A. A., Scheffer, D. I., Brisson, A. R., Tan, S., Wu, X., Volak, A., Mu, D., Tamvakologos, P. I., et al. (2017). Rescue of hearing by gene delivery to inner-ear hair cells using exosome-associated AAV. Mol. Ther. 25, 379-391.
5. György, B., Meijer, E. J., Ivanchenko, M. V., Tenneson, K., Emond, F., Hanlon, K. S., Indzhykulian, A. A., Volak, A., Karavitaki, K. D., Tamvakologos, P. I., et al. (2018). Gene transfer with AAV9-PHP.B rescues hearing in a mouse model of usher syndrome 3A and transduces hair cells in a non-human primate. Mol. Ther. Methods Clin. Dev. 13, 1-13.
6. Ivanchenko, M. V., Hanlon, K. S., Devine, M. K., Tenneson, K., Emond, F., Lafond, J. F., Kenna, M. A., Corey, D. P., and Maguire, C. A. (2020). Preclinical testing of AAV9-PHP.B for transgene expression in the non-human primate cochlea. Hear. Res. 394, 107930.
7. Isgrig, K., McDougald, D. S., Zhu, J., Wang, H. J., Bennett, J., and Chien, W. W. (2019). AAV2.7m8 is a powerful viral vector for inner ear gene therapy. Nat. Commun. 10, 427.
8. Lee, J., Nist-Lund, C., Solanes, P., Goldberg, H., Wu, J., Pan, B., Schneider, B. L., and Holt, J. R. (2020). Efficient viral transduction in mouse inner ear hair cells with utricle injection and AAV9-PHP.B. Hear. Res. 394, 107882.
9. Landegger, L. D., Pan, B., Askew, C., Wassmer, S. J., Gluck, S. D., Galvin, A., Taylor, R., Forge, A., Stankovic, K. M., Holt, J. R., and Vandenberghe, L. H. (2017). A synthetic AAV vector enables safe and efficient gene transfer to the mammalian inner ear. Nat. Biotechnol. 35, 280-284.
10. Hanlon, K. S., Meltzer, J. C., Buzhdygan, T., Cheng, M. J., Sena-Esteves, M., Bennett, R. E., Sullivan, T. P., Razmpour, R., Gong, Y., Ng, C., et al. (2019). Selection of an efficient AAV vector for robust CNS transgene expression. Mol. Ther. Methods Clin. Dev. 15, 320-332.
11. Tao, Y., Huang, M., Shu, Y., Ruprecht, A., Wang, H., Tang, Y., Vandenberghe, L. H., Wang, Q., Gao, G., Kong, W. J., and Chen, Z. Y. (2018). Delivery of adeno-associated virus vectors in adult mammalian inner-ear cell subtypes without auditory dysfunction. Hum. Gene Ther. 29, 492-506.
12. Suzuki, J., Hashimoto, K., Xiao, R., Vandenberghe, L. H., and Liberman, M. C. (2017). Cochlear gene therapy with ancestral AAV in adult mice: complete transduction of inner hair cells without cochlear dysfunction. Sci. Rep. 7, 45524.
13. Geng, R., Omar, A., Gopal, S. R., Chen, D. H., Stepanyan, R., Basch, M. L., Dinculescu, A., Furness, D. N., Saperstein, D., Hauswirth, W., et al. (2017). Modeling and preventing progressive hearing loss in usher syndrome III. Sci. Rep. 7, 13480.
14. Dai, C., Lehar, M., Sun, D. Q., Rvt, L. S., Carey, J. P., MacLachlan, T., Brough, D., Staecker, H., Della Santina, A. M., Hullar, T. E., and Della Santina, C. C. (2017). Rhesus cochlear and vestibular functions are preserved after inner ear injection of saline volume sufficient for gene therapy delivery. J. Assoc. Res. Otolaryngol. 18, 601-617.
15. György, B., Nist-Lund, C., Pan, B., Asai, Y., Karavitaki, K. D., Kleinstiver, B. P., Garcia, S. P., Zaborowski, M. P., Solanes, P., Spataro, S., et al. (2019). Allele-specific gene editing prevents deafness in a model of dominant progressive hearing loss. Nat. Med. 25, 1123-1130.
16. Keppeler, D., Merino, R. M., Lopez de la Morena, D., Bali, B., Huet, A. T., Gehrt, A., Wrobel, C., Subramanian, S., Dombrowski, T., Wolf, F., et al. (2018). Ultrafast optogenetic stimulation of the auditory pathway by targeting-optimized Chronos. EMBO J. 37, e99649.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A recombinant adeno-associated virus (rAAV), wherein the rAAV comprises:
   (i) an AAV capsid protein comprising an amino acid sequence at least 95% identical to amino acids 203-743 of SEQ ID NO: 3, wherein the amino acid sequence comprises S, T, T, L, Y, S, and P at the positions corresponding to positions 589, 590, 591, 592, 593, 594, and 595, respectively, of SEQ ID NO: 3; and
   (ii) a nucleic acid comprising two adeno-associated virus inverted terminal repeats (ITRs) flanking a transgene, wherein the transgene comprises a promoter operably linked to a nucleotide sequence encoding a human clarin-1 protein.

2. The rAAV of claim 1, wherein the human clarin-1 protein comprises the amino acid sequence of any one of SEQ ID NO: 5-9.

3. The rAAV of claim 1, wherein the nucleotide sequence encoding the human clarin-1 protein is at least 80% identical to the nucleotide sequence of SEQ ID NO: 10 or 19.

4. The rAAV of claim 1, wherein the transgene further comprises a 5' untranslated region (5' UTR).

5. The rAAV of claim 4, wherein the 5' UTR is a 5' UTR of a CLRN gene.

6. The rAAV of claim 5, wherein the 5' UTR comprises a nucleotide sequence at least 80% identical to the nucleotide sequence of SEQ ID NO: 16.

7. The rAAV of claim 1, wherein the transgene further comprises a 3' untranslated region (3' UTR).

8. The rAAV of claim 7, wherein the 3' UTR is a 3' UTR of a CLRN gene.

9. The rAAV of claim 8, wherein the 3' UTR comprises a nucleotide sequence at least 80% identical to the nucleotide sequence of SEQ ID NO: 17.

10. The rAAV of claim 1, wherein the promoter is a constitutive promoter, an inducible promoter, or a tissue specific promoter.

11. The rAAV of claim 1, wherein the transgene further comprises an enhancer, an intron, and/or a Woodchuck Hepatitis Virus Posttranscriptional Regulatory Element (WPRE).

12. The rAAV of claim 1, wherein the AAV ITRs are ITRs of one or more serotypes selected from the group consisting of AAV2, AAV3, AAV4, AAV5, and AAV6.

13. The rAAV of claim 1, wherein the AAV capsid protein has tropism for inner ear cells and/or eye cells.

14. A cell comprising the rAAV of claim 1.

15. A pharmaceutical composition comprising the rAAV of claim 1 and a pharmaceutically acceptable carrier.

16. A method for treating Usher syndrome Type 3A or a CLRN-associated disease in a subject in need thereof, the method comprising administering to the subject an effective amount of the rAAV of claim 1.

17. A recombinant adeno-associated virus comprising:
(i) an AAV capsid protein comprising an amino acid sequence at least 95% identical to amino acids 203-743 of SEQ ID NO: 3, wherein the amino acid sequence comprises S, T, T, L, Y, S, and P at the positions corresponding to positions 589, 590, 591, 592, 593, 594, and 595, respectively, of SEQ ID NO: 3; and
(ii) a nucleic acid comprising, from 5' to 3':
   (a) a 5' ITR;
   (b) a Human Cytomegalovirus Major Immediate-Early Enhancer (CMV IE enhancer);
   (c) a Chicken beta-actin (CBA) promoter;
   (d) a beta-actin exon;
   (e) a chimeric intron;
   (f) a 5' UTR;
   (g) a Kozak sequence;
   (h) a nucleotide sequence encoding a human clarin-1 protein;
   (i) a 3' UTR;
   (j) a bovine growth hormone poly A signal; and
   (k) a 3' ITR.

* * * * *

UNITED STATES PATENT AND TRADEMARK OFFICE
CERTIFICATE OF CORRECTION

| | | |
|---|---|---|
| PATENT NO. | : 12,129,287 B2 | Page 1 of 1 |
| APPLICATION NO. | : 17/474535 | |
| DATED | : October 29, 2024 | |
| INVENTOR(S) | : David P. Corey et al. | |

It is certified that error appears in the above-identified patent and that said Letters Patent is hereby corrected as shown below:

On the Title Page

Immediately following item (60) "Related US. Application Data", please insert the below section:
--(30) Foreign Application Priority Data
04/27/2021 [CA] ............... 3116391--

Signed and Sealed this
Eleventh Day of February, 2025

Coke Morgan Stewart
*Acting Director of the United States Patent and Trademark Office*